United States Patent [19]

Hodges et al.

[11] Patent Number: 5,436,260

[45] Date of Patent: Jul. 25, 1995

[54] ANGIOTENSIN II RECEPTOR ANTAGONISTS

[75] Inventors: John C. Hodges; Sylvester Klutchko, both of Ann Arbor, Mich.

[73] Assignee: Warner-Lambert Company, Morris Plains, N.J.

[21] Appl. No.: 177,019

[22] Filed: Jan. 4, 1994

Related U.S. Application Data

[60] Division of Ser. No. 978,650, Nov. 19, 1992, Pat. No. 5,308,853, which is a continuation-in-part of Ser. No. 811,184, Dec. 20, 1991, abandoned.

[51] Int. Cl.$^6$ .................. A61K 31/415; A61K 31/41
[52] U.S. Cl. ................... 514/389; 514/333; 514/341; 514/365; 514/370; 514/372; 514/374; 514/377; 514/378; 514/380; 514/381; 514/390; 514/391; 514/397
[58] Field of Search ............ 514/397, 389, 390, 391, 514/341, 365, 370, 374, 381

[56] References Cited

U.S. PATENT DOCUMENTS

| | | | |
|---|---|---|---|
| 4,335,040 | 10/1982 | Furukawa | 424/273 |
| 4,820,843 | 4/1989 | Aldrich | 548/252 |
| 5,322,950 | 6/1994 | Sircar et al. | 548/253 |
| 5,354,766 | 10/1994 | Naka et al. | 514/364 |
| 5,364,869 | 11/1994 | De | 514/340 |
| 5,376,666 | 12/1994 | Duncia | 514/303 |

FOREIGN PATENT DOCUMENTS

| | | |
|---|---|---|
| 0253310 | 7/1987 | European Pat. Off. . |
| 0291969 | 11/1988 | European Pat. Off. ... C07D 257/04 |
| 0401030 | 5/1990 | European Pat. Off. . |
| 0403158 | 6/1990 | European Pat. Off. . |
| 0403159 | 6/1990 | European Pat. Off. . |
| WO91/00277 | 1/1991 | WIPO . |

OTHER PUBLICATIONS

Meanwell et al., *J. Org. Chem.*, vol. 56, pp. 6897–6904 (1991).

*Primary Examiner*—Jacqueline Haley
*Attorney, Agent, or Firm*—Elizabeth M. Anderson

[57] ABSTRACT

Substituted 1-benzylimidazole-5-methylidene hydantoins are disclosed as well as methods of preparing them, pharmaceutical compositions containing them, and methods of using them. Intermediates useful in the preparation of the compounds of the invention are also disclosed and synthetic methods for preparing the novel intermediates. The compounds are useful as antagonists of angiotensin II and thus are useful in the control of hypertension, hyperaldosteronism, congestive heart failure, surgically induced vascular smooth muscle proliferation, and glaucoma.

12 Claims, No Drawings

ANGIOTENSIN II RECEPTOR ANTAGONISTS

This is a Divisional application of U.S. Ser. No. 07/978,650, filed Nov. 19, 1992, now U.S. Pat. No. 5,308,853, which is a Continuation-In-Part application of U.S. Ser. No. 07/811,184, filed Dec. 20, 1991, now abandoned.

BACKGROUND OF THE INVENTION

The present invention relates to novel substituted derivatives of 1-benzylimidazole-5-methylidene hydantoins which are useful as pharmaceutical agents, to methods for their preparation, to pharmaceutical compositions which include the compounds and a pharmaceutically acceptable carrier, and to pharmaceutical methods of treatment as well as the use of these agents as diagnostic tools. The novel compounds of the present invention are antagonists of angiotensin II (AII) useful in controlling hypertension, hyperaldosteronism, congestive heart failure, and glaucoma in mammals.

The enzyme renin acts on a blood plasma $\alpha_2$-globulin, angiotensinogen, to produce angiotensin I, which is then converted by angiotensin-converting enzyme to AII. The latter substance is a powerful vasopressor agent which has been implicated as a causative agent for producing high blood pressure in various mammals, such as rats, dogs, and humans. The compounds of this invention inhibit the action of AII at its receptors on target cells and thus prevent the increase in blood pressure produced by this hormone-receptor interaction. By administering a compound of the instant invention to a species of mammal with hypertension due to AII, the blood pressure is reduced. The compounds of the invention are also useful for the treatment of congestive heart failure, hyperaldosteronism, and glaucoma.

European Patent Application 0253310 discloses angiotensin II receptor blocking imidazoles of the formula

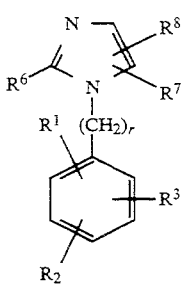

European Patent Application 0291969 discloses tetrazole intermediates to antihypertensive compounds

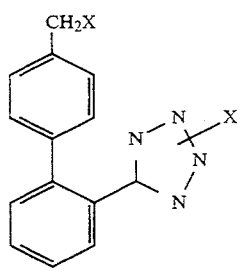

European Patent Application 401030 discloses substituted imidazo-fused 7-member ring heterocycles of Formula I and Ia

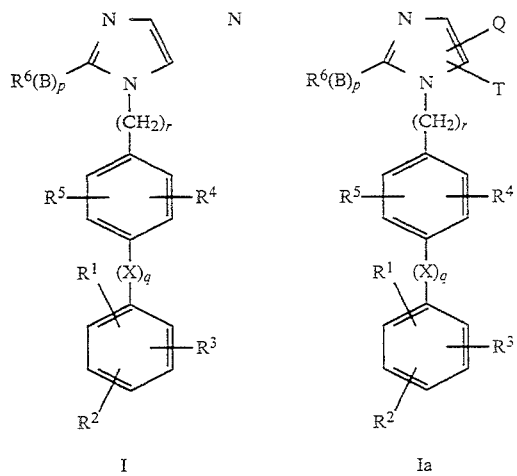

which are useful as angiotensin II antagonists.

WO 91/00277 discloses substituted imidazoles useful as angiotensin II blockers

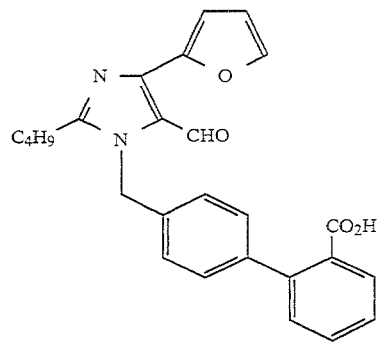

European Patent Applications 403158 and 403159 disclose angiotensin II receptor antagonists of formula

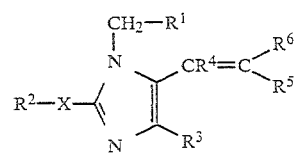

in which:

$R^1$ is phenyl, biphenyl, naphthyl, or adamantylmethyl, which are unsubstituted or substituted by 1 to 3 substituents selected from Cl, Br, F, I, $C_1$–$C_4$-alkyl nitro, $CO_2R^7$, tetrazol-5-yl, $C_1$–$C_4$-alkoxy, hydroxy, $SC_1$–$C_4$alkyl, $SO_2NHR^7$, $SO_3H$ $CONR^7R^7$, CN, $SO_2C_1$–$C_4$alkyl, or $C_nF_{2n1}$, wherein n is 1 to 3;

$R^2$ is $C_2$–$C_{10}$alkyl, $C_3$–$C_{10}$alkenyl, $C_3$–$C_{10}$alkynyl, $C_3$–$C_6$cycloalkyl, or $(CH_2)_{0-3}$phenyl unsubstituted or substituted by 1 to 3 substituents selected from $C_1$–$C_4$alkyl, nitro, Cl, Br, F, I, hydroxy, $C_1$–$C_4$alkoxy, or $NR^7R^7$;

X is a single bond, S, or O:

$R^3$ is hydrogen, Cl, Br, F, I, CHO, hydroxymethyl, COOR$^7$, CONR$^7$R$^7$, NO$_2$, or C$_n$F$_{2n1}$, wherein n is 1 to 3;

$R^4$ and $R^5$ are independently hydrogen, C$_1$-C$_5$alkyl, phenyl-Y-, naphthyl -Y-, or biphenyl -Y-, wherein the aryl groups are unsubstituted or substituted by 1 to 3 substituents selected from Cl, Br, F, I, C$_1$-C$_4$alkoxy, hydroxy, CO$_2$R$^7$, CN, NO$_2$, tetrazol-5-yl, SO$_3$H, CF$_3$, CONR$^7$R$^7$, SO$_2$NHR$^7$, C$_1$-C$_4$-alkyl, or NR$^7$R$^7$, or by methylenedioxy, phenoxy, or phenyl, except that R$^4$ and R$^5$ are not both selected from hydrogen or C$_1$-C$_6$alkyl;

Y is a single bond, O, S, or C$_1$-C$_6$alkyl which is straight or branched or optionally substituted by phenyl or benzyl, wherein each of the aryl groups is unsubstituted or substituted by halo, NO$_2$, CF$_3$, C$_1$-C$_4$alkyl, C$_1$-C$_4$alkoxy, CN, or CO$_2$R$^7$;

R$^6$ is —Z—COOR$^6$ or —Z—CONR$^7$R$^7$;

Z is a single bond, vinyl, CH$_2$—)—CH$_2$—, methylene optionally substituted by C$_1$-C$_4$-alkyl, 1 or 2 benzyl groups, thienylmethyl, or furylmethyl, or —C-(O)NHCHR$^9$—, wherein R$^9$ is H, C$_1$-C$_4$-alkyl, phenyl, benzyl, thienylmethyl, or furylmethyl;

each R$^7$ independently is hydrogen, C$_1$-C$_4$-alkyl, or (CH$_2$)$_m$phynyl, wherein m is 0 to 4; and R$^6$ is hydrogen, C$_1$-C$_6$alkyl, or 2-di(C$_1$-C$_4$-alkyl)amino-2oxoethyl; or R$^5$ and R$^6$ are both hydrogen, R$^4$ is —Z—COOR$^8$ and Z is other than a single bond; or a pharmaceutically acceptable salt thereof.

U.S. Pat. No. 5,355,040 discloses imidazole-5-acetic acid derivatives of the formula

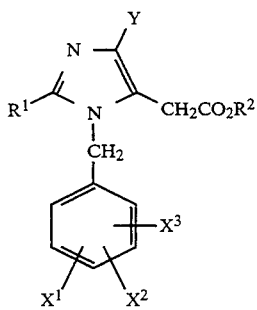

wherein R$^1$ is lower alkyl, cycloalkyl or, phenyl which may be substituted with 1 to 3 of halogen, nitro, amino, mono(lower alkyl)amino, di(lower alkyl)amino, lower alkyl, lower alkoxyl, benzyloxyl and/or hydroxyl; X$^1$, X$^2$ and X$^3$ are each hydrogen halogen, nitro amino, lower alkyl, lower alkoxyl, benzyloxyl or hydroxyl; Y is halogen and R$^2$ is hydrogen or lower alkyl; provided that X$^1$ is halogen, lower alkyl, lower alkoxyl, benzyloxyl or hydroxyl when R$^1$ is unsubstituted or substituted phenyl only with 1 halogen, di(lower alkyl)amino, lower alkyl or lower alkoxyl, and its salts. The compounds are disclosed as having antihypertensive activity.

However, the compounds disclosed in the above references do not disclose or suggest the novel combination of structural variations found in the compounds of the present invention described hereinafter.

SUMMARY OF THE INVENTION

The present invention is a compound of Formula I or Ia

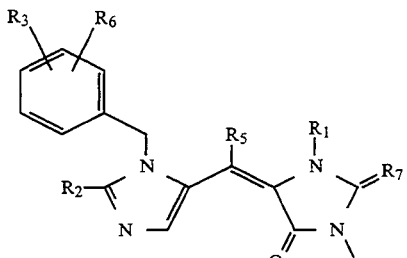

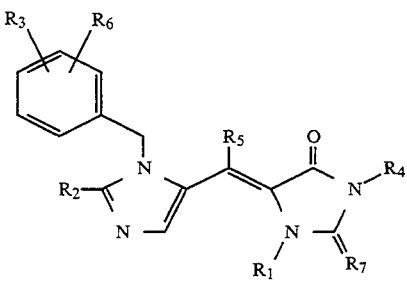

or a pharmaceutically acceptable salt thereof wherein R$_1$, $_2$, R$_3$, R$_4$, R$_5$, R$_6$, and R$_7$ are as defined below.

Preferred compounds of the instant invention are those of Formula I or Ia wherein R$_1$ is
hydrogen,
methyl,
ethyl,
n-propyl,
i-propyl,
n-butyl,
i-butyl,
sec-butyl,
t-butyl,
n-amyl,
i-amyl,
n-hexyl,
aryl,
CH$_2$-aryl,
CH$_2$-heteroaryl, or
CHJ$_2$-cycloalkyl wherein aryl, heteroaryl, and cycloalkyl are as defined below in the detailed description of the invention;

R$_2$ is
methyl,
ethyl,
propyl,
iopropyl,
n-butyl,
n-pentyl,
2-propenyl,
2-butenyl,
3-butenyl, or
cyclopropyl, R$_3$ is
(CH$_2$)$_n$CO$_2$Y or $$(CH_2)_m$$
$$-C-CO_2Y$$

wherein Y is hydrogen or lower alkyl, n is 0 to 1, m is 2 to 5;

R₄ is
hydrogen,
alkyl or branched alkyl of from 1 to 8 carbon atoms,
—(CH₂)ₘX(CH₂)ₙH m=1-6, n=0-6, and X=O, N, S;

R₅ is hydrogen;

R₆ is
hydrogen,
chlorine,
fluorine,
methyl,
trifluoromethyl, or
methoxy; and

R₇ is oxygen.

More preferred compounds of the instant invention are those of Formula I or Ia wherein R₁ is n-butyl, n-pentyl, n-propyl, benzyl, 2-thienylmethyl, 3-thienylmethyl, cyclopropylmethyl, cyclohexylmethyl, cyclopentylmethyl, 2-methyl-4-thiazolylmethyl, 2-amino-4-thiazolylmethyl, or 4-thiazolylmethyl;

R₂ is butyl and propyl;

R₃ is (CH₂)ₙCO₂Y wherein n is O, Y is hydrogen or methyl;

R₄ is hydrogen or alkyl of 3 to 6 carbons;

R₅ and R₆ are each hydrogen; and

R₇ is oxygen.

Still more preferred compounds of the instant invention are selected from (E) -4-[[2-Butyl-5-[(3-butyl-2,5-dioxo-4-imidazole-1-yl]methyl]benzoic acid and its methyl ester, (Z) -4-[[2-Butyl-5-[(3-butyl-2,5-dioxo-4-imidazolidinylidene)methyl]-1H-imidazole-1-yl]methyl]benzoic acid and its methyl ester, (E) -4-[[2-Butyl-5-[[2,5-dioxo-3-(3-methylbutyl)-4-imidazolidinylidene]methyl]-1H-imidazole-1-yl]methyl]benzoic acid and its methyl ester, (Z) -4-[[2-Butyl-5-[[2,5-dioxo-3-(3-methylbutyl) -4-imidazolidinylidene]methyl]-1H-imidazole-1-yl]methyl]benzoic acid and its methyl ester, (E)-4-[[2-Butyl-5-[(2,5-dioxo-3-methyl-4-imidazolidinylidene)methyl]-1H-imidazole-1-yl]methyl]benzoic acid and its methyl ester, (Z)-4-[[2-Butyl-5-[(2,5-dioxo-3-methyl-4-imidazolidinylidene)methyl]-1H-imidazole-1-yl]methyl]benzoic acid and its methyl ester, (E)-4-[[2-Butyl-5-[(2,5-dioxo-3- (phenylmethyl)-4-imidazolidinylidene)methyl]-1H-imidazole-1-yl]methyl]benzoic acid and its methyl ester, (Z)-4-[[2-Butyl-5-[(2,5-dioxo-3- (phenylmethyl)-4-imidazolidinylidene)methyl]-1H-imidazole-1-yl]methyl]benzoic acid and its methyl ester, (E)-4-[[2-Butyl-5-[(2,5-dioxo-3-phenyl-4-imidazolidinylidene)methyl]-1H-imidazole-1-yl]methyl]benzoic acid and its methyl ester, (Z) -4-[[2-Butyl-5-[(2,5-dioxo-3-phenyl-4-imidazolidinylidene)methyl]-1H-imidazole-1-yl]methyl]benzoic acid and its methyl ester, (E) -4-[[2-Butyl-5-[[2,5-dioxo-3- ((2-thienyl)methyl)-4-imidazolidinylidene ]-methyl]-1H-imidazole-1-yl]methyl]benzoic acid and its methyl ester, (Z) -4-[[2-Butyl-5-[[2,5-dioxo-3- ((2-thienyl) methyl)-4-imidazolidinylidene]methyl]-1H-imidazole-1-yl]methyl]benzoic acid and its methyl ester, (E) -4-[[2-Butyl-5-[[2,5-dioxo-3- (4-hydroxybutyl) 4-imidazolidinylidene]methyl]- 1H- imidazole- 1-yl]methyl]benzoic acid and its methyl ester, (Z) -4-[[2-Butyl-5-[[2,5-dioxo-3- (4-hydroxybutyl) 4-imidazolidinylidene]methyl]- 1H- imidazole- 1-yl]methyl]benzoic acid and its methyl ester, (E) 40[[2-Butyl-5-[(3-butyl-1-methyl-2,5-dioxo-4-imidazol-1-idinylidene)methyl]-1H-imidazole-1-yl]methyl]benzoic acid and its methyl ester, (Z)-4-[[2-Butyl-5-[(3-butyl-1-methyl-2,5-dioxo-4-imidazolidinylidene)methyl]-1H-imidazole-1-yl]methyl]benzoic acid and its methyl ester, (Z) -4-[[2-butyl-5-[[3-[(4-chlorophenyl)methyl]-2,5-dioxo-4-imidazolidinylidene]methyl]-1H-imidazol-1-yl]methyl]benzoic acid and its methyl ester, (E) -4-[[2-butyl-5-[[3-[(4-chlorophenyl)methyl]-2,5-dioxo-4-imidazolidinylidene]methyl]-1H-imidazolyl]-methyl]benzoic acid and its methyl ester, (Z) -4-[[2-butyl-5-[[1-butyl-3-(cyclohexylmethyl)-2,5-dioxo-4-imidazolidinylidene]methyl]- 1H- imidazolyl]-methyl]benzoic acid and its methyl ester, (E) -4-[[2-butyl-5-[[1-butyl-3-(cyclohexylmethyl)-2,5-dioxo-4-imidazolidinylidene]methyl]-1H-imidazolyl]methyl]benzoic acid and its methyl ester, (Z) -4-[[2-butyl-5-[[1obutyl-2,5-dioxo-3-pentyl-4imidazol-idinylidene]methyl]-1H-imidazol-1-yl]methyl]benzoic acid and its methyl ester, (E) -4-[[2-butyl-5-[[1-butyl-2,5-dioxo-3-pentyl-4-imidazol-idinylidene]methyl]-1H-imidazol-1-yl]methyl]benzoic acid and its methyl ester, (Z) -4-[[2-butyl-5-[(1,3-dibutyl-2,5-dioxo-4imidazolidinylidene) methyl]-1H-imidazol-1-yl]methyl]benzoic acid and its methyl ester, (E ) - 4-[[2-butyl-5-[(1,3-dibutyl-2,5-dioxo-4-imidazolidinylidene) methyl]-1H-imidazol -1-yl]methyl]benzoic acid and its methyl ester, (Z) -4-[[2-butyl-5-[[1-butyl-2,5-dioxo-3-(4,4,4-trifluorobutyl)-4-imidazolidinylidene]methyl]-1H -imidazol-1-yl[methyl]benzoic acid and its methyl ester, (E) -4-[[2-butyl-5-[[1-butyl-2,5-dioxo-3-(4,4,4-trifluorobutyl)-4-imidazolidinylidene]methyl]-1H-imidazol-1-yl]methyl]benzoic acid and its methyl ester, (Z) -4-[[2-butyl-5-[[2,5-dioxo-1,3-bis(4,4,4-trifluorobutyl)-4-imidazolidinylidene]methyl]-H-imidazol-1-yl]methyl]benzoic acid and its methyl ester, (E) -4-[[2-butyl-5-[[2,5-dioxo-1,3bis(4,4,4-trifluorobutyl)-4-imidazolidinylidene]methyl]-1H-imidazol-1-yl]methyl]benzoic acid and its methyl ester, (Z) -4-[[2-butyl-5-[[1-butyl-2,5-dioxo-3-(3-thienylemthyl)-4-imidazolidinylidene]methyl]-1H-imidazol-1-yl]methyl]benzoic acid and its methyl ester, imidazol-1-yl]methyl]benzoic acid and its methyl ester, (E) -4-[[2-butyl-5-[[1-butyl-2,5-dioxo-3-(3-thienylmethyl)-4-imidazolidinylidene]methyl]-1H-imidazol-1-yl]methyl benzoic acid and its methyl ester, (Z) -4-[[2-butyl-5-[[1-butyl-2,5-dioxo-3-(2-thienylmethyl)-4-imidazolidinylidene]methyl]- 1H-imidazol-1yl]-methyl]benzoic acid and its methyl ester, (E) -4-[[2-butyl-5-[[1-butyl-2,5-dioxo-3-(2-thienylmethyl)-4-imidazolidinylidene]methyl]-1H-imidazol-1-yl]methyl]benzoic acid and its methyl ester, g (Z) -4-[[2-butyl-5-[[1-butyl-3-[(5-methyl-2-thienyl)-methyl]-2,5-dioxo- 4- imidazolidinylidene]methyl]-1H-imidazol-1-yl]methyl]benzoic acid and its methyl ester, (E) -4-[[2-butyl-5-[[1-butyl-3-[(5-methyl-2-thienyl)methyl]-2,5-dioxo-4-imidazolidinylidene]methyl]-1H-imidazol-1-yl]methyl]benzoic acid and its methyl ester, (Z) -4-[[2-butyl-5-[[1-butyl-2,5-dioxo-3- (4-thiazolyl-methyl)-4 -imidazolidinylidene]methyl]-1H-imidazol-1-yl]methyl]benzoic acid and its methyl ester, (E) -4-[[2-butyl-5-[[1-butyl-2,5-dioxo-3- (4-thiazolyl)-methyl)-4-imidazolidinylidene]methyl]-1H-imidazol-1-yl]methyl]benzoic acid and its methyl ester, (Z) -4-[[2-Butyl-5-[[3-[(2-methyl-4-thiazoly) methyl]-2,5-dioxo-1-(4,4,4-trifluorobutyl)-4-imidazolidene]methyl]- 1H- imidazol- 1- yl]methyl]benzoic acid and its methyl ester, (E) -4-[[2-Butyl-5-[[3-[(2-methyl-4-thiazoly) methyl]-2,5-dioxo-1-(4,4,4-trifluorobutyl)-4-imidazol idene]methyl]-1H-imidazol-1-yl]methyl]benzoic acid and its methyl ester, (Z) -4-[[2-butyl-5-[[1-butyl-3-[(2-methyl-4-thiazolyl)-methyl]-2,5-dioxo-4-imidazolidinylidene]methyl]-1H-imidazol-1-yl]methyl]benzoic acid and its methyl ester, (E) -4-[[2-butyl-5-[[1-butyl-3-[(2-methyl-4-thiazolyl)-methyl]-2,5-dioxo-4-imidazolidinylidene]methyl]-1H-imidazol-1-yl]methyl]benzoic acid and its methyl ester, (Z) -4-[[2-butyl-5-[[1-butyl-3-[(2-amino-4-thiazolyl)-methyl]-2,5-dioxo-4-imidazolidinylidene]methyl]-1H-imidazol-1-yl]methyl]benzoic acid and its methyl ester, (E) -4-[[2-butyl-5-[[1-butyl-3-[(2-amino-4-thiazolyl)-methyl]-2,5-dioxo-4-imidazolidinylidene]methyl]-1H-imidazol-1-yl]methyl]benzoic acid and its methyl ester, (Z) -4-[[2-butyl-5-[[1-butyl-2,5-dioxo-3-(2-pyridinyl-methyl)-4- imidazolidinylidene]methyl]- 1H-imidazol-1-yl]methyl]benzoic acid and its methyl ester, (E) -4-[[2-butyl-5-[[1-butyl-2,5-dioxo-3-(2-pyridinyl-methyl)-4-imidazolidinylidene]methyl]- 1H -imidazol-1-yl]methyl]benzoic acid and its methyl ester, (Z) -4-[[2-butyl-5-[[1-butyl-2,5-dioxo-3-(1H-tetrazol-5-ylmethyl)-4-imidazolidinylidene]methyl]- 1-imidazol-1-yl]methyl]benzoic acid and it its methyl ester, (E) -4-[[2-butyl-5-[[1-butyl-2,5-dioxo-3- (1H-tetrazol-5-ylmethyl)-4-imidazolidinylidene]methyl]-1H-imidazol-1-yl]methyl]benzoic acid and its methyl ester, (Z) -4-[[2-butyl-5-[[1-butyl-3- (1H-imidazol-5-ylmethyl)-2,5-dioxo-4- imidazolidinylidene]methyl]-1-imidazol-1-yl]methyl]benzoic acid and its methyl ester, (E) -4-[[2-butyl-5-[[1-butyl-3-(1H-imidazol-5-ylmethyl)-2,5-dioxo -4-imidazolidinylidene]methyl]-1H-imidazol -1-yl]methyl]benzoic acid and its methyl ester, (Z) -4-[[2-butyl-5-[[1-butyl-3-[(5-methyl-3-isoxazolyl)methyl]-2,5-dioxo-4-imidazolidinylidene]methyl]- 1H-imidazol-1-yl]methyl]benzoic acid and its methyl ester, (E) -4-[[2-butyl-5-[[1-butyl-3-[(5-methyl-3-isoxazolyl)methyl]-2,5-dioxo 4- imidazolidinylidene]methyl]-1H-imidazol-1-yl]methyl]benzoic acid and its methyl ester, (Z) -4-[[2-butyl-5-[[1-hexyl-2,5-dioxo-3- (3-thienylmethyl)-4-imidazolidinylidene]methyl]-1H-imidazol-1-yl]methyl]benzoic acid and its methyl ester, (E)-4-[[2-butyl-5-[[1-hexyl-2,5-dioxo-3-(3-thienylmethyl)-4-imidazolidinylidene]methyl]- 1H -imidazol-1-yl]methyl]benzoic acid and its methyl ester, (Z) -4-[[2-butyl-5-[1-hexyl-3-[(2-methyl-4-thiazolyl)-2,5-dioxo-4-imidazolidinylidene]methyl]-1H-imidazol-1-yl]methyl]benzoic acid and its methyl ester, (E) -4-[[2-butyl-5-[hexyl-3-[(2-methyl-4-thiazolyl)-methyl]-2,5-dioxo-4-imidazolidinylidene]methyl]-1H-imidazol-1-yl]methyl]benzoic acid and its methyl ester, (Z) - 4-[[2-butyl-5-[J 1-(cyclopropylmethyl)-2,5-dioxo-3-(2-thienylmethyl)-4-imidazolidinylidene]methyl]-1H-imidazol-1-yl]methyl]benzoic acid and its methyl ester, (E) -4-[[2-butyl-5-[[1-(cyclopropylmethyl) -2,5-dioxo - 3-(2-thienylmethyl)-4- imidazolidinylidene]methyl]-1H-imidazol-1-yl]methyl]benzoic acid and its methyl ester, (Z) -4-[[2-butyl-5-[[1-(methoxymethyl) -3-[(2-methyl-4-thiazolyl)methyl]-2,5-dioxo-4-imidazolidinylidene]-methyl]- 1H- imidazol - 1-yl]methyl]benzoic acid and its methyl ester, (E) -4-[[2-Butyl-5-[[1-(methoxymethyl) -3-[(2-methyl-4- thiazolyl)methyl]- 2,5-dioxo- 4- imidazolidinylidene]-methyl]-1H-imidazol-1-yl]methyl]benzoic acid and its methyl ester, (Z) -4-[[2-butyl-5-[[1-(hydroxymethyl) -3-[(2-methyl-4- thiazolyl)methyl]-2,5-dioxo-4-imidazolidinylidene]-methyl]-1H-imidazol-1-yl]methyl]benzoic acid and its methyl ester, (E) -4-[[2-butyl-5-[[1-(hydroxymethyl)-3-[(2-methyl-4-thiazolyl)methyl]-2,5-dioxo-4-imidazolidinylidene]-methyl]-1H-imidazol - 1-yl]methyl]benzoic acid and its methyl ester, (Z) -4-[[2-butyl-5-[[1-butyl-3-[(2-methyl-4-thiazolyl)-methyl]-2,5-dioxo-4-imidazolidinylidene]methyl]-1H-imidazol-1-yl]methyl]-3-chlorobenzoic acid and its methyl ester, (E) -4-[[2-butyl-5-[[1-butyl-3-[(2-methyl-4-thiazolyl)-methyl]-2,5-dioxo-4-imidazol idinylidene]methyl]-1H-imidazol-yl]-methyl]- 3- chlorobenzoic acid and its methyl ester, (Z) -N-[4-[[2-butyl-5-[(3-butyl-2,5-dioxo-4-imidazol idinylidene)methyl]-1H-imidazol-1-yl]methyl]phenyl]-1,1,1- trifluoromethanesulfonamide, (E)-N-[4-[[2-butyl-5-[(3-butyl-2,5-dioxo-4-imidazol idinylidene)methyl]-1H-imidazol-1-yl]methyl]phenyl]-1,1,1-trifluoromethanesulfonamide, (Z) -1-Butyl-5-[[2-butyl-3-[[4-(1H-tetrazol-5-yl)-phenyl]methyl]-3H-imidazol-4-yl]methylene]-2,4-imidazolidinedione, (E)-1-Butyl-5-[[2-butyl-3-[[4-(1H-tetrazol-5-yl)-phenyl]methyl]-3H-imidazol-4-yl]methylene]-2,4-imidazolidinedione, (Z) -4-[[2-butyl-5-[(3-butyl-2,5-dioxo-4-imidazol idinylidene)methyl]-1H-imidazol-1-yl]methyl]-3-chlorobenzoic acid and its methyl ester, (E) -4-[[2-butyl-5-[(3-butyl-2,5-dioxo-4-imidazol idinylidene)methyl]-1H -imidazol-1-yl]methyl chlorobenzoic acid and its methyl ester, (Z)-1-Butyl-5-[[2-butyl-3-[[2'-(1H-tetrazol-5-yl) [1,1'-biphenyl]-4-yl]methyl]-3H-imidazol-4-yl ]methylene]-2,4-imidazolidinedione, (E) -1-Butyl-5-[[2-butyl-3-[[2'-(1H-tetrazol-5-yl) [1,1'-biphenyl]-4-yl]methyl]-3H -imidazol-4-yl ]methylene]-2,4- imidazolidinedione, 1-Butyl-5-[[2-butyl-3-[[2'-(1H-tetrazol-5-yl) [1,1'-biphenyl]-4-yl]methyl]-3H-imidazol-4-yl ]methyl]-2,4-imidazolidinedione, (Z) -5-[[2-butyl-3-[[2'-(1H-tetrazol-5-yl) [1,1'-biphenyl ]-4-yl]methyl]-3H-imidazol-4-yl]methylene]1-methyl-2,4- imidazolidinedione, (E) -5-[[2-butyl-3-[[2'-(1H-tetrazol-5-yl) [1,1'-biphenyl ]-4-yl]methyl]-3H-imidazol-4-yl]methylene]1-methyl-2,4-imidazolidinedione, (Z) -4'-[[2-butyl-5-[(3-butyl-2,5-dioxo-4-imidazolidinylidene)methyl]-1H-imidazol-1yl]methyl][1,1'-biphenyl]-2-carboxylic acid and its methyl ester, (E) -4'- [[2-butyl-5-[(3-butyl-2,5-dioxo-4-imidazolidinylidene)methyl]-1H-imidazol-1-yl]methyl]phenyl]cyclopentanecarboxylic acid and its methyl ester, (Z) -1-[4-[[2-butyl-5-[[1-butyl-[3-(2-methyl-4-thiazoly)methyl]-2,5-dioxo-4-imidazolidinylidene]methyl]-1H-imidazol-1-yl]methyl]phenyl]cyclopentanecarboxylic acid and its methyl ester, (Z) -4-[[2-Butyl-5-[[2,5-dioxo-1,3-bis(2-thienylmethyl)-4-imidazolidinylidene[methyl]1H-imidazol-1-]methyl]benzoic acid and its methyl ester, (E) -4-[[2-Butyl-5-[[2,5-dioxo-1,3-bis(2-thienylmethyl)-4-imidazolidinylidene]methyl]-1H-imidazol-1-yl]-methyl]benzoic acid and its methyl ester, (Z) -4-[[2-butyl-5-[[3-butyl-1-[(2-methyl-4-thiazolyl)-methyl]-2,5-dioxo-4-imidazolidinylidene]methyl]-1H-imidazol-1-yl]methyl]benzoic acid and its methyl ester, and (E) -4-[[2-butyl-5-3-butyl-1-[(2-methyl-4-thiazolyl)-methyl]-2,5-dioxo-4-imidazolidinylidene]methyl]-1H-imidazol-1-yl]methyl]benzoic acid and its methyl ester.

Preferred useful intermediates in the invention are

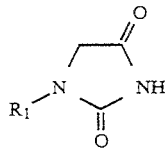

and

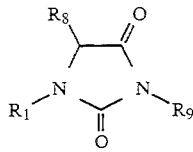

wherein R₁ is H,
Me,
n-Bu,
CH₂Ph; or

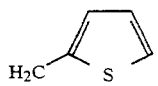

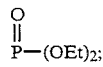

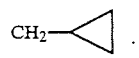

Angiotensin II mediates a variety of responses in various tissues, including contraction of vascular smooth muscle, excretions of salt and water from kidney, release of prolactin from pituitary, stimulation of aldosterone secretion from adrenal gland, and regulation of cell growth in both cardiac and vascular tissue. As antagonists of angiotensin II, the compounds of the instant invention are useful in controlling hypertension, hyperaldosteronism, and congestive heart failure in mammals. Compounds of the instant invention also have utility in prevention of vascular occlusion due to smooth muscle proliferation following vascular surgeries such as angioplasty, coronary bypass, transplantation, and the like. Additionally, antihypertensive agents as a class have been shown to be useful in lowering intraocular pressure. Thus, the other inventions are also useful in treating and/or preventing glaucoma.

The present invention is also a pharmaceutical composition for administering an effective amount of a compound of Formula I or Ia in unit dosage form in the treatment methods mentioned above.

Finally, the present invention is directed to methods for the preparation of a compound of Formula I or Ia and synthetic intermediates.

DETAILED DESCRIPTION

This invention is a compound of Formula I or Ia

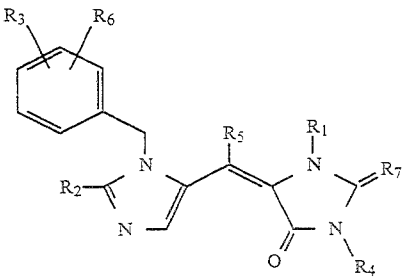

or

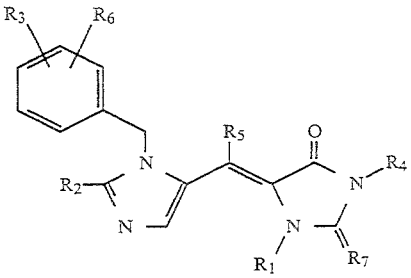

or a pharmaceutically acceptable salt thereof wherein:
R₁ is
—hydrogen,
—straight or branched alkyl or alkenyl from 1 to 8 carbon atoms;
—alkyl as above with HO, $NO_2$, CN, $NH_2$, $CO_2H$, $CONH_2$, $CO_2CH_3$, $CO_2C_2H_5$, or $COHH_2$ substituents;
—$(CH_2)_n$aryl wherein n is an integer from 0 to 3 and aryl is Ph or Ph substituted with Cl, Br, I, F, $CH_3$, $OCH_3$, OH, $NO_2$, CN, $CONH_2$, $CO_2H$, $NH_2$, $NHCH_3$, or $N(CH_3)_2$ groups, methylenedioxy;
—$(CH_2)_n$heteroaryl wherein n is an integer from 0 to 3 and heteroaryl is 2-thienyl, 3-thienyl, 2-furanyl, 3-furanyl, 2-pyrrolyl, 3-pyrrolyl, 2-pyridyl, 3-pyridyl, 4-pyridyl, 2-thiazolyl, 2-oxazolyl, 2-imidazolyl, 4-thiazolyl, 4-oxazolyl, 4-imidazolyl, 5-thiazolyl, 5-oxazolyl, 5-tetrazole, 3-isoxazole, 4-isoxazole, or 5-isoxazole;
—$(CH_2)_n$heteroaryl as above with Me, Et, Pr, Butyl, Cl, Br, I, F, OMe, OH, $NO_2$, $NH_2$, NHMe, NMe₂, $CO_2R$, $SO_2NHR$, $SO_3H$, $CONR_2$ substituents;

—$(CH_2)_n$cycloalkyl wherein n is an integer from 0 to 3 and cycloalkyl is a saturated or unsaturated ring of 3 to 7 carbon atoms;

—$(CH_2)_n$H where X is O, S, N, and m and n are each independently integral from 1 to 6 carbon atoms;

$R_2$ is

—$(CH_2)_n$cycloalkyl, wherein n is an integer from 0 to 3, of from 3 to 6 carbon atoms;

alkyl of from 1 to 6 carbon atoms, or alkenyl of from 2 to 6 carbon atoms, $OC_1$-$C_5$ alkyl, and $SC_1$-$C_5$ alkyl;

$R_3$ is $(CH_2)_nCO_2Y$ or $$\begin{array}{c}(CH_2)_m\\ \\-C-CO_2Y\end{array}$$

wherein Y is hydrogen or lower alkyl, n is an integer of from 0 to 8, and m is an integer of from 2 to 7;

$CH_2SO_2NHCOR$,
$NHSO_2NHCOR$,
$NHCONHSO_2R$,
$PO(OR)_2$,
$CONHSO_2R$,
$SO_3H$,
$B(OH)_2$
—$SO_2NHCOR$,

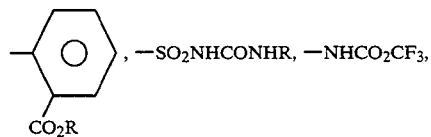

—$SO_2NHCONHR$, —$NHCO_2CF_3$,

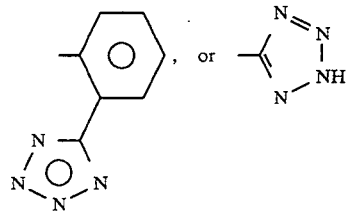

$R_4 = R_1$ $R_5$ is hydrogen or alkyl of from 1 to 4 carbon atoms;

$R_6$ is hydrogen, chlorine, bromine, fluorine, methyl, trifluoromethyl, or methoxy; and $R_7$ is oxygen or sulfur.

Certain compounds of the present invention can exist in unsolvated forms as well as solvated forms, including hydrated forms. In general, the solvated forms, including hydrated forms, are equivalent to unsolvated forms and are intended to be encompassed within the scope of the present invention.

Both E- and Z-isomers, for example, a compound of Formula I or Ia are included.

Certain compounds of the present invention possess 1 or more chiral centers and each center may exist in the R(D) or S(L) configuration. The present invention includes all enantiomeric and epimeric forms as well as the appropriate mixtures thereof.

In the compounds of Formula I or Ia, the term "alkyl" means a straight or branched hydrocarbon radical having from 1 to 8 carbon atoms and includes, for example, methyl, ethyl, n-propyl, isopropyl, n-butyl, sec-butyl, isobutyl, tert-butyl, n-pentyl, n-hexyl, and the like, except where specifically stated otherwise.

The term "alkenyl" is an alkyl group as above bearing 1 double bond at any position with E- or Z-geometry.

The compounds of Formula I or Ia are capable of further forming both pharmaceutically acceptable acid addition and/or base salts. All of these forms are within the scope of the present invention.

Pharmaceutically acceptable acid addition salts of the compound of Formula I or Ia include salts derived from nontoxic inorganic acids such as hydrochloric, nitric, phosphoric, sulfuric, hydrobromic, hydriodic, phosphorous, and the like, as well as the salts derived from nontoxic organic acids, such as aliphatic mono and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, targrate, methanesulfonate, and the like. Also contemplated are salts of amino acids such as arginate and the like and gluconate, galacturonate (see, for example, Berge, S. M.,., et al, "Pharmaceutical Salts," *Journal of Pharmaceutical Science* 1977;66:1-19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procains (see, for example, Berge, S. M., etal, "Pharmaceutical Salts," *Journal of Pharmaceutical Science* 1977;66:1-19).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Compounds of Formula I or Ia and intermediates therefor may be prepared according to the syntheses outlined in Schemes I-VII below. Although these schemes often indicate exact structures, the methods apply widely to analogous compounds of Formula I or Ia and intermediates therefor, given appropriate consideration to protection and deprotection of reactive functional groups by methods standard to the art of organic chemistry. The strategy for preparation of compounds of Formula I or Ia involves oxidation of a 4-chloroimidazol-5-methanol such as 1 (Scheme I) with manganese dioxide in an inert solvent such as tetrahydrofuran, dioxane, acetone, dichloromethane, and the like. The resulting aldehyde, 2, is then alkylated with a benzyl halide in the presence of a weak inorganic base such as $Na_2CO_3$, $K_2CO_3$, or $Cs_2CO_3$ in a polar, aprotic solvent like DMF, DMA, N-methyl pyrrolidone or DMSO. Preferred conditions for the benzylation employ 1 to 5 equivalents of $Cs_2CO_3$ in DMF at 0°–35° C. for 1 to 12 hours. Under the preferred conditions, the alkylated product, 3, is formed to a large excess over its imidazole-N-regioisomer and is easily purified by crystallization or chromatography methods standard to the art of organic chemistry. The 4-chloro group is reduced by catalytic hydrogenation to convert 3 to 4. Preferred conditions for this reduction employ 5% to 10% Pd on carbon, a polar protic solvent such as methanol or ethanol, and a weak base such as NaOAc, KOAc, or LiOAc. Saponification of 4 with strong aqueous base such as NaOH, KOH, or LiOH using a water miscible organic cosolvent such as methanol, ethanol, or tetrahydrofuran gives the intermediate imidazole aldehyde, 5.

Intermediate hydantoins (Scheme II), 7, are prepared in a two-step process, starting from the appropriately N-substituted-glycine ester, 6. Treatment of 6 with a slight excess of dilute aqueous HCl and KNCO gives an intermediate urea that is cyclized to the hydantoin, 7, by treating with hot concentrated HCl. Furthermore compounds of the Type 6 may be treated with alkylisocyanates in methylene chloride at room temperature. The intermediate substituted ureas may then be cyclized in warm acid or base to afford hydantoins of the Type 1 bearing a $R_4$ substituent.

Condensation of imidazole-aldehyde intermediates 4 or 5 with hydantoin intermediates 7, as described in Scheme III, affords products of Formula I or Ia such as 10 and 11. The condensation is performed under strongly basic conditions in water or alcohol-water mixtures at 100°–120° C. Suitable bases include NaOH, KOH, LiOH, $(Me)_4NOH$, and the like, with $(Me)_4NOH$ preferred. Regioisomeric products 10 and 11 are separated by crystallization or chromatography methods standard to the art of organic chemistry.

An alternative method of condensation to give esters 12 and 13 offers greater control of regiochemistry about the double bond as shown in Scheme IV. Intermediate imidazole-aldehyde, 4, is condensed with the phosphonate-hydantoin, 9, which is prepared according to the published method of Meanwell, et al, *J.O.C.*, 56, 6879–6904 (1991) Depending upon the conditions used in the condensation, the ratio of Z to E isomers will vary. With alkoxides in alcoholic solvent a 1:1 ratio is observed. With 1,8-diazabicyclo[4.4.0] undec-7-ene (DBU), lithium chloride, and acetonitrile solvent, the Z isomer is formed in greater quantities than the E isomer with a Z:E ratio of $\geq 4:1$. Compounds 12 and 13 are compounds of Formula I or Ia and may be converted to Compounds 10 and 11, as shown in Scheme III which are also compounds of Formula I or Ia, by saponification of the ester group.

Furthermore Compounds 12 and 13 may be converted to compounds represented by Compound 16 by treatment with base in a suitable solvent and with an electrophile. Preferred conditions include treating Compound 12 with 5 equivalents of $K_2CO_3$ in DMF and an alkyl iodide.

In situations where the phosphonate 9 cannot be prepared an alternative procedure is available as outlined in Scheme V. The phosphonate 9a is prepared by treatment of diethyl 2,5-dioxo-4-imidazolidinone phosphonate with an electrophile and base in a suitable solvent. Preferred conditions include treating 9 with 5 equivalents $K_2CO_3$ in DMF and an alkyl iodide at room temperature and stirring for 4 to 16 hours. With less reactive electrophiles 9 can be treated with one equivalent of NaH in THF or DMF and the electrophile added at room temperature.

The phosphonate 9a is condensed with the intermediate aldehyde 4 (Scheme V) to give mixtures of the alkylidinene hydantoins 14 and 15. When DBU is used as a base in methylene chloride the Z isomer is formed predominantly. Compound 14 can be alkylated by treatment with base and a reactive electrophile. Typical condition include treating 14 with 5 equivalents of $K_2CO_3$, in DMF, and then adding the electrophile. Reactions proceed normally at room temperature. With less reactive electrophiles the reaction temperature may be elevated and additional quantities of electrophile added.

Ester saponification when $R_4$ and $R_1$ are not hydrogen is achieved by refluxing Compound 16 in acid; 2N HCl is preferable. Prolonged heating with concentrated HCl causes Z to E isomerization. Alternatively the t-butyl ester, Compound 17, is hydrolysed by treatment with trifluoroacetic acid.

Scheme VI represents an alternative procedure for preparing compounds such as 16. In this case the imidazole aldehyde 21 is condensed with a phosphonate hydantoin, such as 9A to afford the adduct 23. Equally applicable would be a hydantoin phosphonate containing a combination of $R_4$ and $R_1$ substituents. Compound 23 is treated with a reactive electrophile and a base, such as butyl iodide and $K_2CO_3$ respectively, to afford Compound 24. This intermediate then upon treatment with a reactive electrophile affords 16 with good regioselectivity. More specifically the hydantoin 9A is condensed with 21 in $CH_2CL_2$ using DBU as a base at room temperature. The Z-isomer is separated, alkylated at N-3, and treated with the trifluoromethanesulphonate derived from methyl 4-hydroxymethyl benzoate at $-78°$ C. in $CH_2Cl_2$. The reaction mixture is allowed to warm slowly to room temperature and the product 16 isolated upon removal of the protecting group.

A number of substituents are tolerated at position Y, as shown in Scheme VII. The condensation of a substituted phosphonate hydantoin with Compounds 24 through 28 is effected by the addition of base in an appropriate solvent. Typical conditions include the use of DBU in $CH_2Cl_2$ at room temperature as well as NaH in methanol. The reaction time is typically several hours with a greater portion of the Z isomer being formed when DBU is used as the base. Where the substrate contains an acidic hydrogen, as in Compound 29, a further equivalent of base is required for efficient conversion.

SCHEME I
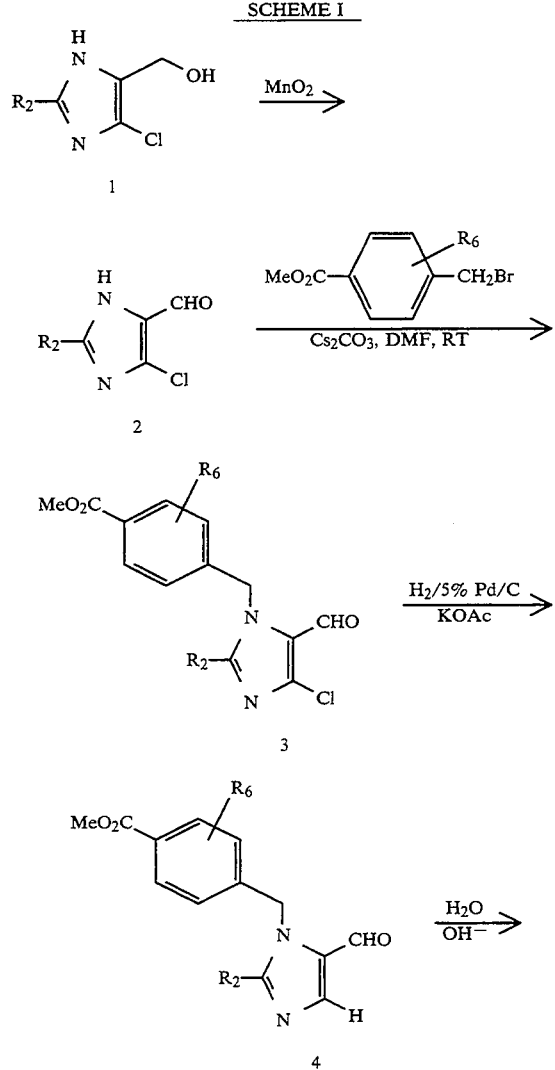
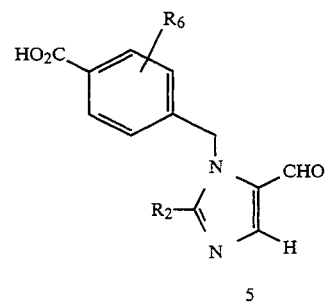
-continued
SCHEME I
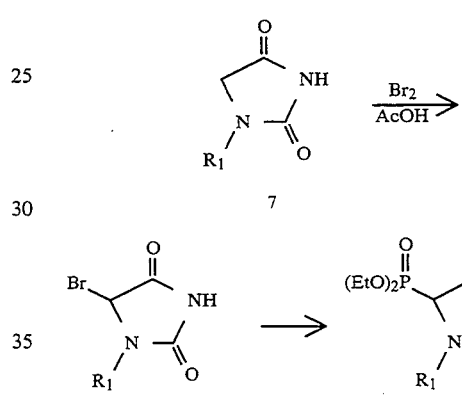
SCHEME II
1) 1.1 eq. HCl
   KNCO, H$_2$O
2) conc. HCl
   Δ
Meanwell, et al,
J.O.C. 56, 6897-6904 (1991).
(Report Compound where R$_1$ = H, CH$_3$)
SCHEME III
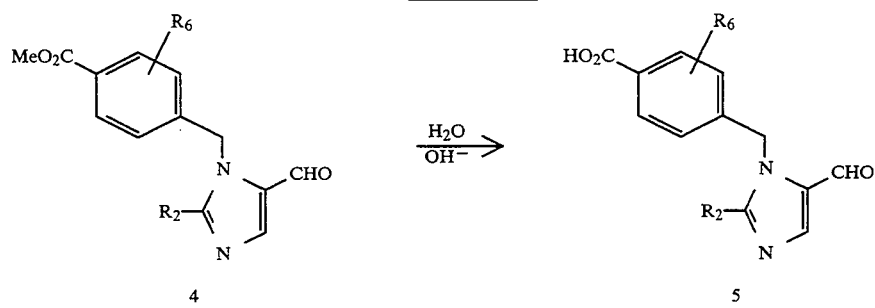

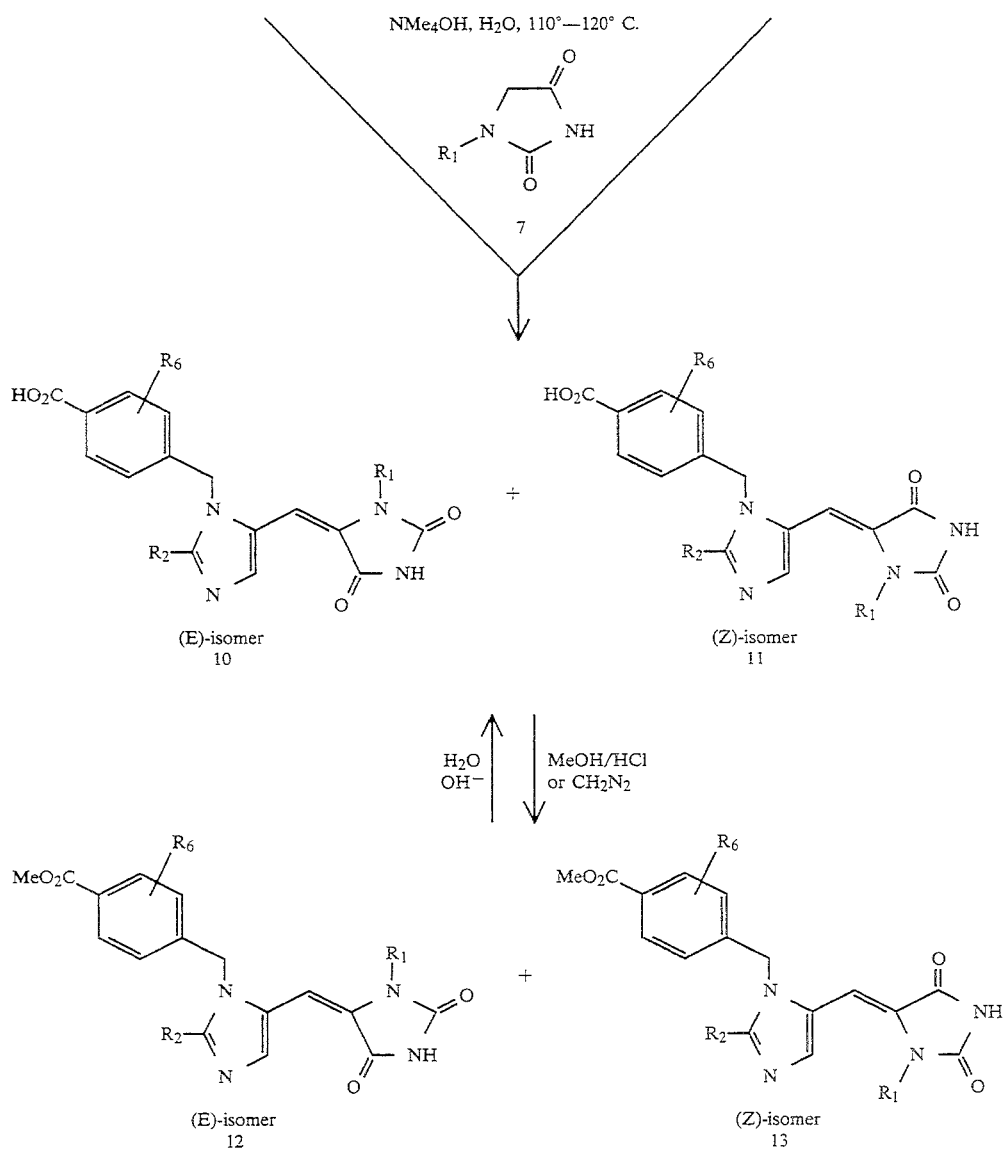
SCHEME IV
| | 12 | 13 |
|---|---|---|
| Condition A: MeOH, NaH | 30% Z, | 23% E |
| Condition B: LiCl, DBu, MeCN | 65% Z, | 14% E |
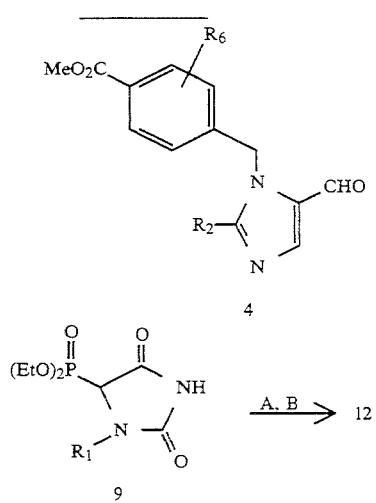
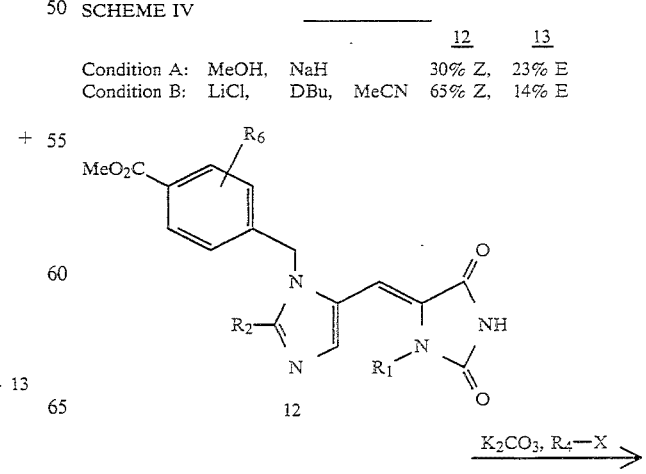

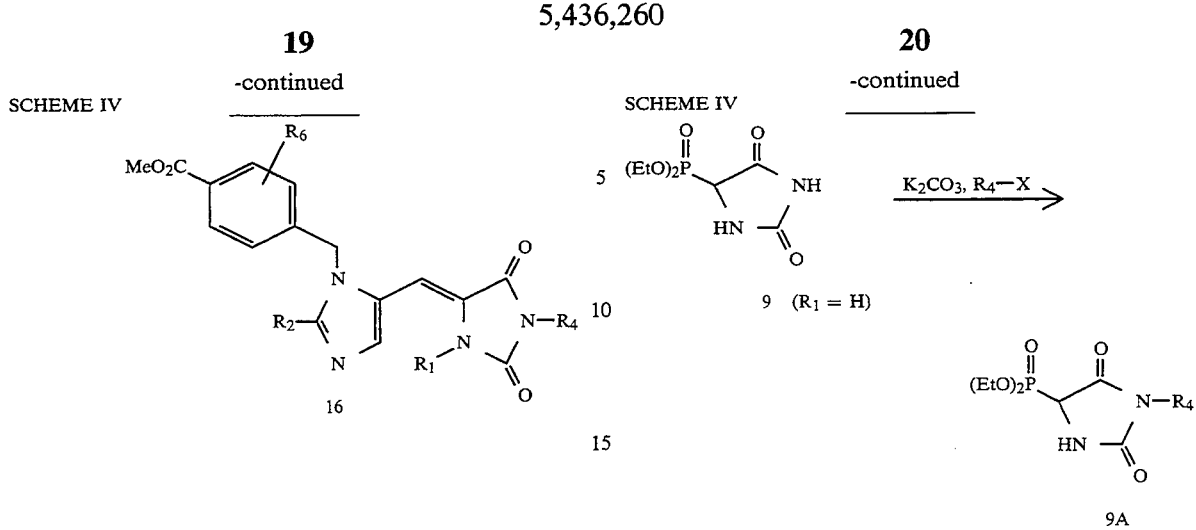
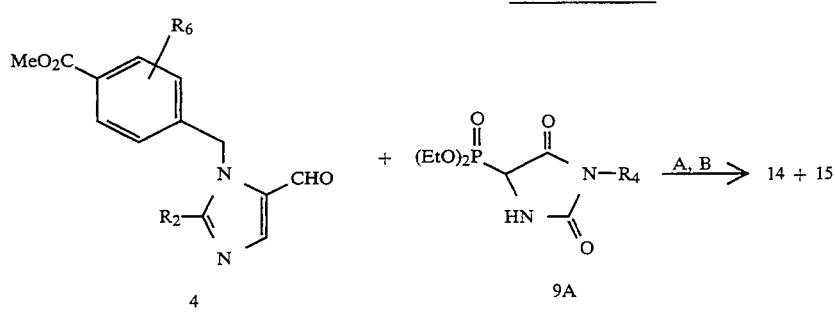
Condition A: MeOH, NaH
Condition B: DBU, CH₂Cl₂
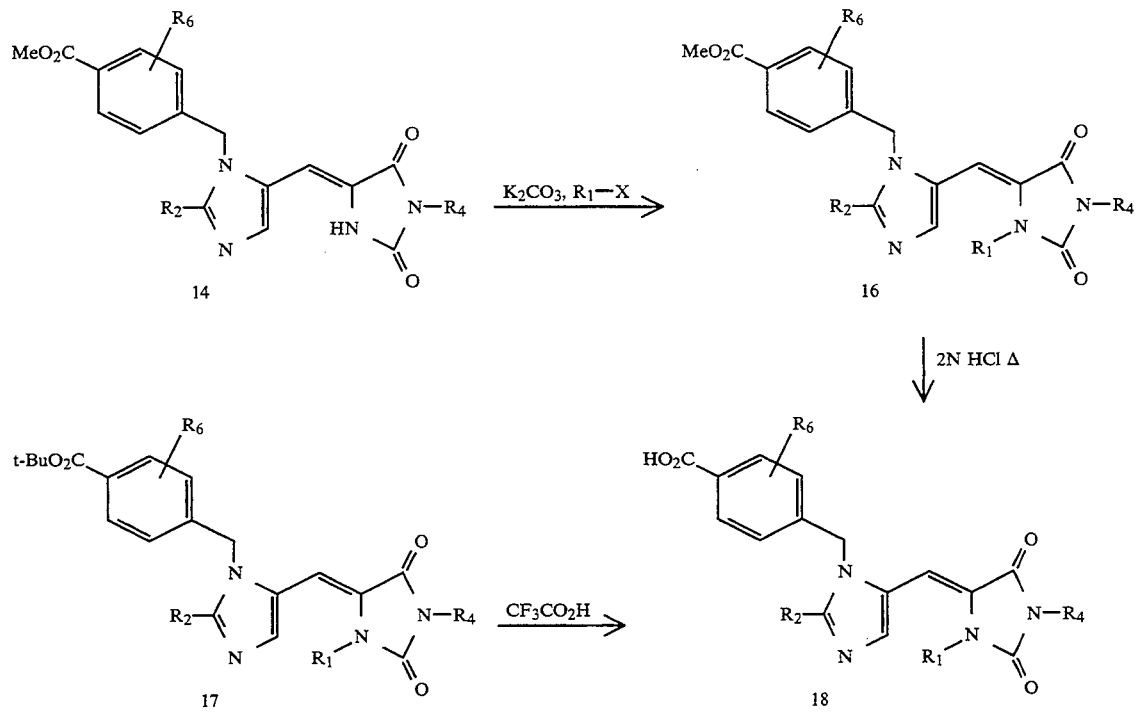

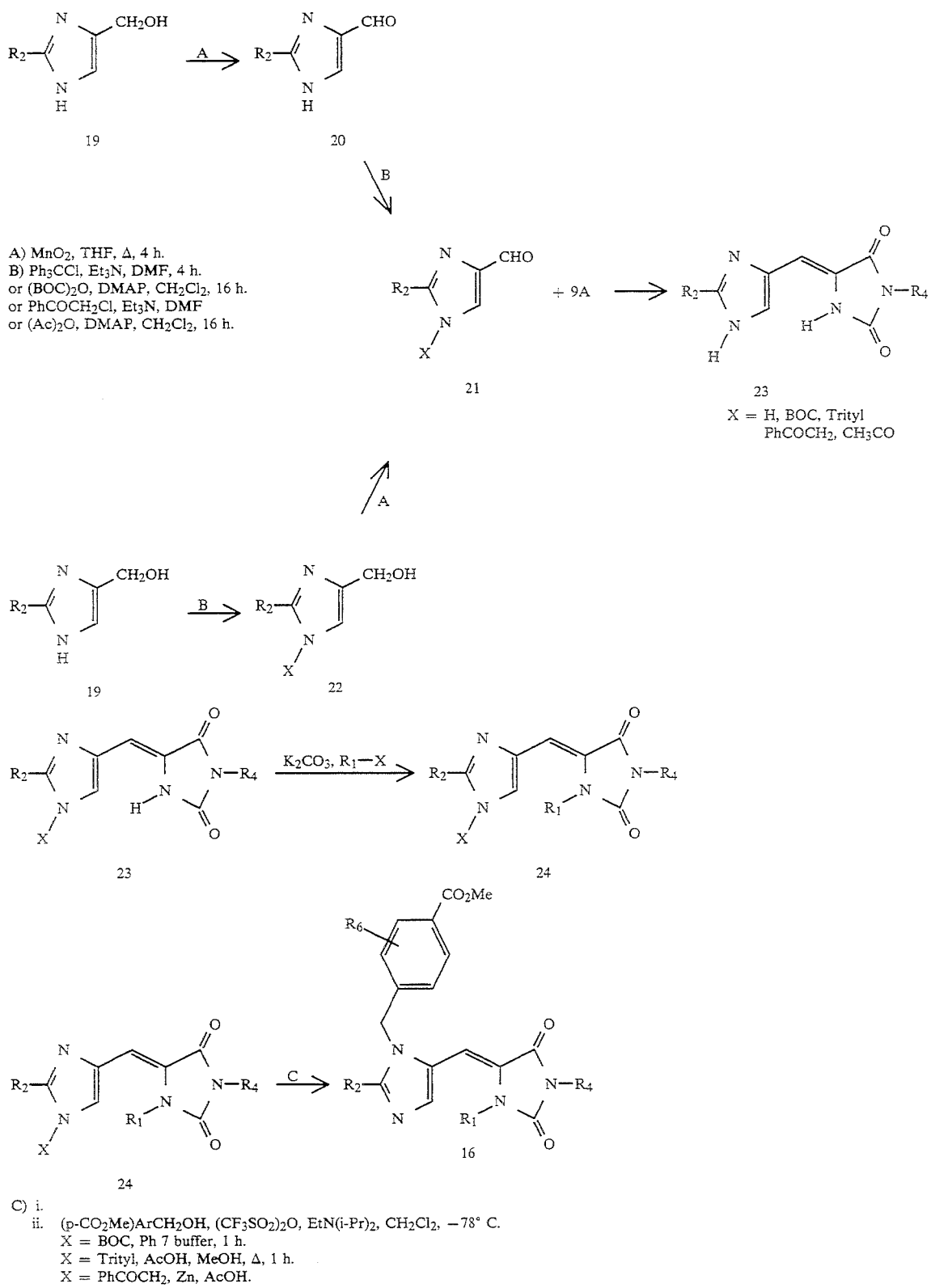

SCHEME VII

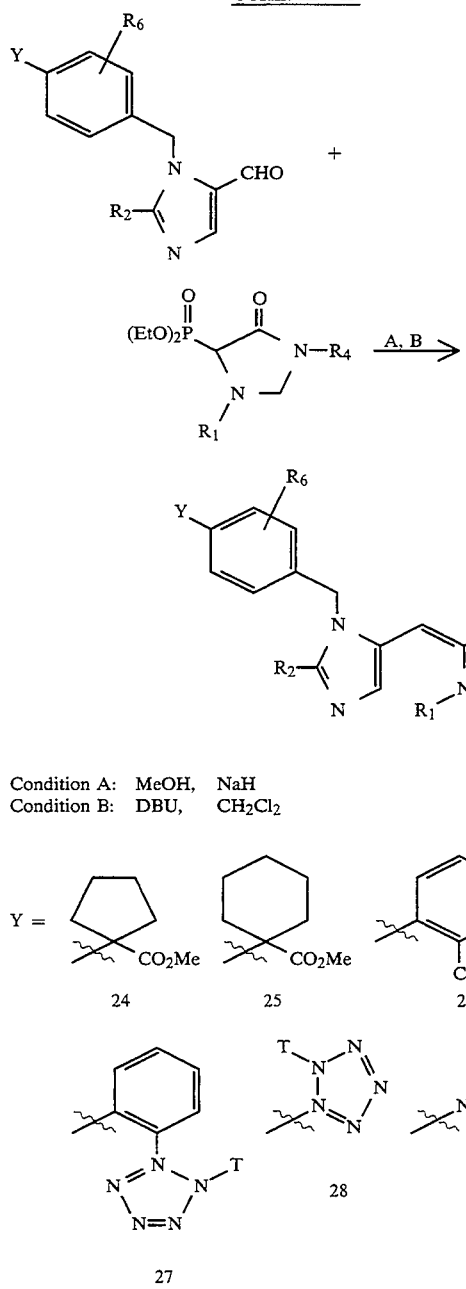

Condition A: MeOH, NaH
Condition B: DBU, CH₂Cl₂

T = Triphenylmethyl

The compounds of Formula I or Ia are antagonists of angiotensin II. Dudley, D. T., et al, *Molecular Pharmacology* 1990;38:370–377 reported the existence of 2 subclasses of angiotensin II binding sites in rabbit adrenal gland and uterus and in the rat liver which differ in their tissue distribution and affinity for various peptide and nonpeptide ligands. Thus, the compounds of Formula I or Ia were tested for their ability to inhibit [$^3$H]angiotensin II binding to rat liver membranes (AT$_1$ test) according to the methods described by Dudley, D. T., et al, *Molecular Pharmacology* 1990;38:370-7. Compounds of Formula I or Ia are active in the AT$_1$ test with IC$_{50}$ values as in Table I below.

It is well established that compounds which antagonize the effect of angiotensin II at the AT$_1$ receptor have value for treatment of hypertension and heart failure.

TABLE I

| Example | AT$_1$ IC$_{50}$ (nM) |
|---|---|
| 1a | 2.7 |
| 1b | 2.82 |
| 2a | 9.4 |
| 2b | 8.8 |
| 3a | 172 |
| 3b | 83.8 |
| 4a | 11.2 |
| 4b | 4.17 |
| 5 | 643 |
| 6a | 2.97 |
| 6b | 1.43 |
| 15a | 10.9 |
| 15b | 10.3 |
| 16a | 5.45 |
| 16b | 6.92 |
| 17a | 98.3 |
| 17b | 49.5 |
| 18 | 21 |
| 20a | 3.36 |
| 20b | 2.47 |
| 21a | 111 |
| 21b | 89.3 |
| 22 | 1.67 |
| 23 | 3.39 |
| 24 | 10.3 |
| 25 | 6.39 |
| 26a | 2.63 |
| 26b | 2.22 |
| 29 | >1000 |
| 32a | 178 |
| 32b | 1170 |
| 33 | 8.49 |
| 35 | 40.2 |
| 36 | 12.4 |
| 37 | 14.3 |
| 38 | 16.9 |
| 39 | 159 |
| 40 | 4.78 |
| 41 | 30.9 |
| 42 | 884 |
| 43 | 3.33 |
| 44 | 41.7 |
| 47 | >1000 |
| 48 | 14.6 |
| 49 | 9.48 |
| 50 | 26.6 |
| 51 | 5.33 |
| 53 | >1000 |
| 54 | 29.5 |
| 55 | 12.8 |
| 56 | 47.8 |
| 57 | 260 |
| 58 | 5.81 |
| 59 | 1.21 |
| 60 | 2.63 |
| 61 | 59.8 |
| 62 | 1.21 |
| 63 | 5.08 |
| 64 | 4.30 |
| 65 | 200 |
| 66 | 17.6 |
| 67 | 3.39 |
| 68 | 4.2 |
| 69 | 198 |
| 70 | 104 |
| 71a | 3.21 |
| 71b | 4.18 |
| 72 | 23.9 |
| 73 | 1.3 |
| 74 | 0.6 |
| 75 | 0.64 |
| 76a | 3.36 |
| 76b | 2.48 |
| 77 | 17.8 |
| 78 | 21.9 |
| 79 | 14.5 |
| 80 | 14.6 |
| 81 | 25.4 |

TABLE I-continued

| Example | AT₁ IC₅₀ (nM) |
|---|---|
| 82 | 7.96 |
| 83 | >1000 |
| 84 | 124 |
| 85 | 1.86 |
| 86 | 4.58 |
| 87a | 10.0 |
| 87b | 7.32 |
| 88a | 276 |
| 88b | 528 |
| 89 | 2.59 |
| 90 | 20.9 |
| 91 | 1.37 |
| 92 | 2.72 |
| 93 | 5.51 |
| 94 | 8.57 |
| 95 | 2.67 |
| 96a | 15.9 |
| 96b | 9.86 |
| 97a | 700 |
| 97b | 500 |
| 98 | 377 |
| 99 | 135 |
| 101 | 35.7 |
| 102 | >1000 |
| 103 | 120 |
| 104 | >1000 |
| 105 | 1.47 |
| 106 | 10.1 |
| 107 | 1450 |
| 108 | 8.47 |
| 109 | 11.1 |
| 110 | 2.47 |
| 111 | 70.0 |
| 112 | 6.44 |
| 113 | 18.3 |

Also, the compounds of Formula I or Ia were tested for functional activity in vitro. Thus, the compounds of the present invention were tested for their ability to antagonize angiotensin II induced contractions in rabbit aprotic rings according to the method described by Dudley D. T., et al, *Molecular Pharmacology* 90;38:370-7. The aforementioned test methods are incorporated herein by reference. Compounds of Formula I or Ia are active in this in vitro functional assay with IC₅₀ values ranging from $1 \times 10^{-10}$ to $1 \times 10^{-6}$ M.

Finally, the compounds of Formula I were tested in vivo for blood pressure lowering effects in renal hypertensive rats (2-kidney, 1-clip Goldblatt model) according to the method described by S. Sen, et al, in *Hypertension* 1979;1:427-34 and in *Clin. Soc.* 1979;57:53-62.

Illustrative of the in vivo antihypertensive activity for compounds of Formula I or Ia is the data for Example 1a. This compound lowers blood pressure by $\geq 50$ mm Hg and is efficacious for more than 24 hours with a single oral dose of 100 mg/kg in the renal hypertensive rat. Furthermore Example 73 lowers blood pressure by $\geq 30$ mm Hg and is efficacious for more than 24 hours with a single oral dose of 30 mg/kg in the renal hypertensive rat.

The compounds of the present invention can be prepared and administered in a wide variety of oral and parenteral dosage forms. It will be obvious to those skilled in the art that the following dosage forms may comprise as the active component, either a compound of Formula I or Ia or a corresponding pharmaceutically acceptable salt of a compound of Formula I or Ia.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% to 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient-sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg, preferably 0.5 mg to 100 mg, according to the particular application and the potency of the active component. The composition can, if desired, also contain other compatible therapeutic agents.

In therapeutic use as antihypertensive agents, the compounds utilized in the pharmaceutical method of this invention are administered at the initial dosage of about 0.1 mg to about 50 mg per kilogram daily. A daily dose range of about 0.5 mg to about 30 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following examples are illustrative of the final products of the instant invention as well as illustrative of intermediate compounds useful in preparing final compounds. They are not intended to limit the scope of the invention.

EXAMPLE 1a AND 1b

1a (E)-4-[[2-Butyl-5-[(3-butyl-2,5-dioxo-4-imidazolidinylidene)methyl]-1H-imidazol-1-yl]methyl]-benzoic acid A solution of 3.44 g (0.012 mole) of 2-butylol-(4-carboxybenzyl)-5-formylimidazole, 2.40 g (0.016 mole) of 1-butylhydantoin, 25.92 g (0.071 mole) of 25% tetramethylammonium hydroxide-in-methanol and 12 mL of water is heated with stirring with an oil bath (bath temperature 135°–150° C.), allowing the methanol to distill over. After ca. ½ hour, the pot temperature is ca. 115°–120° C. The temperature is maintained 115°–120° C. for 15 minutes. The reaction solution is cooled to 70° C. and 5.04 g (0.084 mole) of glacial acetic acid and then ca. 100 mL of water are added to precipitate the mixed cis (Z) and trans (E) isomers. Separation of isomers is accomplished by heating the mixture with 200 mL of methanol, cooling, and filtering off the least soluble (E) isomer. Recrystallization of the (E) isomer is effected by dissolution in 50% methanol-methylene chloride and concentration to remove methylene chloride. The separated pale yellow crystals are filtered; mp 287°–289° C.; tlc (2:10 MeOH—CHCl$_3$), 1 spot, Rf 0.4; nmr (DMSO-d$_6$), vinyl proton at δ 5.86 ppm; MS (CI) 425.1 (M$^+$ +1).

Analysis calculated for C$_{23}$H$_{28}$N$_4$O$_4$. 0.25H$_2$O: C, 64.39; H, 6.70; N, 13.06. Found: C, 64.36; H, 6.58; N, 12.87.

1b (Z)-4-[[2-Butyl-5-[(3-butyl-2,5-dioxo-4-imidazolidinylidene)methyl]-1H-imidazol-1-yl]methyl]-benzoic acid The more soluble (Z) isomer is isolated from the methanol filtrate of Example 1a. The filtrate is concentrated. The residue is heated with 2-propanol to the boiling point. The insolubles are filtered. Isopropyl ether is added to the filtrate to precipitate some mixed isomers. After filtration and concentration the residue is recrystallized from ethyl acetate-isopropyl ether to give pure (Z) isomer; mp 163°–165° C.; nmr (DMSO-d$_6$), single vinyl proton at δ 6.25 ppm; MS (CI) 425 (M$^+$ +1).

Analysis calculated for C$_{23}$H$_{28}$N$_4$O$_4$. 0.25H$_2$O: C, 64.39; H, 6.70; N, 13.06. Found: C, 64.36; H, 6.58; N, 12.87.

EXAMPLE 2a AND 2b

2a (E)-4-[[2-Butyl-5-[[2,5-dioxo-3-(3-methylbutyl)-4-imidazolidinylidene]methyl-1H-imidazole-1-yl]methyl]-benzoic acid This compound is prepared by a procedure similar to Example 1, starting from 1-isoamyl hydantoin. Pure (E) isomer is isolated as the least soluble isomer; mp 288°–290° C.; nmr (DMSO-d$_6$), vinyl proton at 5.84 ppm; MS (CI) 439 (M$^+$ +1).

Analysis calculated for C$_{24}$H$_{30}$N$_4$O$_4$: C, 65.73; H, 6.90; N, 12.78. Found: C, 65.42; H, 6.88; N, 12.86.

2b (Z)-4-[[2-Butyl-5-[[2,5-dioxo-3-(3-methylbutyl)-4-imidazolidinylidene[methyl]-1H-imidazole-1-yl]methyl]benzoic acid This isomer is isolated as the most soluble isomer in Example 2a. Its purity is 89.6% (Z) isomer and 8.2% (E) isomer as indicated by HPLC analysis and by integration of the vinyl proton of the major (Z) isomer at 6.25 ppm vs the minor (E) isomer at 5.84 ppm in the nmr (DMSO-d$_6$); mp 143°–146° C.

Analysis calculated for C$_{24}$H$_{30}$N$_4$O$_{43}$. 0.75H$_2$O: C, 63.77; H, 7.03; N, 12.40. Found: C, 63.79; H, 7.69; N, 12.76.

EXAMPLE 3a AND 3b

3a (E)-4-[[2-Butyl-5-[(2,5-dioxo-3-methyl-4-imidazolidinylidene)methyl ]-1H-imidazol-1-yl]methyl]benzoic acid This compound is prepared by a procedure similar to Example 1 except that the starting materials are the ester derivative, 2-butyl-1-(4-carbomethoxybenzyl)-5-formylimidazole, and 1-methylhydantoin. The crude mixed isomer products are purified and separated by silica gel column chromatography, eluting with 0.1:1.5:10 glacial acetic acid-methanol-chloroform. The "slow" moving material is the (E) isomer; tlc (0.1:2:10 acetic acid-methanol-chloroform system) 1 spot, Rf 0.5; mp 219°–221° C.; nmr (DMSO-d$_6$), vinyl proton at δ 5.96 ppm; MS (CI) 383 (M$^{39}$ +1).

Analysis calculated for C$_{20}$H$_{22}$N$_4$O$_4$. 0.25H$_2$O: C, 62.08; H, 5.86; N, 14.48. Found: C, 62.04; H, 5.96; N, 14.33.

3b (Z)-4-[[2-Butyl-5-[(2,5-dioxo-3-methyl-4-imidazolidinylidene)methyl ]-1H-imidazol-1-yl]methyl]benzoic acid The "fast" moving isomer isolated from chromatography in the above procedure, 3a, is identified as the pure (Z) isomer; tlc (0.1:2:10 acetic acid-methanol - chloroform system) , 1 spot, Rf 0.7; mp 248°–250° C.; nmr (DMSO-d$_6$), vinyl proton at δ 6.19 ppm; MS (CI) 383 (M$^+$ +1).

Analysis calculated for $C_{20}H_{22}N_4O_4 \cdot 0.25H_2O$: C, 61.37; H, 5.92; N, 14.32. Found: C, 61.09; H, 5.98; N, 14.26.

3b (Z)-4-[[2-Butyl-5-[(2,5-dioxo-3-(phenylmethyl)-4-imidazolidinylidene)methyl]-1H-imidazol-1-yl]methyl]benzoic acid This compound is prepared by a procedure similar to Example 3 starting with 1-benzylhydantoin. Pure (E) isomer is isolated as the compound that is least soluble in methanol; mp 297°-298° C.; nmr (DMSO-d$_6$) single vinyl proton at δ 5.90 ppm; MS (CI) 459 (M$^+$ +1).

Analysis calculated for $C_{26}H_{26}N_4O_4 \cdot 0.5H_2O$: C, 66.79; H, 5.82; N, 11.99. Found: C, 66.71; H, 5.94; N, 12.04.

4b (Z)-[[2-Butyl-5-[2,5-dioxo-3-(phenylmethyl)-4-imidazolidinylidene)methyl]-1H-imidazole-1-yl]methyl]benzoic acid This isomer (Z) is isolated as the most soluble isomer in the above Example 4a. Its purity is estimated to be 85% (Z) and 15% (E) isomer as indicated by the ratio of the vinyl proton integrations in the nmr (DMSO-d$_6$); vinyl proton for (Z) isomer at δ 6.05 ppm; MS (CI) 459 (M$^+$ +1).

Analysis calculated for $C_{26}H_{26}N_4O_4 \cdot 0.75H_2O$: C, 66.15; H, 5.88; N, 11.87. Found: C, 65.96; H, 5.87; N, 11.79.

EXAMPLE 5

(E)-4-[[2-Butyl-5-[(2,5-dioxo-3-phenyl-4-imidazol-imidazolidinylidene)methyl]-1H-imidazole-1-yl]methyl]benzoic acid This compound is prepared by a procedure similar to Example 1. The compound least soluble in 2-propanol is identified as the pure (E)-isomer; mp 286°-290° C.; tlc (1: 10 methanol - chloroform) 1 spot, Rf 0.2; nmr (DMSO-d$_6$) single vinyl proton at δ 5.89 ppm; MS (CI) 445 (M$^+$ +1).

Analysis calculated for $C_{25}H_{24}N_4O_4 \cdot H_2O$: C, 64.92; H, 5.67; N, 12.11. Found: C, 65.41; H, 5.47; N, 12.23.

EXAMPLE 6a AND 6b

6a (E)-4-[[2-Butyl-5-[(2,5-dioxo-3-phenyl-4-imidazolidinylidene)methyl]-1H-imidazole-1-yl]methyl]benzoic acid This compound is prepared by a procedure similar to Example 3 starting with 1-(2-thienylmethyl)-hydantoin. Pure (E) isomer is isolated as the compound that is least soluble in methanol; mp 297°-299° C.; tlc (0.1:5:20 acetic acid-methanol-chloroform), 1 spot, Rf 0.6; nmr (DMSO-d$_6$) single vinyl proton at δ 6.13 ppm; MS (CI) 465 (M$^+$ +1).

Analysis calculated for $C_{24}H_{24}N_4O_4S \cdot 0.25H_2O$: C, 61.32; H, 5.47; N, 11.92. Found: C, 61.30; H, 5.21; N, 11.95.

6b (Z) -4-[[2-Butyl-5-[[2,5-dioxo-3-((2-thienyl)methyl)-4-imidazolidinylidene]-methyl-1H-imidazole-1-yl]methyl]benzoic acid This isomer (Z) is isolated as the most soluble isomer in the above Example 6a. It is recrystallized from ethyl acetate to give pure (Z) isomer; mp 140°-145° C.; tlc (0.1:5:20 acetic acid-methanol-chloroform), 1 spot, Rf 0.8 nmr (DMSO-d$_6$), single vinyl proton at 6.16 ppm. MS (CI) 465 (M$^+$ +1).

Analysis calculated for $C_{24}H_{24}N_4O_4S \cdot 0.25 Cp_4H_8O_2$: C, 61.70; H, 5.39; N, 11.52. Found: C, 61.43; H, 5.45; N, 11.69.

EXAMPLE 7

2-Butyl-1-(4-carboxybenzyl)-5-formylimidazole

A solution of 3.00 g (0.01 mole) of 2-butyl-1-(4-carbomethoxybenzyl)-5-formylimidazole in 100 mL of methanol and 15 mL (0.03 mole) of 2 N sodium hydroxide is heated to the boiling point, allowing methanol to distill over. After 1 hour, the pot temperature is 85° C. Water (30 mL) and then 30 mL of 1 N hydrochloric acid are added to precipitate a gum. This crystallized; wt 2.40 g. Recrystallization from ethyl acetate gives 1.30 g of product; mp 146°-148° C.; tlc (1:10 MeOH-CHCl$_3$), 1 spot, Rf 0.3; MS (CI) 287 (M$^+$ +1).

Analysis calculated for $C_{16}H_{18}N_2O_3$: C, 67.12; H, 6.34; N, 9.78. Found: C, 67.14; H, 6.28; N, 9.72.

EXAMPLE 8

2-Butyl-1-(4-carbomethyoxybenzyl)-5-formylimidazole (*J. Med. Chem.* 1991;34:1514–17)

A solution of 1.00 g (0.003 mole) of 2-butyl-1-(4-carbomethoxybenzyl)-4-chloro-5-formylimidazole in 75 mL of methanol is reduced at low pressure with hydrogen and 0.30 g of 5% Pd/carbon in the presence of 0.30 g of potassium acetate to give product; mp 62°-64° C.; tlc (1:1 hexane-ethyl acetate) 1 spot, Rf 0.2; MS (CI) 301 (M$^+$ +1) .

EXAMPLE 9

2-Butyl-1-(4-carbomethoxybenzyl)-4-chloro-5-formylimidazole (*J. Med. Chem.* 1991;34:1514–17).

A solution of 17.50 g (0.098 mole) of 2-butyl-4-chloro-5-formylimidazole (U.S. Pat. No. 4,355,040) in 855 mL of DMF is treated with 91.65 g (0.28 mole) of cesium carbonate and the mixture is stirred at room temperature for 10 minutes. A solution of 22.56 g (0.099 mole) of methyl 4-(bromomethyl)benzoate in 270 mL of DMF is added and the mixture is stirred for 4 hours at room temperature. The cesium salts are filtered and the DMF filtrate is concentrated at reduced pressure. The crude product is purified by silica gel chromatography, eluting with methylene chloride, and then 1:7 ethyl acetate/methylene chloride, obtaining 23.16 g (74%) of pure product; mp 96°-98° C.; tlc (1:1 hexane-ethyl acetate), 1 spot, Rf 0.7; MS (CI), 335 (M$^+$).

EXAMPLE 10

1-Butyl hydantoin (*Org. Mass. Spectrometry* 1971;5:551–3).

A quantity of 24.4 g (0.30 mole) of potassium cyanate is added portionwise, at room temperature, to a stirred solution of 31.80 g (0.20 mole) of ethyl N-butylglycinate in 220 mL (0.22 mole) of 1 N hydrochloric acid. The solution is warmed to ca. 90° C. (at ca. 50° C. an oil separates). After 10 minutes at 90° C., concentrated hydrochloric acid (250 mL) is cautiously added over 2 minutes and the resulting solution is heated at 90°100° C. for ½ hour. The solution is concentrated at reduced pressure to dryness. The last amounts of water are chased by addition and removal of 3×100 mL of absolute ethanol. The residue is extracted with 400 mL 50% ethanol-methylene chloride. The inorganics are filtered and the filtrate is concentrated to dryness. Trituration of the residue with 100 mL of water and filtration gives pure 1-butylhydantoin in 68% yield; mp 90°92° C.; MS (EI) 156.1 (M+).

Analysis calculated for $C_7H_{12}N_2O_2$: C, 53.83; H, 7.69; N, 17.99. Found: C, 53.88; H, 7.80; N, 17.85.

EXAMPLE 11

1-Isoamyl hydantoin

This compound is prepared by the procedure outlined in Example 10; mp 84°–85° C.; MS (EI) 170 (M+).

Analysis calculated for $C_7H_{12}N_2O_2$: C, 56.45; H, 8.29; N, 16.46. Found: C, 56.84; H, 8.38; N, 16.34.

EXAMPLE 12

1-Benzylhydantoin

This compound is prepared by the procedure outlined in Example 10; mp 139°–140° C.; MS (EI) 190 (M+).

Analysis calculated for $C_{10}H_{10}N_2O_2 \cdot 0.1H_2O$: C, 62.55; H, 5.35; N, 14.59. Found: C, 62.48; H, 5.56; N, 14.36.

EXAMPLE 13

1-(2-Thienylmethyl)hydantoin

This compound is prepared by a procedure similar to that in Example 10; mp 140°–142° C.; MS (EI) 196 (M+).

Analysis calculated for $C_8H_8N_2O_2S$: C, 48.97; H, 4.11; N, 14.28. Found: C, 49.00; H, 4.05; N, 14.19.

EXAMPLE 14

1-Phenyl hydantoin

This compound is prepared by a procedure similar to that in Example 10; mp 193°–194° C.; MS (EI) 176 (M+). Analysis calculated for $C_9H_8N_2O_2$:
C, 61.36; H, 4.58; N, 15.90.
Found: C, 61.38; H, 4.52; N, 15.92.

EXAMPLE 15a AND 15b 15a (Condition A)

(E)-4-[[2-Butyl-5-[(3-butyl-2,5-dioxo-4-imidazolidinylidene)methyl]-1H-imidazole-1-yl]methyl]benzoic acid, methyl ester To a mixture of 1-butyl-2,4-dioxoimidazolidine-5-phosphonate (680 mg, 2.41 mmol) and 2-butyl-1-(4-carbomethoxybenzyl)-5-formylimidazole (490 1.67 mmol) in methanol (15 mL) is cautiously added sodium hydride 80% dispersion in oil. The mixture is stirred for 1 hour at room temperature. Acetic acid (0.30 mL, 5.24 mmol) is added dropwise which causes the yellow solution to lighten. The mixture is evaporated in vacuo. This mixture is extracted into dichloromethane, washed with water, and dried over sodium sulfate. NMR analysis of this reaction mixture indicates a 1:1 mixture of E- and Z-isomers. Chromatography on silica gel eluting with 97 CHCl₃ 3 MeOH affords pure Z-and then E-isomer. NMR on (E) isomer: (CDCl₃) single vinyl proton at δ 5.60 ppm. E-isomer.

Analysis calculated for $C_{24}H_{30}N_4O_4$: C, 65.73; H, 6.90; N, 12.78. Found: C, 65.50; H, 6.87; N, 12.66. MS (EI) 438.

15b (Conditions A)

(Z)-4-[[2-Butyl-5-[(3-butyl-2,5-dioxo-4-imidazolidinylidene)methyl]-1H-imidazole-1-yl]methyl]benzoic acid, methyl ester The Z-isomer is isolated as described in 15a; NMR (CDCl₃), single vinyl proton at δ 6.32 ppm. Analysis calculated for $C_{24}H_{30}N_4O_4$:
C, 65.73; H, 6.90; N, 12.78.
Found: C, 65.54; H, 6.85; N, 12.53.

EXAMPLE 15a AND 15b (Conditions B)

To diethyl 1-butyl-2,4-dioxoimidazolidine-5-phosphonate (590 mg, 2.1 mmol) in acetonitrile (5 mL) is added lithium chloride (79 mg, 1.86 mmol) and then 1,8-diazabicyclo[5.4.0] undec-7-ene (277 μL, 1.85 mmol). A yellow solution forms within 5 minutes. 2-Butyl-1-(4-carbomethoxybenzyl)-5-formylimidazole (461 mg, 1.54 mmol) is added. After 10 minutes, lithium chloride (79 mg, 1.86 mmol) and 1,8-diazabicyclo[5.4.0] undec-7-ene (277 μL, 1.85 mmol) are again added. A precipitate develops. Upon stirring at room temperature for 16 hours, a wine-red solution remains. This mixture is concentrated in vacuo and applied directly to a silica gel column. Eluting with 95 CHCl₃ 5 MeOH affords, in order of increasing polarity, the Z-isomer (441 mg, 65%) and then the E-isomer (96 mg, 14%) which had identical spectral characteristics as the above compounds produced by Conditions A.

EXAMPLE 16a AND 16b

16a (e)-4-[[2-Butyl-5-[[2,5-dioxo-3-((2-thienyl)methyl)-4-imidazolidinylidene[methyl]-1H-imidazole-1-yl]methyl]benzoic acid, methyl ester A mixture of the (E) carboxylic acid derivative from Example 6a and 30 mL of methanol is treated with a stream of hydrogen chloride gas, allowing the temperature to rise. The resulting solution is allowed to stand at room temperature overnight. The solution is concentrated to ca. ½ volume and excess saturated NaHCO₃ solution is added to precipitate pure crystalline product; mp 209°–210° C.; tlc (1:10 MeOH-CHCl₃) 1 spot, Rf 0.5; MS (CI) 479 (M++1).

Analysis calculated for $C_{25}H_{26}N_4O_2S \cdot 0.1H_2O$: C, 61.89; H, 5.44; N, 11.55. Found: C, 62.20; H, 5.36; N, 11.43.

16b (Z)-4-[[2-Butyl-5-[[2,5-dioxo-3-((2-thienyl)methyl)-4-imidazolidinylidene]methyl]-1H-imidazole-1-yl]methyl]benzoic acid, methyl ester This compound is prepared as in Example 16a from the (Z) carboxylic and derivative from Example 6b; mp 164°–165° C.; tlc (1:10 MeOH-CHCl₃) 1 spot, Rf 0.6; MS (CI) 479 (M++1).

Analysis calculated for $C_{25}H_{26}N_4O_4S$: C, 62.74; H, 5.48; N, 11.71. Found: C, 63.00; H, 5.23; N, 11.47.

17a (E)-4-[[2-Butyl-5-[[2,5-dioxo-3-(4-hydroxybutyl)-4-imidazolidinylidene]ethyl]-1H-imidazole-1-yl]methyl]-benzoic acid, methyl ester This compound is prepared as with the butyl hydantoin derivatives in Example 1a and then esterified with diazomethane. E-and Z-isomers are separated by flash chromatography on silica gel (CHCl$_3$-MeOH, 96:4); mp of (E) isomer 167°–170° C.; NMR (CDCl$_3$) single vinyl proton at δ 5.62; MS (CI) 455 (M$^+$+1).

Analysis calculated for C$_{24}$H$_{30}$N$_4$O$_5$: C, 63.42; H, 6.65; N, 12.33. Found: C, 63.25; H, 6.67; N, 12.22.

17b (Z)-4-[[2-Butyl-5-[[2,5-dioxo-3-(4-hydroxybutyl)-4-imidazolidinylidene]methyl]-1-H-imidazole-1-yl]methyl]benzoic acid, methyl ester This compound is isolated from the chromatography in the above Example 17a; mp 76°–86° C.; MS (CI) 455 (M$^+$+1).

Analysis calculated for C$_{24}$H$_{30}$N$_4$O$_5$. 0.1CH$_3$OH: C, 63.24; H, 6.69; N, 12.24. Found: C, 63.65; H, 6.91; N, 11.83.

EXAMPLE 18

(E)-4-[[2-Propyl-5-[[3-butyl-1-methyl-2,5-dioxo-4-imidazolidinylidene)-methyl ]-benzoic acid, methyl ester A solution of 0,082 g (0.17 mmol) of the 2-propyl (E) isomer hydrochloride prepared similarly to Example 15a, and 0.024 g (0.17 mmol) of methyl iodide in 0.50 mL of DMF is cooled in an ice bath. With stirring, 0.50 g anhydrous potassium carbonate is added. The mixture is removed from the ice bath and stirred at room temperature for 1 hour. To complete the reaction, another 0.024 g of methyl iodide is added and the mixture is stirred for another 1 hour. Water (5 mL) is added to precipitate crude product. Recrystallization from ether gives pure N-methyl derivative; mp 113°–114° C.; tlc (1:10 MeOH-CHCl$_3$) 1 spot,Rf 0.6; MS (CI) 439 (M$^+$+1).

EXAMPLE 19

3-Butyl-2,5-dioxo-imidazolidene-4-phosphonic acid, diethyl ester

To a solution of 1-butylhydantoin (3.5 g, 0.022 moles) in glacial acetic acid (20 mL) at 90°–100° C. is added bromine (1.22 mL, 0.024 moles) in acetic acid (10 mL) batchwise; at such a rate that the initial orange-red color discharges to a yellowish solution. This addition rate takes about 5 minutes. The solution is stirred at 90°–100° C. for a further 60 minutes. 1H Analysis of the reaction mixture indicates incomplete conversion. A further amount of bromine (0.3 mL) is added and the solution is refluxed for 1 hour and then stirred for 16 hours at room temperature. Concentration in vacuo from toluene affords a viscous oil (5.5 g). This oil is dissolved in diethyl ether and treated with triethyl phosphite (3.7 mL, 0.022 moles). The solution is stirred for 16 hours at room temperature. The mixture is evaporated in vacuo and the required product isolated by chromatography on silica gel, eluting with 95 CHCl$_3$-5 MeOH. This viscous oil contains small amounts of an impurity but is sufficiently pure to be used in subsequent reactions; NMR (1H, CDCl$_3$) δ 8.86 (1H, br s), 4.30 (7H, m), 3.86 (1H, m), 3.38 (1H, m), 1.60 (2H, m), 1.35 (9H, m), 0.89 (3H, m); MS (CI) 293.

EXAMPLES 20a AND 20b

20a

E-4-[[2-butyl-5-[[3-[(4-chlorophenyl)methyl]-2,5-dioxo-4-imidazolidinylidene]methyl]-1H-imidazol-1-yl]methyl]benzoic acid This compound is prepared by a procedure similar to example 1, starting from 1-[(4-chlorophenyl)methyl]-2,4-imidazolidinedione. Pure E isomer is isolated as the least soluble isomer in 2-propanol; mp 248°–250° C.; nmr (DMSO-d$_6$), vinyl proton at 5.89 ppm; MS (CI) 493 (m+).

Anal. Calcd. for C$_{26}$H$_{25}$ClN$_4$O$_4$.0.25 H$_2$O: C, 62.77; H, 5.17; N, 11.26 Found: C, 62.84; H, 5.08; N, 11.12

20b

Z-4-[[2-butyl-5-[[3-[(4-chlorophenyl)methyl]-2,5-dioxo-4-imidazolidinylidene]methyl]-1H-imidazol-1-yl]methyl]benzoic acid This compound is isolated as the most soluble isomer in Example 20a. It is purified by silica gel chromatography, eluting with 1: 5: 40 acetic acid-methanol-chloroform to give pure faster moving Z isomer; mp 225°–227° C.; nmr (DMSO-d$_6$), vinyl proton at 6.09 ppm; MS (CI) 493 (m+).

Anal. Calcd. for C$_{26}$H$_{25}$ClN$_4$O$_4$: C, 63.35; H, 5.11; N, 11.37 Found: C, 63.01; H, 5.09; N, 11.20

EXAMPLES 21a AND 21b

21a

E-4-[[2-butyl-5-[[3,4-dimethyoxyethyl)methyl]-2,5-dioxo-4-imidazolidinylidene]methyl]-1H-imidazol-1-yl]methyl]benzoic acid This compound is prepared by a procedure similar to Example 1 starting from 1-[(3,4-dimethyoxyethyl) methyl]-2,4-imidazolidinedione. Pure E isomer is isolated as the least soluble isomer in methanol; mp 266°–267° C.; NMR (DMSO-d$_6$) , vinyl proton at 5.97 ppm; MS (CI) , 519 (m$^+$+1).

Anal. Calcd. for C$_{28}$H$_{30}$N$_4$O$_6$: C, 64.85; H, 5.83; N, 10.80 Found: C, 64.82; H, 6.03; N, 10.93

21b

Z-4-[[2-butyl-5-[[3-(3,4-dimethoxyphenyl)methyl]-2,5-dioxo-4-imidazolidinylidene]methyl]-1H-imidazol-1-yl]methyl]benzoic acid This compound is isolated as the most soluble isomer in Example 21a. It is purified by recrystallization from ethyl acetate; mp 225°–226° C.; NMR (DMSO-d$_6$), vinyl proton at 6.14 ppm; MS (CI) 519 (m$^+$+1) .

Anal. Calcd. for C$_{28}$H$_{30}$N$_4$O$_6$: C, 64.85; H, 5.83; N, 10.80 Found: C, 64.62; H, 5.94 N, 10.73

EXAMPLE 22

Methyl Z-4-[[-2-butyl-5-[(1,3-dibutyl-2,5-dioxo-4-imidazolidinylidene)methyl ]-1H-imidazol-1-yl]methyl]benzoate monohydrochloride A mixture of 0.220 g (10.5 retool) of the Z-isomer NH hydantoin from Example 15b, 0.50 mL of DMF, 0.20 g of powdered potassium carbonate and 0.101 g (0.5 mmol) of butyl iodide is stirred at 25° C. for 2 hours.

Crushed ice is added to precipitate the gummy product. The aqueous DMF is decantered and the gum is extracted into 15 mL of ether. The ether solution is washed with water, dried ($K_2CO_3$) and treated with hydrogen chloride to precipitate a gummy hydrochloride salt which crystallizes on inducement. Recrystallization from 2-propanol-ether gives pure product; mp 153°–155° C.; NMR (DMSO-$d_6$), vinyl proton at 6.26 ppm; MS (CI) 495.5 ($m^+ +1$).

Anal. Calcd. for $C_{28}H_{38}N_4O_4$ HCl: C, 63.32; H, 7.40; N, 10.55 Found: C, 63.51; H, 7.58; N, 10.36

EXAMPLE 23

Methyl Z-4-[[2-butyl-5-[[1-butyl-2,5-dioxo-3-(2-thienylmethyl)-4-imidazolidinylidene]methyl]-1H-imidazol-1-yl]methyl]benzoate monohydrochloride This compound is prepared from the NH hydantoin derivative of Example 16b by an alkylation procedure similar to that in Example 22; mp of hydrochloride salt, 185°–187° C.;
NMR (DMSO-$d_6$), vinyl proton at 6.07 ppm; MS (CI) 535 ($m^+ +1$).

Anal. Calcd. for $C_{29}H_{34}N_4O_4S$ HCl: C, 60.99; H, 6.18; N, 9.81 Found: C, 60.69; H, 6.16; N, 9.69

EXAMPLE 24

Methyl E-4-[[2-butyl-5-[[1-butyl-2,5-dioxo-3-(2-thienylmethyl)-4-imidazolidinylidene]methyl]-1H-imidazol-1-yl]methyl]benzoate monohydrochloride This compound is prepared form the NH hydantoin derivative of Example 16a by an alkylation procedure similar to that in Example 22; mp 209°–211° C.;
NMR (DMSO-$d_6$), vinyl proton at 6.27 ppm; MS (CI) 535 ($m^+ +1$).

Anal. Calcd. for $C_{29}H_{34}N_4O_4$ HCl: C, 60.99; H, 6.18; N, 9.81 Found: C, 60.69; H, 6.14; N, 9.53

EXAMPLE 25

Z-4-[[2-butyl-5-[[1-butyl-2,5-dioxo-3-(2-thienyl)methyl]-4-imidazolidinylidene]methyl]-1H-imidazol-1-yl]methyl]benzoic acid A solution of 0.174 g (0.30 mmol) of the ester from Example 23, 4 mL of methanol and 2 mL of 3N hydrochloric acid is maintained at reflux for 3 days. The volatiles are removed at reduced pressure and the crude product is chromatographed eluting with 5% methanol-chloroform. The product is isolated as a glassy foam; tlc (1:10 methanol chloroform) one spot, Rf 0.4;
NMR (DMSO-$d_6$), vinyl proton at 6.28 ppm; MS (CI) 521 ($m^+ +1$).

Anal. Calcd. for $C_{28}H_{32}N_4O_4S$: C, 64.59; H, 6.20; N, 10.76 Found: C, 64.60; H, 6.19; N, 10.33

EXAMPLES 26a AND 26b

26a

E-1-[4-[[2-butyl-5-[[2,5-dioxo-3-(2-thienylmethyl)-4-imidazolidinylidene]methyl]-1H-imidazol-1-yl]methyl]phenyl]cyclopentanecarboxylic acid This compound is prepared by a procedure similar to that in Example 1. The product is isolated as the most soluble isomer in methanol in 70% purity nmr (DMSO-$d_6$) benzyl $CH_2$ at 5.36 ppm (major E isomer). The impurity is the minor Z isomer with benzyl $CH_2$ at 5.08 ppm; MS (CI) 533 ($m^+ +1$).

Anal. Calcd. for $C_{29}H_{32}N_4O_4S$: C, 65.39; H, 6.06; N, 10.52 Found: C, 65.01; H, 5.99; N, 10.41

26b

Z-1-[4-[[2-butyl-5-[[2,5-dioxo-3-(2-thienylmethyl)-4-imidazolidinylidene]methyl]-1H-imidazol-1-yl]methyl]phenyl]cyclopentanecarboxylic acid This compound is isolated pure in Example 26a as the least soluble isomer in methanol; mp 261°–263° C.; NMR (DMSO-$d_6$) benzyl $CH_2$ at 5.08 ppm; MS (CI) 533 ($m^+ +1$).

Anal. Calcd. for $C_{29}H_{32}N_4O_4$ S: C, 65.39; H, 6.06; N, 10.52 Found: C, 65.14; H, 6.07; N, 10.35

EXAMPLE 27

1-[(3,4-Dimethoxyphenyl)methyl]-2,4-imidazolidinedione

This compound is prepared by a procedure similar to that in Example 10; mp 130°–132° C. C; MS (CI) 250 ($M^+$)

Anal. Calcd. for $C_{12}H_{14}N_2O_4$: C, 57.59; H, 5.64; N, 11.19 Found: C, 57.46; H, 5.54; N, 11.19

EXAMPLE 28

1-[(4-Chlorophenyl)methyl]-2,4-imidazolidinedione

This compound is prepared by a procedure similar to that in Example 10; mp 169°–171° C.; MS (EI) 224 ($M^+$) Anal. Calcd. for $C_{10}H_9ClN_2O_2$: C, 53.47; H, 4.04; N, 12.47

EXAMPLE 29

Methyl 4-[[2-butyl-5-[(3-butyl-2,5-dioxo-4-imidazolidinyl)hydroxymethyl]-1H-imidazol-1-yl]methyl]benzoate To a suspension of 1-butyl-2,4-imidazolidinedione (0.600 g, 4.17 mmol) in THF (15 ml) at $-78°$ C. is added lithium diisopropylamide (2.1 equiv.). After stirring for 20 minutes a solution of methyl 4-[(2-butyl-5-formyl-1H-imidazol-1-yl)methyl]benzoate (1.250 g, 4.17 mmol) in THF (10 mL) is added dropwise over 10 minutes to form an orange solution. This solution is stirred for a further 20 minutes at $-78°$ C. and is then added to aqueous ammonium chloride. This mixture is evaporated in vacuo and then extracted into ethyl acetate. After washing with water and then brine the solution is dried over $Na_2SO_4$. Evaporation in vacuo and chromatography, eluant 5% methanol in chloroform, affords the required product. Recrystallized from ethyl acetate containing traces of methanol.

Anal. Calcd. for $C_{24}H_{31}N_4O_5$:C, 63.14; H, 7.07; N, 12.27 Found: C, 62.89; H, 7.07; N, 12.56

EXAMPLE 30

Methyl Z-4-[[2-butyl-5-[(1-butyl-2,5-dioxo-4-imidazolidinylidene)methyl]-1H-imidazol-1-yl]methyl]benzoate monohydrochloride To a solution of diethyl 2,5-dioxo-4-imidazolyl phosphonate (0.600 g, 2.53 mmol) in methanol (15 mL) is cautiously added sodium hydride (80% dispersion in oil) (0.152 g, 5.06 mmol) and stirred for 15 minutes to afford a pale yellow solution. To this is added methyl 4-[(2-butyl-5-formyl-1H-imidazol-1-yl)methyl]benzoate (0.730 g, 2.43 mmol). This mixture is stirred for 2 hours in which time a yellow precipitate develops. The reaction mixture is concentrated in vacuo and then diluted with water (10 mL). 1 N HCl (5 mL) is added to afford a white precipitate. The precipitate is washed with water (20 mL) and then with ether (20 mL). This solid is the Z-isomer with the E-isomer evident in the filtrate.

Anal. Calcd. for $C_{20}H_{22}N_4O_4$: C, 57.34; H, 5.53; N, 13.38 Found: C, 57.11; H, 5.45; N, 12.93 MS (EI) 382

EXAMPLE 31

Diethyl 1-butyl-2,5-dioxo-4-imidazolyphosphonate

To a solution of diethyl 2,5-dioxo-4-imidazolylphosphonate (6.00 g, 0,025 moles) in DMF (15 mL), under $N_2$, is added $K_2CO_3$ (17.5 g, 0.127 moles) and 1-iodobutane (2.9 mL, 0.025 moles). This mixture is stirred at room temperature for 16 hours and then the mixture is filtered and the solid washed with ethyl acetate. The filtrate is concentrated in vacuo, to afford a yellow oil which is redissolved in ethyl acetate and washed with water and brine and then dried over $MgSO_4$. Evaporation of solvents under high vacuum affords the required product as a viscous yellow oil which solidifies on standing.

Anal. Calcd. for $C_{11}H_{21}N_2O_5P$: C, 45.21; H, 7.24; N, 9.58 Found: C, 44.83; H, 7.34; N, 9.84 MS (EI) 293

EXAMPLES 32a, 32b, 32c

32a

Methyl Z-4-[[2-butyl-5-[(1-butyl-2,5-dioxo-4-imidazolidinylidene)methyl]-1H-imidazol-1-yl]methyl]-benzoate monohydrochloride To a solution of diethyl 1-butyl-2,5-dioxo-4-imidazolylphosphonate (1.47 g, 5.00 mmol) in methylene chloride (8 mL) at 0° C. is added 1,8-diazabicyclo [5.4.0] undec-7-ene (DBU) (0.75 mL, 5.02 mmol). The yellow solution is stirred for 5 minutes and then a solution of methyl 4-[(2-butyl-5-formyl-1H-imidazol-1-yl)methyl]benzoate (1.25 g, 4.17 mmol) is added. This mixture is allowed to stir for 16 hours. The mixture is diluted with ethyl acetate containing 10% methylene chloride and washed with 1M aqueous HCl (15 mL), water and then brine. After drying over $MgSO_4$ the product is isolated as a yellow solid by concentration in vacuo and treatment with ether. Chromatography of the mother liquors after neutralizing with aqueous $NaHCO_3$, eluting with 1% methanol in chloroform, affords a small amount of the corresponding E-isomer. Data for Z-isomer as hydrochloride salt Anal. Calcd. for $C_{24}H_{30}N_4O_4$. HCl: C, 60.69; H, 6.58; N, 11.80 Found: C, 60.25; H, 6.30; N, 11.48
mp 197°-198° C.; MS (EI) 438
Free base mp 172–173° C. Recrystallized from ethyl acetate

32b

Methyl E-4-[[2-butyl-5-[(1-butyl-2,5-dioxo-4-imidazolidinylidene)methyl]-1H-imidazol-1-yl]methyl]-benzoate Anal. Calcd. for $C_{24}H_{30}N_4O_4$. 0.33 $H_2O$: C, 64.84; H, 6.95; N, 12.60 Found: C, 64.55; H, 6.86; N, 12.46 MS (EI) 438 mp 172°-174° C.

32c Alternative procedure

Methyl Z-4-[[2-butyl-5-[(1-butyl-2,5-dioxo-4-imidazolidinylidene)methyl]-1H-imidazol-1-yl]methyl]-benzoate To a solution of diethyl 2,5-dioxo-4-imidazolylphosphonate (1.5 g, 6.33 mmol) in DMF (4 mL) is added $K_2CO_3$ and then 1-iodobutane (0.79 mL, 6.96 mmol). This mixture is stirred for 16 hours at room temperature. To this yellow mixture is added methyl 4-[(2-butyl-5-formyl-1H-imidazol-1-yl)methyl]benzoate (1.05 g, 3.5 mmol). After 2 hours methylene chloride (10 mL) was added to aid stirring. The mixture was stirred for 16 hours. After diluting the reaction mixture with water it was extracted with ethyl acetate. This extract was washed with water and brine. The extract was dried over $MgSO_4$, filtered and then concentrated until crystallization was apparent. The solid was collected and dried.

EXAMPLE 33

Methyl Z-4-[[2-butyl-5-[(1,3-dibutyl-2,5-dioxo-4-imidazolidinylidene)methyl]-1 H-imidazol-1-yl]methyl]benzoate monohydrochloride To a solution of methyl Z-4-[[2-butyl-5-[(1-butyl-2,5-dioxo-4-imidazolidinylidene)methyl]-1H-imidazol-1-yl]methyl]benzoate (0.475 g, 1.08 mmol) in DMF (6 mL) is added $K_2CO_3$ (0.750 g, 5.40 mmol). After stirring for 5 minutes 1-iodobutane (0.150 mL, 1.32 mmol) is added. The mixture is stirred for 16 hours, diluted with ethyl acetate and washed with water and brine and then dried over $MgSO_4$. A viscous oil is obtained by evaporation of the solvents in vacuo. This yellow oil is dissolved in ether and treated with ethereal HCl to precipitate a gummy solid. This gum is crystallized from 2-propanol/ether.

Anal. Calcd. for $C_{28}H_{38}N_4O_4$. HCl: C, 63.32; H, 7.40; N, 10.55 Found: C, 63.36; H, 7.56; N, 10.66 MS (EI) 494

EXAMPLE 34

Methyl Z-4-[[2-butyl-5-[(1-butyl-2,5-dioxo-3-pentyl-4-imidazolidinylidene)methyl]-1H-imidazol-1-yl]benzoate monohydrochloride To a solution of methyl Z-4-[[2-butyl-5-[(1-butyl-2,5-dioxo-4-imidazolidinylidene)methyl]-1H-imidazol-1-yl]methyl]benzoate (0.400 g, 0.92 mmol) in DMF (4 mL) is added $K_2CO_3$ (0.630 g, 4.57 mmol). After stirring for 5 minutes 1-iodopentane (0.155 mL, 1.19 mmol) is added. The mixture is stirred for 16 hours. After diluting with ethyl acetate and washing with water and brine the solution is dried over $MgSO_4$. A viscous oil is obtained by evaporation of the solvents in vacuo. This yellow oil is dissolved in ether and treated with ethereal HCl to precipitate a gummy solid. This gum is crystallized from 2-propanol/ether.

Anal. Calcd. for $C_{29}H_{40}N_4O_4$. HCl: C, 63.89; H, 7.58; N, 10.28 Found: C, 63.91; H, 7.26; N, 10.13 mp 128°-130° C.; MS (EI) 508

EXAMPLE 35

Methyl Z-4-[[2-butyl-5-[(1-butyl-3-hexyl-2,5-dioxo-4-imidazolidinylidene)methyl]-1H-imidazol-1-yl]methyl]benzoate monohydrochloride To a solution of methyl Z-4-[[2-butyl-5-[(1-butyl-2,5-dioxo-4-imidazolidinylidene)methyl]-1H-imidazol-1-yl]methyl]benzoate hydrochloride (0.450 g, 0.95 mmol) in DMF (4 mL) is added $K_2CO_3$ (0.800 g, 5.80 mmol). After stirring for 5 minutes 1-iodohexane (0.190 mL, 1.29 mmol) is added. The mixture is stirred for 16 hours, diluted with ethyl acetate, washed with water and brine, and then dried over $MgSO_4$. A viscous oil is obtained by evaporation of the solvents in vacuo. This yellow oil is dissolved in ether and treated with ethereal HCl to precipitate a gummy solid. This gum is triturated with pentane and ether to afford a pale yellow solid.

Anal. Calcd. for $C_{30}H_{42}N_4O_4$. HCl: C, 64.33; H, 7.92; N, 10.00 Found: C, 64.04; H, 7.61; N, 9.78 mp 134°–135° C.; MS (EI) 522

EXAMPLE 36

Methyl Z-4-[[2-butyl-5-[[1-butyl-2,5-dioxo-3-(phenylmethyl)-4-imidazolidinylidene]methyl]-1H-imidazol-1-yl]methyl]-benzoate monohydrochloride To a solution of methyl Z-4-[[2-butyl-5-[(1-butyl-2,5-dioxo-4-imidazolidinylidene)methyl]-1H-imidazol-1-yl]methyl]benzoate (0.509 g, 1.16 mmol) in DMF (6 mL) is added $K_2CO_3$ (0.800 g, 5.80 mmol). After stirring for 5 minutes benzylbromide (0.150 mL, 1.26 mmol) is added. The mixture is stirred for 16 hours, diluted with ethyl acetate, washed with water and brine, and then dried over $MgSO_4$. A viscous oil is obtained upon chromatography on silica gel (eluant 1% methanol in chloroform) and evaporation of the solvents in vacuo. This yellow oil is dissolved in ether and treated with ethereal HCl to afford a foamy solid upon evaporation in vacuo.

Anal. Calcd. for $C_{31}H_{36}N_4O_4$: HCl. 1.25 $H_2O$: C, 63.35; H, 6.78; N, 9.53 Found: C, 63.13; H, 6.83; N, 9.43 mp 110°–113° C.; MS (EI) 528

EXAMPLE 37

Methyl Z-4-[[2-butyl-5-[[1-butyl-3-[[4-(methoxycarbonyl)phenyl]methyl]-2,5-dioxo-4-imidazolidinylidene]methyl ]-1H- imidazol-1-yl]methyl]benzoate monohydrochloride To a solution of methyl Z-4-[[2-butyl-5-[(1-butyl-2,5-dioxo- 4-imidazolidinylidene) methyl ]-1H- imidazol-1-yl]methyl]benzoate (0.500 g, 1.14 mmol) in DMF (4 mL) is added $K_2CO_3$ (0.800 g, 5.80 mmol). After stirring for 5 minutes methyl (4-bromomethyl)benzoate (0.275 g, 1.20 mmol) is added. The mixture is stirred for 16 hours, diluted with ethyl acetate, washed with water and brine, and then dried over $MgSO_4$. A viscous oil is obtained upon chromatography on silica gel (eluant 1% methanol in chloroform) and evaporation of the solvents in vacuo. This yellow oil is dissolved in ether and treated with ethereal HCl to precipitate a gummy solid. This gum is crystallized from 2-propanol/ether.

Anal. Calcd. for $C_{33}H_{38}N_4O_6$. HCl: C, 64.13; H, 5.54; N, 9.06 Found: C, 63.44; H, 6.31; N, 8.79 mp 165°–167° C.; MS (EI) 528

EXAMPLE 38

Methyl Z-4-[[2-butyl-3-[(4-nitrophenyl)methyl]2,5-dioxo-4-imidazolidinylidene[methyl]-1H-imidazol-1-yl]methyl]benzoate mono hydrochloride To a solution of methyl Z-4-[[2-butyl-5-[[1-butyl-2,5-dioxo-4-imidazolidinylidene]methyl]-1H-imidazol-1-yl]methyl]benzoate (0.370g, 0.84 mmol) in DMF (4 mL) is added $K_2CO_3$ (0.580g, 4.20 mmol). After stirring for 5 minutes 4-nitrobenzylbromide (0.218 g, 1.01 mL) is added. The mixture is stirred for 16 hours, diluted with ethyl acetate, washed with water and brine, and then dried over $MgSO_4$. A viscous oil is obtained upon chromatography on silica gel (eluant 1% methanol in chloroform) and evaporation of the solvents in vacuo. This yellow oil is dissolved in ether and treated with ethereal HCl to afford a foamy solid upon evaporation in vacuo.

Anal. Calcd. for $C_{31}H_{35}N_5O_6$. HCl. $H_2O$: C, 59.27; H, 6.10; N, 11.15 Found: C, 59.03; H, 6.14; N, 10.89 MS (EI) 573

EXAMPLE 39

Methyl Z-4-[[2-butyl5-[[1-butyl-2,5-dioxo-3-[[4-(trifluoromethyl)phenyl[methyl[-4-imidazolidinylidene]methyl]-1H-imidazol-1-yl]methyl]benzoate monohydrochloride To a solution of methyl Z-4-[[2-butyl-5-[(1-butyl-2,5-dioxo-4-imidazolidinylidene)methyl]-1H-imidazolyl]-methyl]benzoate (0.450g, 1.03 mmol) in DMF (4 mL) is added $K_2CO_3$ (0.800 g, 5.80 retool). After stirring for 5 minutes 4-trifluoromethylbenzyl bromide (0.270 1.13 mmol) is added. The mixture is stirred for 16 hours to generate a red colored mixture. After diluting with ethyl acetate and washing with water and brine the solution is dried over $MgSO_4$. A viscous oil is obtained upon chromatography on silica gel (eluant 1% methanol in chloroform) and evaporation of the solvents in vacuo. This orange oil is dissolved in ether and treated with ethereal HCl to afford a foamy solid upon evaporation in vacuo. This solid is dissolved in methylene chloride and treated with pentane to afford a pale yellow solid.

Anal. Calcd. for $C_{33}H_{35}N_4O_4F_3$. HCl. 0.67 $H_2O$: C, 59.57; H, 5.83; N, 8.69 Found: C, 59.55; H, 5.65; N, 8.39 MS (EI) 596

EXAMPLE 40

Methyl Z-4-[[2-butyl-5-[[1-butyl-2,5-dioxo-3-(3-thienylmethyl)-4-imidazolidene]methyl]-1H-imidazol-1-yl]methyl]benzoate mono hydrochloride To a solution of methyl Z-4-[[2-butyl-5-[(1-butyl-2,5-dioxo-4-imidazolidinylidene)methyl]-1H-imidazol-1-yl]methyl]benzoate hydrochloride (0.50 g, 1.05 mmol) in DMF (4 mL) is added $K_2CO_3$ (0.730 g, 5.29 mmol). After stirring for 5 minutes. 3-thienylmethyl bromide (0.250 g, 1.41 mmol) is added. The mixture is stirred for 16 hours to generate a viscous pale brown colored mixture. After diluting with ethyl acetate and washing with water and brine the solution is dried over $MgSO_4$. A viscous oil is obtained upon chromatography on silica gel (eluant 0.5% methanol in chloroform) and evaporation of the solvents in vacuo. This oil is dissolved in ether and treated with ethereal HCl to afford a foamy solid upon evaporation in vacuo. This solid is crystallized from 2-propanol/ether.

Anal. Calcd. for $C_{33}H_{35}N_4O_4$. HCl. 0.67 $H_2O$: C, 60.99; H, 6.18; N, 9.81 Found: C, 60.83; H, 6.24; N, 9.61 mp 178°–179° C.; MS (EI) 534

EXAMPLE 41

Methyl Z-4-[[2-butyl-5-[[1-butyl-2,5-dioxo-3-(2-phenylethyl)-4-imidazolidinylidene]methyl]-1H-imidazol-1-yl]methyl]-benzoate mono hydrochloride To a solution of methyl Z-4-[[2-butyl-5-[(1-butyl-2,5-dioxo-4-imidazolidinylidene)methyl]-1H-imidazol-1-yl]methyl]benzoate monohydrochloride (0.500 g, 1.05 retool) in DMF (4 mL) is added $K_2CO_3$ (0.730 g, 5.29 mmol). After stirring for 5 minutes 2-phenylethyl bromide (0.215 mL, 1.57 mmol) is added. The mixture is stirred for 16 hours to generate a viscous yellow colored mixture. After diluting with ethyl acetate and ether and washing with water and brine the solution is dried over $MgSO_4$. A viscous oil is obtained upon chromatography on silica gel (eluant chloroform) and evaporation of the solvents in vacuo. This oil is dissolved in ether and treated with ethereal HCl to afford a foamy solid upon evaporation in vacuo. This solid is crystallized from 2-propanol/ether.

Anal. Calcd. for $C_{33}H_{35}N_4O_4$. HCl: C, 65.50; H, 6.78; N, 9.22 Found: C, 65.68; H, 6.83; N, 9.58 mp 150°–151° C.; MS (CI) 543(M+1)

EXAMPLE 42

Methyl Z-4-[[2-butyl-5-[[1-butyl-2,5-dioxo-3-(diphenylmethyl)-4-imidazolidinylidene]methyl]-1H-imidazol-1-yl]methyl]benzoate mono hydrochloride To a solution of methyl Z-4-[[2-butyl-5-[(1-butyl-2,5-dioxo-4-imidazolidinylidene)methyl]-1H-imidazol-1-yl]methyl]benzoatehydrochloride (0.361 g, 0.76 mmol) in DMF (4 mL) is added $K_2CO_3$ (0.525 g, 3.80 mmol). After stirring for 5 minutes diphenylmethyl bromide (0.240 g, 0.97 mmol) is added. The mixture is stirred for 16 hours to generate a viscous yellow colored mixture. After diluting with ether and washing with water and brine the solution is dried over $MgSO_4$. This oil was redissolved in DMF (4 mL) and $K_2CO_3$ (0.525 g, 3.80 mmol) and bromodiphenyl methane (0.560 g, 2.27 mmol) is added. The mixture is stirred for 16 hours to generate a red colored mixture. After diluting with ether and washing with water and brine the solution is dried over $MgSO_4$. A viscous oil is obtained upon chromatography on silica gel (eluant chloroform) and evaporation of the solvents in vacuo. This oil is dissolved in ether and treated with ethereal HCl to afford a foamy solid upon evaporation in vacuo. This solid is crystallized from 2-propanol/ether.

Anal. Calcd. for $C_{37}H_{40}N_4O_4$. HCl: C, 69.31; H, 6.45; N, 8.74 Found: C, 69.03; H, 6.09; N, 8.34 mp 184°–185° C.; MS (EI) 604

EXAMPLE 43

Methyl Z-4-[[2-butyl-5-[[1-butyl-3-(cyclohexylmethyl)-2,5-dioxo-4-imidazolidinylidene]methyl]-1H-imidazol-1-yl]methyl]benzoate mono hydrochloride To a solution of methyl Z-4-[[2-butyl-5-[(1-butyl-2,5-dioxo-4-imidazolidinylidene)methyl]-1H-imidazol-1-yl]methyl]benzoate (0.250 g, 0.57 mmol) in DMF (4 mL) is added sodium hydride (80% dispersion in oil) (0.02 g, 0.67 mmol). After stirring for 5 minutes cyclohexylmethyl bromide (0.20 mL, 1.43 mmol) is added. The mixture is stirred for 16 hours and then a further amount of cyclohexylmethyl bromide is added (0.20 mL, 1.43 mmol) along with a catalytic amount of sodium iodide. The mixture is stirred for 16 hours, diluted with ether, washed with water and brine and dried over $MgSO_4$. A viscous oil is obtained upon chromatography on silica gel (eluant 1.0% methanol in chloroform) and evaporation of the solvents in vacuo. This oil is dissolved in ether and treated with ethereal HCl to afford a foamy solid upon evaporation in vacuo. This solid is crystallized from 2-propanol/ether. Anal. Calcd. for $C_{31}H_{42}N_4O_4$. HCl: C, 65.19; H, 7.59; N, 9.81 Found: C, 65.25; H, 7.64; N, 9.85 mp 157°–158° C.; MS (EI) 534

EXAMPLE 44

Methyl Z-4-[[2-butyl-5-[[1-butyl-2,5-dioxo-3-(1H-tetrazol-5-ylmethyl)-4-imidazolidinylidene]methyl]-1H-imidazol-1-yl]methyl]benzoate monohydrochloride To a solution of methyl Z-4-[[2-butyl-5-[(1-butyl-2,5-dioxo-4-imidazolidinylidene)methyl]-1H-imidazol-1-yl]methyl]benzoate (0.300 g, 0.68 mmol) in DMF (5 mL) is added $K_2CO_3$ (0.500 g, 3.62 mmol). After stirring for 5 minutes 2-triphenylmethyl-1H-tetrazol-5-ylmethyl chloride (0.500 g, 1.39 mmol) is added. The mixture is stirred for 16 hours to generate a viscous orange colored mixture. After diluting with ethyl acetate and washing with water and brine the solution is dried over $MgSO_4$. A viscous oil is obtained upon chromatography on silica gel (eluant 0.5 % methanol in chloroform) and evaporation of the solvents in vacuo. This oil is dissolved in methanol (50 mL) and treated with acetic acid (0.04 mL, 0.70 mmol). After heating at 90° C. (oil bath temp. ) for 2 hours the solution is cooled and treated with water (10 mL) and hexanes (100 mL). The aqueous organic layer is separated and evaporated. This solid is redissolved in ethyl acetate/methylene chloride and washed with pH 7 buffer, dried over $MgSO_4$ and evaporated in vacuo. The hydrochloride salt is then prepared by dissolving this solid in methanol and treating with ethereal HCl. Evaporation in vacuo of this solution and crystallization (2-propanol/ether) affords the required compound.

Anal. Calcd. for $C_{26}H_{32}N_8O_4$.HCl: C, 56.38; H, 6.00; N, 19.73 Found: C, 56.06; H, 5.97; N, 20.12 mp 192°–195° C.; MS (CI) 521

EXAMPLE 45

Methyl Z-4-[[2-butyl-5-[[1-butyl-3-(1H-imidazol-5-ylmethyl)-2,5-dioxo-4-imidazolidinylidene]methyl]-1H-imidazol-1-yl]methyl]benzoate monohydrochloride To a solution of methyl Z-4-[[2-butyl-5-[(1-butyl-2,5-dioxo-4-imidazolidinylidene)methyl]-1H-imidazol-1-yl]methyl]benzoate hydrochloride (0.237 g, 0.50 mmol) in DMF (3 mL) is added $K_2CO_3$ (0.350 g, 2.54 mmol). After stirring for 5 minutes 4-(chloromethyl)-1-(triphenylmethyl)-1H-imidazole (0.250 g, 0.70 mmol) is added. The mixture is stirred for 16 hours, diluted with ethyl acetate, washed with water and brine and then dried over $MgSO_4$. A viscous oil is obtained upon chromatography on silica gel (eluant 0.5 % methanol in chloroform) and evaporation of the solvents in vacuo. This oil is dissolved in methanol (80 mL) and treated with acetic acid (30 mn). After heating at 90° C. (oil bath temp.) for 4 hours the solution is cooled and treated with water (10 mL) and hexanes (100 mL). The aqueous organic layer is separated and evaporated. This solid is redissolved in ethyl acetate/methylene chloride and washed with pH 7 buffer, dried over MgSO$_4$ and evaporated in vacuo. The hydrochloride salt is then prepared by dissolving this solid in methanol and treating with ethereal HCl. Evaporation in vacuo of this solution and crystallization (2-propanol/ether) affords the required compound.

Anal. Calcd. for $C_{28}H_{34}N_6O_4$. 2HCl. H$_2$O: C, 55.17; H, 6.28; N, 13.79 Found: C, 54.88; H, 6.13; N, 13.24 mp 202°–205° C.; MS (EI) 518

EXAMPLE 46

Diethyl 1-hexyl-2,5-dioxo-4-imidazolylphosphonate

To a solution of diethyl 2,5-dioxo-4-imidazolylphosphonate (6.00 g, 0.025 moles) in DMF (15 mL), under N$_2$, is added K$_2$CO$_3$ (17.5g, 0.127 moles) and 1-iodohexane (3.75 mL, 0.025 moles). This mixture is stirred at room temperature for 16 hours. The mixture is diluted with ether (300 mL) and washed with water and brine and then dried over MgSO$_4$. Evaporation of solvents under high vacuum affords the required product as a viscous yellow oil. (Mass spectrometry also revealed a small amount of diethyl 1,3-dihexyl-2,5-dioxo-4-imidazolylphosphonate) MS (EI) 321

EXAMPLE 47

Methyl ZX-4-[[2-butyl-5-[(1-hexyl-2,5-dioxo-4-imidazolidinylidene]methyl]-1H-imidazol-1-yl]m,ethyl]benzoate To a solution of diethyl 1-hexyl-2,5-dioxo-4-imidazolylphosphonate (3.50 g, 0.011 moles) in methylene chloride (30 mL) at −40° C. is added 1,8-diazabicyclo [5.4.0] undec-7-ene (1.64 mL, 0.011 moles). The yellow solution is stirred for 5 minutes and then a solution of methyl 4-[(2-butyl-5-formyl-1H-imidazol-1-yl)methyl]benzoate (3.25 g, 0.011 moles) is added. This mixture is allowed to stir for 16 hours with warming to room temperature. The mixture is diluted with ethyl acetate and washed with water and then brine. After adding methylene chloride (50 mL) and drying over MgSO$_4$ the product is isolated as a yellow solid by concentration in vacuo and treatment with ether.

Anal. Calcd. for $C_{26}H_{34}N_4O_4$. 0.3 H$_2$O: C, 66.16; H, 7.39; N, 11.87 Found: C, 65.96; H, 7.07; N, 11.70 mp 178°–180° C.; MS (EI) 466

EXAMPLE 48

Methyl Z-4-[[2-butyl-5-[(3-butyl-1-hexyl-2,5-dioxo-4-imidazolidinylidene)methyl]-1H-imidazol-1-yl]methyl]-benzoate monohydrochloride To a solution of methyl Z-4-[[2-butyl-5-[[1-hexyl-2,5-dioxo-4-imidazolidinylidene]methyl]-1H-imidazol-1-yl]methyl]benzoate (0.50 g, 1.07 retool) in DMF (4 mL) is added K$_2$CO$_3$ (0.740g, 5.36 retool). After stirring for 5 minutes 1-iodobutane (0.158 mL, 1.39 mmol) is added. The mixture is stirred for 16 hours. After diluting with ether (150 mL) and washing with water and brine the solution is dried over MgSO$_4$. A viscous oil is obtained by evaporation of the solvents in vacuo. This yellow oil is dissolved in ether and treated with ethereal HCl to precipitate a gummy solid. This gum is crystallized from 2-propanol/ether.

Anal. Calcd. for $C_{30}H_{43}N_4O_4$. HCl. 0.3H$_2$O: C, 64.64; H, 7.95; N, 9.89 Found: C, 63.65; H, 7.56; N, 9.43 mp 144°–145° C.; MS (EI) 522

EXAMPLE 49

Methyl Z-4-[[2-butyl-5-[[1-hexyl-2,5-dioxo-3-(3-thienylmethyl)-4-imidazolidinylidene]methyl]-1H-imidazol-1-yl]methyl]benzoate monohydrochloride To a solution of methyl Z-4-[[2-butyl-5-[(1-hexyl-2,5-dioxo-4-imidazolidinylidene)methyl]-1H-imidazol-1-yl]methyl]benzoate (0.515 g, 1.11 retool) in DMF (7 mL) is added K$_2$CO$_3$ (0.760 g, 5.51 retool). After stirring for 5 minutes 3-thienylmethyl bromide (0.39 g, 2.20 mmol) is added. The mixture is stirred for 16 hours to generate a viscous pale brown colored mixture. After diluting with ether and washing with water and brine the solution is dried over MgSO$_4$. The solvents are evaporated in vacuo and this oil is dissolved in ether and treated with ethereal HCl to afford a foamy solid upon evaporation in vacuo. This solid is crystallized from 2-propanol/ether.

Anal. Calcd. for $C_{31}H_{38}N_4O_4$. HCl. H$_2$O: C, 60.32; H, 6.70; N, 9.08 Found: C, 59.95; H, 6.55; N, 8.68 MS (FAB) 564

EXAMPLE 50

Methyl Z-4-[[2-butyl-5-[[1-hexyl-2,5-dioxo-3-(phenylmethyl)-4-imidazolidinylidene]methyl]-1H-imidazol-1-yl]methyl]-benzoate monohydrochloride To a solution of methyl Z-4-[[2-butyl-5-[(1-hexyl-2,5-dioxo-4-imidazolidinylidene)methyl]-1H-imidazol-1-yl]methyl]benzoate (0.516 g, 1.11 mmol) in DMF (7 mL) is added K$_2$CO$_3$ (0,760 g, 5.51 mmol). After stirring for 5 minutes benzylbromide (0,150 mL, 1.26 mmol) is added. The mixture is stirred for 16 hours. After diluting with ether and ethyl acetate and washing with water and brine the solution is dried over MgSO$_4$. A viscous oil is obtained upon evaporation of the solvents in vacuo. This yellow oil is dissolved in ether and treated with ethereal HCl to afford a foamy solid upon evaporation in vacuo. This solid is crystallized from 2-propanol/ether.

Anal. Calcd. for $C_{33}H_{40}N_4O_4$. HCl: C, 64.68; H, 7.42; N, 10.06 Found: C, 64.76; H, 7.06; N, 10.53 mp 98°–100° C.; MS (CI) 557 (M+I)

EXAMPLE 51

Methyl Z-4-[[2-butyl-5-[1-hexyl-3-[(2-methyl-4-thiazolyl)methyl-2,5-dioxo-4-imidazolidinylidene]methyl]-1H-imidazol-1-yl]methyl]benzoate dihydrochloride To a solution of methyl Z-4-[[2-butyl-5-[(1-hexyl-2,5-dioxo-4-imidazolidinylidene)methyl]-1H-imidazol-1-yl]methyl]benzoate (0.300 g, 0.643 mmol) in DMF (4 mL) is added K$_2$CO$_3$ (0,440 g, 3.19 mmol). After stirring for 5 minutes 4-chloromethyl-2-methylthiazole hydrochloride (0.237 g, 1.29 mmol) is added. The mixture is stirred for 16 hours in which time a pale brown slurry forms. After diluting with ethyl acetate and washing with water and brine the solution is dried over MgSO$_4$. Chromatography eluting with 2% methanol in chloroform and evaporation in vacuo affords a viscous oil.

This oil is dissolved in ether and treated with ethereal HCl to afford a foamy solid upon evaporation in vacuo. This solid is crystallized from 2-propanol/ether.

Anal. Calcd. for $C_{31}H_{39}N_5O_4S \cdot 2HCl \cdot H_2O$: C, 55.67; H, 6.48; N, 10.47 Found: C, 55.57; H, 6.29; N, 10.15 mp 160°–162° C.; MS (EI) 577

EXAMPLE 52

Diethyl 1-(methoxymethyl)-2,5-dioxo-4-imidazolylphosphonate

To a solution of diethyl 2,5-dioxo-4-imidazolylphosphonate (3.61 g, 0.015 moles) in DMF (10 mL), under $N_2$, is added sodium hydride (80% dispersion in oil) (0.55 g, 0.018 moles) and stirred for 5 minutes. Chloromethyl methyl ether (tech. grade 85%) (1.9 mL, 0.021 moles) is added. This mixture is stirred at room temperature for 4 hours, diluted with ether and ethyl acetate (300 mL) and then washed with water and brine before drying over $MgSO_4$. The aqueous layer is back extracted with methylene chloride and combined with the previous organic fraction. Evaporation of solvents and chromatography (eluant 1% methanol in chloroform) and evaporation under high vacuum affords the required product. MS (EI) 280

EXAMPLE 53

Methyl Z-4-[[2-butyl-5-[[(1-(methoxymethyl)-2,5-dioxo-4-imidazolidinylidene]methyl]-1H-imidazol-1-yl]methyl]-benzoate To a solution of diethyl 1-(methoxymethyl)-2,5-dioxo-4-imidazolylphosphonate (2.40g, 8.57 mmol) in methylene chloride (10 mL) at 0° C. is added 1,8-diazabicyclo [5.4.0] undec-7-ene (1.30 mL, 8.71 mmol). The yellow solution is stirred for 5 minutes and then a solution of methyl 4-[(2-butyl-5-formyl-1H-imidazol-1-yl)methyl]benzoate (2.0 g, 6.67 mmol) is added. This mixture is allowed to stir for 16 hours, diluted with ethyl acetate, and washed with water and then brine. After adding methylene chloride (50 mL) and drying over $MgSO_4$ the product is isolated as a yellow solid by partial concentration in vacuo and treatment with ether.

Anal. Calcd. for $C_{22}H_{26}N_4O_5$:C, 61.96; H, 6.15; N, 13.14 Found: C, 61.69; H, 6.17; N, 12.99 mp 185°–186° C.; MS (EI) 426

EXAMPLE 54

Methyl Z-4-[[2-butyl-5-[[3-butyl-1-(methoxymethyl)-2,5-dioxo-4-imidazolidinylidene]methyl]-1H-imidazol-1-yl]methyl]benzoate monohydrochloride To a solution of methyl Z-4-[[2-butyl-5-[[1-(methoxymethyl)-2,5-dioxo-4-imidazolidinylidene]methyl]-1H-imidazol-1-yl]methyl]benzoate (0.70 g, 1.07 mmol) in DMF (4 mL) is added $K_2CO_3$ (1.13 g, 8.19 mmol). After stirring for. 5 minutes 1-iodobutane (0.24 mL, 2.11 mmol) is added. The mixture is stirred for 16 hours. After diluting with ether (150 mL) and washing with water and brine the solution is dried over $MgSO_4$. A viscous oil is obtained by evaporation of the solvents in vacuo. This yellow oil is dissolved in ether and treated with ethereal HCl to precipitate a gummy solid. This gum is crystallized from 2-propanol/ether.

Anal. Calcd. for $C_{26}H_{34}N_4O_5 \cdot HCl$: C, 60.17; H, 6.80; N, 10.79 Found: C, 59.87; H, 6.88; N, 10.73 mp 133°–134° C.; MS (EI) 482

EXAMPLE 55

Methyl Z-4-[[2-butyl-5-[[1-(methoxymethyl)-2,5-dioxo-3-(phenylmethyl)-4-imidazolidinylidene]methyl]-1H-imidazol-1-yl]methyl]benzoate monohydrochloride To a solution of methyl Z-4-[[2-butyl-5-[[1-methoxymethyl-2,5-dioxo-4-imidazolidinylidene]methyl]-1H-imidazol-1-yl]methyl]benzoate (0.34 g, 0.79 mmol) in DMF (4 mL) is added $K_2CO_3$ (0.55 g, 3.99 mmol). After stirring for 5 minutes benzylbromide (0.113 mL, 0.95 mmol) is added. The mixture is stirred for 16 hours, diluted with ether and washed with water and brine and then dried over $MgSO_4$. A viscous oil is obtained upon evaporation of the solvents in vacuo. This yellow oil is dissolved in ether and treated with ethereal HCl to afford a foamy solid upon evaporation in vacuo. This solid is crystallized from 2-propanol/ether.

Anal. Calcd. for $C_{29}H_{32}N_4O_5 \cdot HCl$: C, 62.98; H, 6.01; N, 10.13 Found: C, 62.59; H, 5.97; N, 9.92 mp 137°–138° C.; MS (EI) 516

EXAMPLE 56

Methyl Z-4-[[2-butyl-5-[[1-(methoxymethyl)-3-[(2-methyl-4-thiazolyl)methyl]-2,5-dioxo-4-imidazolidinylidene]methyl]-1H-imidazol-1-yl]methyl]benzoate dihydrochloride To a solution of methyl Z-4-[[2-butyl-5-[[1-(methoxymethyl)-2,5-dioxo-4-imidazolidinylidene]methyl]-1H-imidazol-1-yl]methyl]benzoate (0.307 g, 0.721 mmol) in DMF (4 mL) is added $K_2CO_3$ (0.500 g, 3.62 mmol). After stirring for 5 minutes 4-chloromethyl-2-methylthiazole hydrochloride (0.265 g, 1.44 mmol) is added. The mixture is stirred for 48 hours. A pale brown slurry results which was diluted with ethyl acetate and washed with water and brine and then dried over $MgSO_4$. Chromatography eluting with 1% methanol in chloroform and evaporation in vacuo affords a viscous oil. This oil is dissolved in ether and treated with ethereal HCl to afford a foamy solid upon evaporation in vacuo. This solid is crystallized from 2-propanol/ether.

Anal. Calcd. for $C_{27}H_{31}N_5O_5S \cdot 2HCl$: C, 53.11; H, 5.45; N, 11.47 Found: C, 53.07; H, 5.46; N, 11.48 mp 205°–209° C.; MS (EI) 537

EXAMPLE 57

Methyl Z-4-[[2-butyl-5-[[1-butyl-2,5-dioxo-3-[(2-pyridinyl-N-oxide)-methyl]-4-imidazolidinylidene]methyl]-1H-imidazol-1-yl]methyl]benzoate To a solution of methyl Z-4-[[2-butyl-5-[(1-butyl-2,5-dioxo-4-imidazolidinylidene)methyl]-1H-imidazol-1-yl]methyl]benzoate (0.569 g, 1.2 mmol) in DMF (5 mL) is added $K_2CO_3$ (2.00 g, 15 mmol). After stirring for 5 minutes 2-chloromethylpyridine-N-oxide (0.230 g, 1.3 mmol) is added and the mixture is stirred for 16 hours. The dark brown mixture is filtered, concentrated in vacuo, and dissolved in 30% methylene chloride in ether (50 mL). This solution is washed with water and dried over $K_2CO_3$ and charcoal. A viscous oil is obtained by evaporation of the solvents in vacuo. This yellow oil is dissolved in hot ethyl acetate (5 mL) and upon brief standing crystallization occurs. The crystals are collected and washed with ether.

Anal. Calcd. for $C_{30}H_{35}N_5O_5$: C, 66.04; H, 6.47; N, 12.84 Found: C, 66.34; H, 6.56; N, 12.88 mp 150°–152° C.; MS (CI) 546 (M+1)

EXAMPLE 58

Methyl Z-4-[[2-butyl-5-[[1-butyl-2,5-dioxo-3-(2-pyridinylmethyl)-4-imidazolidinylidene]methyl]-1H-imidazol-1-yl]methyl]benzoate dihydrochloride A solution of methyl Z-4-[[2-butyl-5-[[1-butyl-2,5-dioxo-3-[(2-pyridinyl-N-oxide)methyl]-4imidazolidinylidene]methyl]-1H-imidazol-1-yl]methyl]benzoate in methylene chloride (2 mL) is added dropwise over 3 minutes to phosphorus trichloride (2.0 mL). After 15 minutes the mixture is concentrated under reduced pressure. The residue is dissolved in warm iso-propanol (3 mL) and saturated with HCl gas briefly. Ether is added and the crystals collected and washed with ether. A portion of this sample is recrystallized from 2-propanol/ether.

Anal. Calcd. for $C_{30}H_{35}N_5O_4 \cdot 2HCl \cdot 0.5H_2O$: C, 58.91; H, 6.26; N, 11.45 Found: C, 58.65; H, 6.04; N, 11.15 mp 195°–197° C.; MS (CI) 530 (M+1)

EXAMPLE 59

Z-4-[[2-butyl-5-[[1-butyl-3-[(2-methyl-4thiazolyl)methyl]-2,5-dioxo-4-imidazolidinylidene]methyl]-1H-imidazol-1-yl]methyl]benzoic acid A mixture of methyl Z-4-[[2-butyl-5-[[1-butyl-3-[(2-methyl-4-thiazolyl)methyl]-2,5dioxo-4-imidazolidinylidene]methyl]-1H-imidazol-1-yl]methyl]benzoate (0.428 g, 0.65 mmol) and 2N HCl (12 mL) is refluxed for 1 hour in which time all the solid dissolved. Solvents are removed in vacuo and the mixture is evaporated from ethanol (5 mL) three times. The solid that results is treated with 5% aqueous sodium acetate (10 mL) and water (10 mL) to precipitate a gummy solid which is dissolved in methylene chloride (30 mL). The organic layer is dried over $Na_2SO_4$ and then evaporated in vacuo. The residue is recrystallized from hot ethyl acetate/hexane.

Anal. Calcd. for $C_{28}H_{33}N_5O_4S$: C, 62.78.; H, 6.21; N, 13.07 Found: C, 63.01; H, 6.27; N, 13.05 mp 152°–154° C.; MS (CI) 536 (M+1)

EXAMPLE 60

Isomerization of Z-4-[[2-butyl-5-[[1-butyl-3-[(2-methyl-4-thiazolyl)methyl]-2,5-dioxo-4-imidazolidinylidene]methyl]-1H-imidazol-1-yl]methyl]benzoic acid to E-4-[[2-butyl-5-[[1-butyl-3-[(2-methyl-4-thiazolyl)methyl]-2,5-dioxo-4-imidazolidinylidene]methyl]-1H-imidazol-1-yl]methyl]benzoic acid Methyl Z-4-[[2-butyl-5-[[1-butyl-3-[(4-methyl-2-thiazolyl)methyl]-2,5-dioxo-4-imidazolidinylidene]methyl]-1H-imidazol-1-yl]methyl]benzoic acid (0.25 g, 0.46 retool) was dissolved in concentrated HCl (15 mL) and the mixture is refluxed for 4 hours. The mixture is concentrated in vacuo and aqueous sodium acetate is added. The precipitate is collected and washed with water. This solid is dissolved in methanol (2 mL) and treated with charcoal and then filtered and concentrated in vacuo. The residue was recrystallized from hot ethyl acetate.

Anal. Calcd. for $C_{28}H_{33}N_5O_4S \cdot 0.25 H_2O$: C, 62.26; H, 6.25; N, 12.97 Found: C, 62.28; H, 6.16; N, 12.62 mp 181°–183° C.; MS (CI) 536 (M+1)

EXAMPLE 61

Methyl Z-4-[[2-butyl-5-[[1-butyl-3-[(2-chlorophenyl)methyl]-2,5-dioxo-4-imidazolidinylidene]methyl]-1H-imidazol-1-yl-]methyl]benzoate monohydrochloride To a solution of methyl Z-4-[[2-butyl-5-[(1-butyl-2,5-dioxo-4-imidazolidinylidene)methyl]-1H-imidazol-1-yl]methyl]benzoate (0.474 g, 1.0 retool) in DMF (10 mL) is added $K_2CO_3$ (2.0 g, 15 mmol). After stirring for 5 minutes 1-chloro-2-chloromethylbenzene (0.177 g, 1.1 mmol) is added and the mixture is stirred for 16 hours. The mixture is filtered, concentrated in vacuo, and then dissolved in ether (50 mL). This solution is washed with water and dried over $K_2CO_3$. A viscous oil is obtained by evaporation of the solvents in vacuo which is purified via chromatography, eluant 1% methanol in chloroform. The appropriate fraction is dissolved in ether and treated with ethereal HCl and then evaporated in vacuo to afford a solid foam.

Anal. Calcd. for $C_{31}H_{35}ClN_4O_4 \cdot HCl \cdot 0.5 H_2O$: C, 61.18; H, 6.13; N, 9.21 Found: C, 60.85; H, 6.18; N, 9.07 mp 120°–130° C.; MS (CI) 563 (M+1)

EXAMPLE 62

Methyl Z-4-[[2-butyl-5-[[1-butyl-3-[(2-amino-4-thiazolyl)methyl]-2,5-dioxo-4-imidazolidinylidene]methyl]-1H-imidazol-1-yl]methyl]benzoate dihydrochloride To a solution of methyl Z-4-[[2-butyl-5-[(1-butyl-2,5-dioxo-4-imidazolidinylidene)methyl]-1H-imidazol-1-yl]methyl]benzoate (0.569 g, 1.2 mmol) in DMF (5 mL) is added $K_2CO_3$ (2.0 g, 15 mmol). After stirring for 5 minutes 2-amino-4-chloromethylthiazole hydrochloride (0.222 g, 1.2 mmol) is added. The mixture is stirred for 48 hours and then filtered. The filtrate is concentrated in vacuo and dissolved in methylene chloride (30 mL). This solution is washed with water and dried over $K_2CO_3$ and charcoal. A viscous oil is obtained by evaporation of the solvents in vacuo. This oil is dissolved in ether and treated with ethereal HCl to precipitate a gum which is collected by decantation. This gum is recrystallized from 2-propanol/ether.

Anal. Calcd. for $C_{28}H_{34}N_6O_4S \cdot 2HCl \cdot 2H_2O$: C, 50.90; H, 6.10; N, 12.87 Found: C, 51.23; H, 6.10; N, 12.67 mp 171°–174° C.; MS (CI) 551 (M+1)

EXAMPLE 63

Methyl Z-4-[[2-butyl-5-[2,5-dioxo-3-[(2-thienyl)methyl]-4-imidazolidinylidene]methyl]-1H-imidazol-1-yl]methyl]benzoate HCl gas is passed through a mixture of the Z and E isomers of 4-[[2-butyl-5-[2,5-dioxo-3-[(2thienyl)methyl]-4-imidazolidinylidene]methyl]-1H-imidazol-1-yl]methyl]benzoic acid (3.50 g, 7.5 mmol) in methanol (250 mL). The solid dissolved and the internal temperature rises to 50° C. The solution is allowed to stir for 16 hours at room temperature. The solution is concentrated to approximately 10 mL volume and saturated $NaHCO_3$ (150 mL) is added to adjust the pH to 7.5. The mixture is filtered and washed with water. The Z and E isomers are separated by chromatography (eluant 1–5% methanol in chloroform) and crytallized from warm ethyl acetate.

Anal. Calcd. for $C_{25}H_{26}N_4O_4S$. 0.1 $H_2O$: C, 61.89; H, 5.44; N, 11.55 Found: C, 62.07; H, 5.34; N, 11.31 mp 167°–169° C.; MS (CI) 479 (M+1)

EXAMPLE 64

Methyl Z-4-[[2-butyl-5-[[3-[(4-chlorophenyl)methyl]-2,5-dioxo-4-imidazolidinylidene]methyl]-1H-imidazol-1-yl]methyl]benzoate monohydrochloride HCl gas is passed through a solution of methyl Z-4-[[2-butyl-5-[[3-[(4-chlorophenyl)methyl]-2,5-dioxo-4-imidazolidinylidene]methyl]-1H-imidazol-1-yl]methyl]-benzoic acid (0.73 g, 1.5 mmol) in methanol (15 mL). The solution is allowed to stir for 16 hours at room temperature. The solution is concentrated to approximately 5 mL volume and then ether is added to induce crystallization. The mixture is filtered and washed with ether.

Anal. Calcd. for $C_{27}H_{27}N_4O_4Cl$. HCl: C, 59.67; H, 5.19; N, 10.31 Found: C, 59.45; H, 5.09; N, 9.99 mp 240°–242° C.; MS (CI) 507

EXAMPLE 65

4-[[2-Butyl-5-[(3-butyl-2,5-dioxo-4-imidazolidinyl)methyl]-1H-imidazol-1-yl]methyl]benzoic acid To a solution of E -4-[[2-butyl-5-[(3-butyl-2,5-dioxo-4-imidazolidinylidene)methyl]-1H-imidazol-1-yl]methyl]benzoic acid (0.84 g, 2.00 mmol) in 1N NaOH (2.04 mL, 2.04 mmol) and water (500 mL) is added $PtO_2$ (0.200 g) and then a hydrogen balloon is attached. The mixture is stirred for 3 hours. 1N HCl (2.04 mL, 2.04 mmol) is added and then the mixture is concentrated at reduced pressure. Ethanol (50 mL) is added and the mixture filtered. After evaporating in vacuo the residue is purified by crystallization and chromatography.

Anal. Calcd. for $C_{23}H_{30}N_4O_4S$. $H_2O$: C, 62.14; H, 7.26; N, 12.61 Found: C, 62.35; H, 7.08; N, 12.68 MS (CI) 427 (M+1)

EXAMPLE 66

Methyl Z-4-[[2-butyl-5-[[1-butyl-3-[(4-chlorophenyl)methyl]-2,5-dioxo-4-imidazolidinylidene]methyl]-1H-imidazol-1-yl]methyl]benzoate monohydrochloride To a solution of methyl Z-4-[[2-butyl-5-[[3-[(4-chlorophenyl)methyl]-2,5-dioxo-4-imidazolidinylidene]methyl]-1H-imidazol-1-yl]methyl]benzoate (0.50 g, 0.92 mmol) in DMF (5 mL) is added $K_2CO_3$ (2.0 g, 15 retool). After stirring for minutes 1-iodobutane (0.184 g, 1.0 mmol) is added. The mixture is stirred for 4 hours. The mixture is filtered and the filtrate is concentrated in vacuo and treated with water (20 mL) to afford a gum upon decantation. This gum is dissolved in ether and washed with water and then dried over $K_2CO_3$. A viscous oil is obtained by evaporation of the solvents in vacuo. This oil is dissolved in ether and treated with ethereal HCl to precipitate a gum which is collected by decantation. This gum solidifies upon extended evaporation in vacuo. This solid foam contains 2-propanol as determined by 1H-NMR Anal. Calcd. for $C_{31}H_{35}ClN_4O_4S.HCl.H_2$). 0.15 i-PrOH: Calcd. C, 60.26; H, 6.31; N, 8.95 Found: C, 60.50; H, 6.12; N, 8.86 MS (CI) 564 (M+1)

EXAMPLE 67

Methyl Z-4-[[2-butyl-5-[[1-butyl-2,5-dioxo-3-(2-thienylmethyl)-4-imidazolidinylidene]methyl]-1H-imidazol-1-yl]methyl]benzoate monohydrochloride To a solution of methyl Z-4-[[2-butyl-5-[[2,5-dioxo-3-(2-thienylmethyl)-4-imidazolidinylidene]methyl]-1H-imidazol-1-yl]methyl]benzoate (0.70 g, 1.46 mmol) in warm DMF (10 mL) is added $K_2CO_3$ (2.0 g, 15 mmol). After stirring for 5 minutes 1-iodobutane (0.312 g, 1.7 mmol) is added. The mixture is stirred for 2 hours. The mixture is filtered and the filtrate is concentrated in vacuo and treated with water (20 mL) to afford a gum upon decantation. This gum is dissolved in ether and washed with water and then dried over $K_2CO_3$. A viscous oil is obtained by evaporation of the solvents in vacuo. This oil is dissolved in ether and treated with ethereal HCl to precipitate a gum which is collected by decantation. This gum is dissolved in warm ethanol and ether is added to induce crystallization. The crystals are collected and washed with ether.

Anal. Calcd. for $C_{29}H_{34}N_{O4}S.HCl$: C, 60.99; H, 6.18; N, 9.81 Found: C, 60.69; H, 6.16; N, 9.69 mp 185°–187° C.; MS (CI) 535 (M+1)

EXAMPLE 68

Methyl Z-4-[[2-butyl-5-[[1-butyl-3-[(2-methyl-4-thiazolyl)methyl]-2,5-dioxo-4-imidazolidinylidene]methyl]-1H-imidazol-1-yl]methyl]benzoate dihydrochloride To a solution of methyl Z-4-[[2-butyl-5-[(1-butyl-2,5-dioxo-4-imidazolidinylidene)methyl]-1H-imidazol-1-yl]methyl]benzoate hydrochloride (0.474 g, 1.0 mmol) in DMF (5 mL) is added $K_2CO_3$ (2.0 g, 15 mmol). After stirring for 5 minutes 2-methyl-4-(chloromethyl)-thiazole hydrochloride (0.184 g, 1.0 mmol) is added. An additional amount of DMF (10 mL) is added after stirring for 30 minutes. The mixture is stirred for 5 days and then filtered. The filtrate is concentrated in vacuo and dissolved in ether (50 mL). This solution is washed with water and dried over $K_2CO_3$ and charcoal. A viscous oil is obtained by evaporation of the solvents in vacuo which is dissolved in ether and treated with ethereal HCl and then evaporated in vacuo to afford a solid foam. Recrystallized from 2-propanol/ether. Anal. Calcd. for $C_{29}H_{35}N_5O_4S$. 2HCl.0.5 $H_2O$: C, 55.14; H, 6.07; N, 11.08 Found: C, 55.00; H, 6.20; N, 11.09 mp 124°–127° C.; MS (CI) 550 (M+1)

EXAMPLE 69

Methyl Z-4-[[2-butyl-5-[[1-butyl-3-[(3,5-dimethyl-4-isoxazolyl)-methyl]-2,5-dioxo-4-imidazolidinylidene]methyl]-1H-imidazol-1-yl]methyl]benzoate monohydrochloride To a solution of methyl Z-4-[[2-butyl-5-[(1-butyl-2,5-dioxo-4-imidazolidinylidene)methyl]-1H-imidazol-1-yl]methyl]benzoate (1.00 g, 2.281 mmol) in DMF (10 mL) is added $K_2CO_3$ (1.580 g, 0.011 moles). After stirring for 15 minutes 4-chloromethyl-3,5-dimethylisoxazole (0.35 g, 2.39 mmol) is added. The mixture is stirred for 24 hours. The solvents were removed under high vacuum. After diluting with ethyl acetate and washing with water and brine the solution is dried over $MgSO_4$. Evaporation in vacuo affords a viscous oil which is dissolved in ether and treated with ethereal HCl to afford a foamy solid upon evaporation in vacuo. This solid is crystallized from ethyl acetate/hexane.

Anal. Calcd. for $C_{30}H_{37}N_5O_5.HCl$: C, 61.69; H, 6.56; N, 11.99 Found: C, 61.40; H, 6.58; N, 11.86 mp 146°–148° C.; MS (CI) 548 (M+1)

EXAMPLE 70

Methyl Z-4-[[2-butyl-5-[[1-butyl-3-(2-naphthalenylmethyl)-2,5-dioxo-4-imidazolidinylidene]methyl]-1H-imidazol-1-yl]methyl]benzoate monohydrochloride To a solution of methyl Z-4-[[2-butyl-5-[[1-butyl-2,5-dioxo-4-imidazolidinylidene]methyl]-1H-imidazol-1-yl]methyl]benzoate (1.00 g, 2.281 mmol) in DMF (10 mL) is added $K_2CO_3$ (1.580 g, 0.011 moles). After stirring for 15 minutes 1-bomomethylnaphthalene (0.53 g, 2.40 mmol) is added. The mixture is stirred for 24 hours then the solvents were removed under high vacuum. After diluting with ethyl acetate and washing with water and brine the solution is dried over $MgSO_4$. Evaporation in vacuo affords a viscous oil which is dissolved in ether and treated with ethereal HCl to afford a foamy solid upon evaporation in vacuo. This solid is crystallized from ethyl acetate/ether.

Anal. Calcd. for $C_{35}H_{38}N_4O_4.HCl.2H_2O$: C, 64.55; H, 6.66; N, 8.60 Found: C, 64.74; H, 6.51; N, 8.47 mp 93°–95° C.; MS (CI) 579 (M+1)

EXAMPLES 71a AND 71b

71a

Z-N-[4-[[2-butyl-5-[(3-butyl-2,5-dioxo-4-imidazolidinylidene)methyl]-1H-imidazol-1-1yl]methyl]phenyl]-1,1,1,-trifluoromethanesulfonamide To a solution of diethyl 3-butyl-2,5-dioxo-4-imidazolylphosphonate (1.48 g, 5.06 mmol) in ethanol (10 mL) was cautiously added sodium hydride batchwise (1.0 g, 25 mmol). The cloudy solution was stirred for 30 min. the aldehyde 1,1-dimethylethyl 4-[(2-butyl-5-formyl-1H-imidazol-1-yl)methyl]benzoate (0.68 g, 1.75 mmol) in ethanol (10 mL) was added over 30 min. This solution was heated at reflux for 2 hours. The reactin was cooled to room temperature and treated with glacial acetic acid (2 mL). Evaporation in vacuo affords a thick gel. Chromatography eluting with 0–4% methanol in chloroform affords the required Z-isomer Anal. Calcd. for $C_{23}H_{28}N_5O_4.0.25H_2O$: C 51.92; H, 5.40; N, 13.16 Found: C, 51.99; H, 5.62; N, 12.85 mp 171°–5° C.; MS (CI) 528 (M+1) and then the more polar E-isomer

71b

E-N-[4-[[2-butyl-5-[(3-butyl-2,5-dioxo-4-imidazolidinylidene)methyl]-1H-imidazol-1-yl]methyl]-phenyl]-1,1,1-trifluoromethanesulfonamide Anal. Calcd. for $C_{23}H_{28}N_5O_4.0.25H_2O$.: C, 51.92; H, 5.40; N, 13.16 Found: C, 51.92; H, 5.41; N, 13.50 mp 177°–178° C.; MS (CI) 528 (M+1)

EXAMPLE 72

Methyl Z-4-[[2-butyl-5-[[1-butyl-3-[(3-methyl-2-thienyl)methyl]-2,5-dioxo-4-imidazolidinylidene]methyl]-1H-imidazol-1-yl]methyl]benzoate hydrochloride To a solution of methyl Z-4-[[2-butyl-5-[[1-butyl-2,5-dioxo-4-imidazolidinylidene]methyl]-1H-imidazol-1-yl]methyl]benzoate (1.10 g, 2,876 mmol) in dry THF (20 mL) was carefully added sodium hydride (0.14 g, 4.67 mmol) and then the mixture was allowed to stir for 20 minutes. 2-Bromomethyl-3-methyl-thiophene (0.75 g, 3.925 mmol) in THF (10 mL) was added dropwise over 10 minutes. After stirring for 2 hours dilute aqueous HCl was added to the orange brown mixture until the pH was 7. This mixture was extracted with ethyl acetate and then dried over $MgSO_4$. The product was isolated by chromatography eluting with acetone in methylene chloride. The hydrochloride salt was prepared by the addition of HCl in isopropanol, and then crystallisation from THF/ether.

Anal. Calcd. for $C_{30}H_{36}N_4O_3S.1.14HCl$: C, 61.05; H, 6.34; N, 9.49 Found: C, 60.67; H, 6.05; N, 9.27 mp 160°–162° C.; MS (CI) 549 (M+1)

EXAMPLE 73

Z-4-[[2-butyl-5-[(1,3-dibutyl-2,5-dioxo-4-imidazolidinylidene)methyl]-1H-imidazol-1-yl]methyl]-benzoic acid 1,1-dimethylethyl Z-4-[[2-butyl-5-[(1,3-dibutyl-2,5-dioxo-4-imidazolidinylidene)methyl]-1H-imidazol-1-yl]methyl]benzoate (0.88 g, 1.64 mmol) was dissolved in methylene chloride (16 mL) and trifluoroacetic acid (16 mL). After stirring for 3 hours the reaction mixture was evaporated in vacuo. Dilute $NaHCO_3$ was added to adjust the pH to 6 and extracted with ethyl acetate. This extract was dried over $MgSO_4$ and then evaporated in vacuo and purified via chromatography (eluant methanol in chloroform).

Anal. Calcd. for $C_{27}H_{36}N_4O_4$: C, 67.48; H, 7.55; N, 11.66 Found: C, 67.48; H, 7.76; N, 11.48 mp 182°–184° C.; MS (CI) 481 (M+1)

EXAMPLE 74

Z-4-[[2-butyl-5-[[1-butyl-3-[(5-methyl-2-thienyl)methyl]-2,5-dioxo-4imidazolidinylidene]methyl]-1H-imidazol-1-yl]methyl]benzoic acid 1,1-dimethylethyl Z-4-[[2-butyl-5-[[1-butyl-3-[(5-methyl-2-thienyl)methyl]-2,5-dioxo-4-imidazolidinylidene]methyl]-1H-imidazol-1-yl]methyl]-benzoate (0.56 g, 0.948 mmol) was dissolved in methylene chloride (10 mL) and trifluoroacetic acid (5 mL). After stirring for 16 hours the reaction mixture was evaporated in vacuo. pH 7 buffer was added and the mixture extracted with ethyl acetate. This extract was dried over $MgSO_4$ and then evaporated in vacuo and crystallized from THF/ether.

Anal. Calcd. for $C_{29}H_{34}N_4O_4S.0.3H_2O$: C, 65.15; H, 6.41; N, 10.48 Found: C, 64.46; H, 6.62; N, 10.39 mp 163°–165° C.; MS (CI) 535 (M+1)

EXAMPLE 75

Z-4-[[2-butyl-5-[[1-butyl-2,5-dioxo-3-(2-thienylmethyl)-4-imidazolidinylidene]methyl]-1H-imidazol-1-yl]methyl]benzoic acid 1,1-dimethylethyl Z-4-[[2-butyl-5-[[1-butyl-2,5-dioxo-3-[(2-thienyl)methyl]-4-imidazolidinylidene]methyl]-1H-imidazol-1-yl]methyl]-benzoate (1.28 g, 2.26 mmol) was dissolved in methylene chloride (25 mL) and trifluoroacetic acid (3.3 mL). After stirring for 16 hours an additional amount of trifluoroacetic acid (3 mL) was added. Stirred for a further 6 hours and then the reaction mixture was evaporated in vacuo. pH 7 buffer was added and the mixture extracted with ethyl acetate.

This extract was dried over MgSO$_4$ and then evaporated in vacuo and crystallized from ethyl acetate/ether.

Anal. Calcd. for C$_{28}$H$_{32}$N$_4$O$_4$S.O0.5H$_2$O: C, 63.50; H, 6.28; N, 10.58 Found: C, 63.58; H, 6.16; N, 10.44 mp 167°–170° C.; MS (CI) 521 (M+1)

EXAMPLES 76a AND 76b

76a

Z-1-Butyl-5-[[2-butyl-3-[[4-(1H-tetrazol-5-yl)phenyl]-methyl]-3H-imidazol-4-yl]methylene]-2,4-imidazolidinedione To a solution of diethyl 3-butyl-2,5-dioxo-4-imidazolylphosphonate (0.240 g, 0.86 mmol) in ethanol (10 mL) was added sodium hydride (0.072 g, 1.80 mmol) and the mixture stirred for 15 minutes. The aldehyde 2-butyl-1-[4-[1-(triphenylmethyl)tetrazol-5-yl)phenyl]-methyl]-5-formylimidazole (0.400 g, 0.72 mmol) was added along with methylene chloride (5 mL). The mixture was stirred for 16 hours. The solvents were removed in vacuo and the Z-isomer and E-isomer purified by chromatography eluting with 20% ethyl acetate in methylene chloride. The Z-isomer and the E-isomer were each separately dissolved in methanol (5 mL) containing a 10% aqueous solution of citric acid (0.5 mL). The reaction mixture was refluxed overnight. Water (20 mL) was added and extracted with hexane. The mixture was then extracted with ethyl acetate and washed with brine and dried over MgSO$_4$. After evaporating in vacuo the residue was crytallized from a combination of hexane, ethyl acetate and methanol.

Anal. Calcd. for C$_{23}$H$_{28}$N$_8$O$_2$S.0.9H$_2$O: C, 59.40; H, 6.47; N, 24.09 Found: C, 59.79; H, 6.18; N, 23.57 mp 140°–142° C.; MS (CI) 449 (M+1)

76b

E-1-Butyl-5-[[2-butyl-3-[[4-(1H-tetrazol-5-yl)phenyl]-methyl]-3H-imidazol-4-yl]methylene]-2,4-imidazolidinedione Anal. Calcd. for C$_{23}$H$_{28}$N$_8$O$_2$S.1.67H$_2$O: C, 57.72; H, 6.60; N, 23.41 Found: C, 57.35; H, 5.94; N, 23.13 MS (CI) 449 (M+1)

EXAMPLE 77

Methyl Z-4-[[5-[[3-[(5-bromo-2-thienyl)methyl]-1-butyl-2,5-dioxo-4-imidazolidinylidene]methyl]-2-butyl-1H-imidazol-1-yl]methyl]benzoate monohydrochloride To a solution of methyl Z-4-[[2-butyl-5-[(1-butyl-2,5-dioxo-4-imidazolidinylidene)methyl]-1H-imidazol-1-yl]methyl]benzoate (0.750 g, 1.7 retool) in DMF (10 mL) was added K$_2$CO$_3$ (1.17 g, 0.0085 moles). 2-bromomethyl-5-bromothiophene (0.46 g, 0.0018 moles) was added in one portion and the mixture stirred for 16 hours. The reaction mixture was filtered and evaporated in vacuo. The residue was extracted into ethyl acetate and then washed with water and brine. After drying over MgSO$_4$ and evaporation in vacuo the residue was purified by chromatography eluting with 10% ethyl acetate in methylene chloride. The required product was recrystallized as its hydrochloride salt.

Anal. Calcd. for C$_{29}$H$_{33}$N$_4$O$_4$BrS.HCl.0.72H$_2$O: C, 52.54; H, 5.39; N, 8.45 Found: C, 52.54; H, 5.51; N, 8.42 MS (CI) 613/615 (M+1)

EXAMPLE 78

Methyl Z-4-[[5-[[3-[(4-bromo-2-thienyl)methyl]-1-butyl-2,5-dioxo-4-imidazolidinylidene]methyl]-2-butyl-1H-imidazol-1-yl]methyl]benzoate monohydrochloride To a solution of methyl Z-4-[[2-butyl-5-[(1-butyl-2,5-dioxo-4-imidazolidinylidene)methyl]-1H-imidazol-1-yl]methyl]benzoate (0.750 g, 1.7 retool) in DMF (10 mL) was added K$_2$CO$_3$ (1.17 g, 0.0085 moles). 2-bromomethyl-4-bromothiophene (0.46 g, 0.0018 moles) was added in one portion and the mixture stirred for 16 hours. The reaction mixture was filtered and evaporated in vacuo. The residue was extracted into ethyl acetate and then washed with water and brine. After drying over MgSO$_4$ and evaporation in vacuo the residue was dissolved in ether and treated with ethereal HCl to afford a white solid upon removal of solvents in vacuo.

Anal. Calcd. for C$_{29}$H$_{33}$N$_4$O$_4$BrS.HCl.1.22H$_2$O: C, 51.83; H, 5.47; N, 8.34 Found: C, 51.82; H, 5.32; N, 8.18 MS (CI) 613/615 (M+1)

EXAMPLE 79

Methyl Z-4-[[2-butyl-5-[[1-butyl-2,5-dioxo-3-[2(2-thienyl)ethyl]-4-imidazolidinylidene]methyl]-1H-imidazol-1-yl]methyl]benzoate monohydrochloride To a solution of methyl Z-4-[[2-butyl-5-[(1-butyl-2,5-dioxo-4-imidazolidinylidene)methyl]-1H-imidazol-1-yl]methyl]benzoate (0.750 g, 1.7 mmol) in DMF (20 mL) was added K$_2$CO$_3$ (1.17 g, 0.0085 moles). 2-(2-thienyl) ethyl bromide (0.35 g, 0. 0018 moles) was added in one portion and the mixture stirred for 16 hours. The reaction mixture was filtered and evaporated in vacuo. The residue was extracted into ethyl acetate and then washed with water and brine. After drying over MgSO$_4$ and evaporation in vacuo the residue was purified by chromatography eluting with 50% ethyl acetate in methylene chloride. The required product was dissolved in ether and treated with ethereal HCl to afford a white solid upon removal of solvents in vacuo.

Anal. Calcd. for C$_{30}$H$_{37}$N$_4$O$_4$S.HCl.1.15H$_2$O: C, 59.47; H, 6.54; N, 9.25 Found: C, 59.48; H, 6.48; N, 9.01 MS (CI) 549 (M+1)

EXAMPLE 80

Methyl Z-4-[[2-butyl-5-[[1-butyl-2,5-dioxo-3-[2-(3-thienyl)ethyl]-4-imidazolidinylidene]methyl]-1H-imidazol-1-yl]methyl]benzoate monohydrochloride To a solution of methyl Z-4-[[2-butyl-5-[1-butyl-2,5-dioxo-4-imidazolidinylidene]methyl]-1H-imidazolyl]-methyl]benzoate (0.750 g, 1.7 retool) in DMF (20 mL) was added K$_2$CO$_3$ (1.17 g, 0.0085 moles). 2-(3-thienyl) ethyl bromide (0.35 g, 0. 0018 moles) was added in one portion and the mixture stirred for 16 hours. A further amount of 2-(3-thienyl)ethyl bromide (0.35 0.0018 moles) was added and the mixture stirred for 16 hours. The reaction mixture was filtered and evaporated in vacuo. The residue was extracted into ethyl acetate and then washed with water and brine. After drying over MgSO$_4$ and evaporation in vacuo the residue was purified by chromatography eluting with 20% ethyl acetate in methylene chloride. The required product was dissolved in ether and treated with ethereal HCl to afford a white solid upon removal of solvents in vacuo.

Anal. Calcd. for $C_{30}H_{37}N_4O_4S.HCl.0.87H_2O$: C, 59.97; H, 6.50; N, 9.32 Found: C, 59.99; H, 6.40; N, 9.27 MS (CI) 549 (M+1)

EXAMPLE 81

Methyl Z-4-[[5-[[3-[(5-bromo-3-thienyl)methyl]-1-butyl-2,5-dioxo-4-imidazolidinylidene]methyl]-2-butyl-1H-imidazol-1-yl]methyl]benzoate monohydrochloride To a solution of methyl Z-4-[[2-butyl-5-[(1-butyl-2,5-dioxo-4-imidazolidinylidene)methyl]-1H-imidazol-1-yl]methyl]benzoate (0.500 g, 1.1 retool) in DMF (20 mL) was added $K_2CO_3$ (0.76 g, 0.0055 moles). 2-bromo-3-bromomethylthiophene (0.44 g, 0.0017 moles) was added in one portion and the mixture stirred for 16 hours. The reaction mixture was filtered and evaporated in vacuo. The residue was extracted into ethyl acetate and then washed with water and brine. After drying over $MgSO_4$ and evaporation in vacuo the residue was purified by chromatography eluting with 20% ethyl acetate in methylene chloride. The required product was dissolved in ether and treated with ethereal HCl to afford a white solid upon removal of solvents in vacuo.

Anal. Calcd. for $C_{29}H_{34}N_4O_4SBrCl.HCl.1.56H_2O$: C, 51.32; H, 5.52; N, 8.26 Found: C, 51.32; H, 5.48; N, 8.15 MS (CI) 613/615 (M+1)

EXAMPLE 82

Methyl Z-4-[[2-butyl-5-[[1-butyl-2,5-dioxo-3-(4-thiazolylmethyl)-4-imidazolidinylidene]methyl]-1H-imidazol-1-yl]methyl]benzoate monohydrochloride To a solution of methyl Z-4-[[2-butyl-5-[(1-butyl-2,5-dioxo-4-imidazolidinylidene)methyl]-1H-imidazol-1-yl]methyl]benzoate (0.750 g, 1.7 mmol) in DMF (20 mL) was added sodium hydride (60%) (0.17 g, 0.0043 moles). 4-chloromethylthiazole hydrochloride (0.22 g, 0.0013 moles) was added in one portion and the mixture stirred for 64 hours. The reaction mixture was filtered and evaporated in vacuo. The residue was extracted into ethyl acetate and then washed with water and brine. After drying over $MgSO_4$ and evaporation in vacuo the residue was purified by chromatography eluting with 20% ethyl acetate in methylene chloride. The required product was dissolved in ether and treated with ethereal HCl to afford a white solid upon removal of solvents in vacuo.

Anal. Calcd. for $C_{29}H_{34}N_4O_4SBrCl.HCl$: C, 58.62; H, 6.16; N, 12.22; Found: C, 57.84; H, 6.09; N, 11.84; MS (CI) 536 (M+1)

EXAMPLE 83

Methyl Z-1-[4-[[2-butyl-5-[(1-butyl-2,5-dioxo-4-imidazolidinylidene)methyl]-1H-imidazol-1-yl]methyl]phenyl]cyclopentanecarboxylate Methyl Z-1-[4-[(2-butyl-5-formyl-1H-imidazol-1-yl)methyl]phenyl]cyclopentanecarboxylate was added to a solution of 3-butyl-2,5-dioxo-4-imidazolylphosphonate (2.42 g, 9.00 mmol) and DBU (1.31 g, 8.6 mmol) in methylene chloride (10 mL). This mixture was allowed to stand for 16 h at room temperature. This mixture was then purified by chromatography, eluant (1-10)% methanol in chloroform, and recrystallisation from hot ethyl acetate and ether. 1H-NMR indicated a small amount of the E-isomer was present in the purified Zisomer fraction.

Anal. Calcd. for $C_{29}H_{38}N_4O_4$: C, 68.75; H, 7.56; N, 11.06 Found: C, 68.63; H, 7.55; N, 10.98 MS (CI) 507 (M+1)

EXAMPLE 84

Methyl Z-1-[4-[[2-butyl-5-[[1-butyl-[3(2-methyl-4-thiazoly)-methyl]-2,5-dioxo-4-imidazolidinylidene]methyl]-1H-imidazol-1-yl]methyl]phenyl]cyclopentane-carboxylate monohydrochloride Methyl Z-1-[4-[[2-butyl-5-[[1-butyl-2,5-dioxo-4-imidazol idinylidene]methyl]-1H-imidazol-1-yl]methyl]phenyl]cyclopentanecarboxylate (1.00 g, 1.97 mmol) and 4-chloromethyl-2-methylthiazole monohydrochloride (0.363 g, 1.97 mmol) were dissolved in DMF (10 mL). $K_2CO_3$ (3.0 g, 21.7 mmol) was added and the mixture stirred for 16 hours. The mixture was filtered and evaporated. The residue was added to water and the gum that formed was dissolved in ether. After washing the ethereal fraction with water and drying over $K_2CO_3$ the product was purified by chromatography, eluant (0.5–3 ) % methanol in chloroform. The appropriate fraction was dissolved in ether and treated with ethereal HCl. The solid foam that resulted upon extended evaporation in vacuo was collected and shown by 1H NMR to contain the required product as well as the corresponding E-isomer (10%).

Anal. Calcd. for $C_{34}H_{43}N_5O_4S.HCl.H_2O$: C, 60.74; H, 6.90; N, 10.42 Found: C, 61.09; H, 6.78; N, 10.48 MS (CI) 618 (M+1)

EXAMPLE 85

Z-1-[4-[[2-butyl-5-[[1-butyl-3-(2-methyl-4thiazoly)methyl]-2,5-dioxo-4-imidazolidinylidene]methyl]-1H-imidazol-1-yl]methyl]phenyl]cyclopentanecarboxylic acid Methyl Z-1-[4-[[2-butyl-5-[[1-butyl-2,5-dioxo-[3(2-methyl-4-thiazoly) methyl ]-4 imidazolidinylidene]methyl]-1H-imidazol-1-yl ]methyl]phenyl]cyclopentanecarboxylate monohydrochloride (0.340 g, 0.5 mmol) and 2N HCl (15 mL) were heated at reflux for 2 hours. After evaporation in vacuo the residue was dissolved in methanol and treated with saturated aqueous NaOAc to precipitate a gum. This gum crystallized from ethyl acetate and was then recrystallized from methanol.

Anal. Calcd. for $C_{33}H_{41}N_5O_4S$: C, 65.65; H, 6.84; N, 11.60 Found: C, 65.43; H, 6.74; N, 11.22 MS (CI) 604 (M+1)

EXAMPLE 86

Methyl E-4-[[2-butyl-5-[[3-butyl-1-[(2-methyl-4-thiazolyl)methyl]-2,5-dioxo-4-imidazolidinylidene]methyl]-1H-imidazol-1-yl]methyl]benzoate dihydrochloride To a solution of methyl E-4-[[2-butyl-5-[(3-butyl-2,5-dioxo-4-imidazolidinylidene)methyl]-1H-imidazol-1-yl]methyl]benzoate (0.66 g, 1.5 mmol) in DMF (10 mL) is added $K_2CO_3$ (3.0 g, 15 mmol). After stirring for 5 minutes 2-methyl-4-chloromethylthiazole hydrochloride (0.28 g, 1.5 mmol) is added. The mixture is stirred for 16 hours and then filtered. The filtrate is concentrated in vacuo and dissolved in ether (50 mL). This solution is washed with water and dried over K$_2$CO$_3$ and charcoal. The mixture is filtered and allowed to stand in which time the product crystallizes. Petroleum ether is added to complete crystallization.

Anal. Calcd. for C$_{29}$H$_{35}$N$_5$O$_4$S: C, 63.37; H, 6.42; N, 12.74 Found: C, 63.46; H, 6.38; N, 12.72 mp 109°–111° C.; MS (CI) 550 (M+1)

EXAMPLES 87a AND 87b

Methyl Z-4-[[2-butyl-5-[(3-butyl-2,5-dioxo-4-imidazolidinylidene)methyl]-1H-imidazol-1-yl]methyl]-3-chlorobenzoate To a solution of diethyl 3-butyl-2,5-dioxo-4-imidazolylphosphonate (0.49 g, 1.72 mmol) in acetonitrile (5 mL) was added lithium chloride (0.15 3.47 mmol) and then DBU (0.52 mL, 3.47 mmol). This mixture was stirred for 5 minutes under N$_2$. Methyl 4-[(2-butyl-5-formyl-1H-imidazol-1-yl)methyl]-3-chlorobenzoate (0.48 g, 1.43 mmol) in acetonitrile (5 mL) was added and the mixture stirred for 4 days. The solvent was removed in vacuo and the isomers separated by chromatography eluting with (1–5)% methanol in chloroform.

Anal. Calcd. for C$_{24}$H$_{29}$N$_4$O$_4$Cl: C, 60.95; H, 6.18; N, 11.85 Found: C, 60.50; H, 6.11; N, 11.30 MS (CI) 473 (M+1)

87b

Methyl E-4-[[2-butyl-5-[[3-butyl-2,5-dioxo-4-imidazolidinylidene[methyl]-1H-imidazol-1-yl]methyl-3-chlorobenzoate Anal. Calcd. for C$_{24}$H$_{29}$N$_4$O$_4$Cl: Cl: C, 60.95; H, 6.18; N, 11.85
Found: C, 60.47; H, 6.06; N, 11.23 mp 186°–187° C.; MS (CI) 473 (M+1)

EXAMPLES 88a AND 99b

88a

Methyl Z-1-[4-[[4-[[2-butyl-5-[(3-butyl-2,5-dioxo-4-imidazolidinylidene)methyl]-1H-imidazol-1-yl]methyl]phenyl]cyclohexanecarboxylate Methyl Z-1-[4-[(2-butyl-5-formyl-1H-imidazol-1-yl)methyl]phenyl]cyclohexanecarboxylate was added to a solution of 3-butyl-2,5-dioxo-4-imidazolylphosphonate (0.16 g, 0.58 mmol) and sodium hydride (80% in oil) (0.032 g, 1.16 mmol) in methanol (3 mL). This mixture was allowed to stir for 16 hours at room temperature. This mixture was then purified by chromatography, eluant (1–10)% methanol in chloroform. The Z-isomer was separated from the E-isomer.

Anal. Calcd. for C$_{30}$H$_{40}$N$_4$O$_4$: C, 69.20; H, 7.74; N, 10.76 Found: C, 68.85; H, 7.67; N, 10.46 mp 139°–140° C.; MS (CI) 521 (M+1)

88b

Methyl E-1-[4-[[2-butyl-5-[[3-butyl-2,5dioxo-4-imidazolidinylidene]methyl]-1H-imidazol-1-yl]methyl]-phenyl]cyclohexanecarboxylate Anal. Calcd. for C$_{30}$H$_{40}$N$_4$O$_4$: C, 69.20; H, 7.74; N, 10.76 Found: C, 68.90; H, 7.80; N, 10.55 mp 189°–190° C.; MS (CI) 521 (M+1)

EXAMPLE 89

Methyl Z-4-[[2-butyl-5-[[1-(cyclopropylmethyl)-2,5-dioxo-3-(2-thienylmethyl)-4-imidazolidinylidene]methyl]-1H-imidazol-1-yl]methyl]benzoate monohydrochloride To a solution of methyl Z-4-[[2-butyl-5-[(1-cyclopropylmethyl-2,5-dioxo-4-imidazolidinylidene)methyl]-1H-imidazol-1-yl]methyl]benzoate (0.39 g, 0.89 mmol) in DMF (5 mL) is added K$_2$CO$_3$ (0.67 g, 4.47 mmol). After stirring for 5 minutes 3-bromomethylthiophene (1.20 mmol) is added. The mixture is stirred for 16 hours. The mixture is diluted with ethyl acetate and washed with water and dried over MgSO$_4$. After purification by chromatography, eluting with (0–40)% ethyl acetate in methylene chloride, the hydrochloride is prepared by the addition of ethereal HCl. The product is crystallized from ethyl acetate.

Anal. Calcd. for C$_{29}$H$_{32}$N$_4$O$_4$S: C, 61.20; H, 5.84; N, 9.84 Found: C, 61.07; H, 5.82; N, 9.50 mp 184°–190° C.; MS (CI) 533 (M+1)

EXAMPLE 90

Methyl E-4-[[5-[(3-butyl-1-methyl-2,5-dioxo-4-imidazolidinylidene)methyl]-2-propyl-1H-imidazol-1-yl]methyl]benzoate monohydrochloride To a solution of methyl E-4-[[5-[(3-butyl-2,5dioxo-4-imidazolidinylidene)methyl]-2-propyl-1H-imidazol-1-yl]methyl]benzoate (0.082 g, 0.07 mmol) in DMF (0.5 mL) is added K$_2$CO$_3$ (0.50 g, 3.62 retool) and then methyliodide (0.024 g, 0.17 mmol). After stirring for 1 hour a further amount of 1-iodomethane is added (0.024 g, 0.17 mmol). The mixture is stirred for an additional 1 hour. The mixture is diluted with water and the gum that precipitates is collected by decantation. This gum is dissolved in methylene chloride and treated with charcoal and K$_2$CO$_3$. This mixture is filtered, concentrated and crystallized from ether.

Anal. Calcd. for C$_{24}$H$_{30}$N$_4$O$_4$ 0.3H$_2$O: C, 65.20; H, 6.93; N, 12.67 Found: C, 65.16; H, 6.88; N, 12.60 mp 113°–114° C.; MS (CI) 439 (M+1)

EXAMPLE 91

Z-1-Butyl-5-[[2-butyl-3-[[2'-(1H-tetrazol-5-yl)[1,1'-biphenyl]-4-yl]methyl]-3H-imidazol-4-yl]methylene]-2,4-imidazolidinedione To Z-1-butyl-5-[[2-butyl-3-[[2'-(N-triphenylmethyl-tetrazol-5-yl)[1,1'-biphenyl]-4-yl]methyl]3H-imidazol-4-yl]methylene]-2,4-imidazolidinedione (0.800 g, 1.04 mmol) was added methanol (100 mL) and 5% aqueous citric acid (5 mL). This white heterogeneous mixture was refluxed for 3 hour in which time a solution formed. The solution was cooled to room temperature and diluted with water (10 mL) and hexanes (100 mL). The aqueous methanol fraction was evaporated in vacuo and then dissolved in a mixture of ethyl acetate and water. After drying the organic fraction over Na$_2$SO$_4$ the product was precipitated by the addition of ether to a methylene chloride solution.

HPLC eluant 55%(0.1%TFA in H$_2$O) 45% MeCN, RT 2.98[99%] MS (CI) 525 (M+1)

EXAMPLE 92

E-1-Butyl-5-[[2-butyl-3-[[2'-(1H-tetrazol-5-yl)[1,1'-biphenyl ]-4-yl]methyl]-3H-imidazol-4-yl]methylene-2,4-imidazolidinedione To E-1-butyl-5-[[2-butyl-3-[[2'-(N-triphenylmethyl-tetrazol-5-yl)[1,1'-biphenyl]-4-yl]methyl ]-3H-imidazol-4-yl]methylene]-2,4-imidazolidinedione (0.100 g, 0.13 mmol ) was added methanol (50 mL) and 5% aqueous citric acid (5 mL). This white heterogeneous mixture was refluxed for 3 hour in which time a solution formed. The solution was cooled to room temperature and diluted with water (10 mL) and hexanes (100 mL). The aqueous methanol fraction was evaporated in vacuo and then dissolved in a mixture of ethyl acetate and water. After drying the organic fraction over Na$_2$SO$_4$ the solvents were removed in vacuo and the residue triturated with hexanes. HPLC eluant 45%(0.1%TFA in H$_2$O) 55% MeCN, RT 2.25[95%] MS (CI) 525 (M+1)

EXAMPLE 93

Z-5-[[2-butyl-3-[[2'-(1H-tetrazol-5-yl)[1,1'-biphenyl]-4-yl]methyl]-3H-imidazol-4-yl]methylene]1-methyl-2,4-imidazolidinedione To Z-5-[[2-butyl-3-[[2'-(N-triphenyl-methyltetrazol-5-yl)[1,1'-biphenyl]-4-yl]methyl]-3H-imidazol-4-yl]methylene]-1-methyl -2,4-imidazolidinedione (0.300 g, 0.414 mmol) was added methanol (50 mL) and glacial acetic acid (0.2 mL). This white heterogeneous mixture was refluxed for 4 hours in which time a solution formed. The solution was cooled to room temperature and diluted with water (5 mL) and hexanes (50 mL). The aqueous methanol fraction was evaporated in vacuo and then dissolved in a minimal amount of methanol. Ether was added to precipitate a white solid.

Anal. Calcd. for C$_{26}$H$_{26}$N$_8$O$_2$0.67H$_2$O: C, 63.16; H, 5.57; N, 22.66 Found: C, 63.43; H, 5.66; N, 22.33 HPLC eluant 67%(0.1%TFA in H$_2$O) 33% MeCN, RT 4.4[92%] MS (CI) 483 (M+1)

EXAMPLE 94

E-5-[[2-butyl-3-[[2'-(1H-tetrazol-5-yl)[1,1'-biphenyl]-4-yl]methyl]-3H-imidazol-4-yl]methylene]1-methyl-2,4-imidazolidinedione To a mixture of the E and Z-isomers of 5-[[2-butyl-3-[[2'-(N-triphenylmethyl-tetrazol-5-yl) [1,1'-biphenyl]-4-yl]methyl]-3H-imidazol-4-yl]methylene]-1-methyl-2,4-imidazolidinedione (0.400 g, 0.552 mmol ) was added methanol (50 mL) and glacial acetic acid (0.2 mL). This white heterogeneous mixture was refluxed for 3 hour in which time a solution formed. The solution was cooled to room temperature and diluted with water (5 mL) and hexanes (50 mL). The aqueous methanol fraction was evaporated in vacuo and then triturated with ethyl acetate. The insoluble residue was collected and determined to be the E-isomer. HPLC eluant 45%(0.1%TFA in H$_2$O) 55% MeCN, RT 1.9[95%] MS (CI) 483 (M+1)

EXAMPLE 95

1-Butyl-5-[[2-butyl-3-[[2'-(1H-tetrazol-5-yl)[1,1'-biphenyl]-4yl]methyl]-3H-imidazol-4-yl]methyl]-2,4-imidazolidinedione To a solution of 1-butyl-5-[[2-butyl-3-[[2'-(N-triphenylmethyl-tetrazol-5-yl)[1,1'-biphenyl]-4-yl ]methyl]-3H-imidazol-4-yl]methyl]-2,4-imidazolidinedione (0.080 g, 0.10 mmol ) in methanol (30 mL) was added glacial acetic acid (0.06 mL). This mixture was refluxed for 5 hours. The solution was cooled to room temperature and diluted with water (10 mL) and hexanes (50 mL). The aqueous methanol fraction was evaporated in vacuo and then redissolved in a minimum volume of methanol. Ether was added and the solid that precipitated collected.

HPLC eluant 67%(0.1%TFA in $_2$O) 33% MeCN, RT 5.4[98%] MS (CI) 527 (M+1)

Anal. Calcd. for C$_{29}$H$_{34}$N$_8$O$_2$.H$_2$O: C, 63.95; H, 6.66; N, 20.57 Found: C, 64.15; H, 6.66; N, 20.07

EXAMPLES 96a AND 96a

96a

Methyl Z-4'-[]2-butyl-5-[(3-butyl-2,5-dioxo-4-imidazolidinylidene)methyl]-1H-imidazol-1-yl]methyl][1,1'-biphenyl]-2-carboxylate To a solution of diethyl 3-butyl-2,5-dioxo-4-imidazolylphosphonate (0.540 g, 1.91 mmol) in methanol (15 mL) is added NaH (80% in oil, 0.115 g, 3.83 mmol). The solution is stirred for 5 minutes and then 2-butyl-1-[(2'-carbomethoxy-1,1'-biphen-4-yl)methyl]-1H-imidazole-5-carboxaldehyde (0.515 g, 1.37 mmol) is added. The yellow solution is stirred for 16 hours at room temperature and then diluted with ethyl acetate and saturated ammonium chloride. The organic fraction is washed with brine and then dried over Na$_2$SO$_4$. Chromatography separates the Z and E-isomers, eluant (0–2 ) % methanol in chloroform. Z- isomer Anal. Calcd. for C$_{30}$H$_{34}$N$_4$O$_4$: C, 70.02; H, 6.66; N, 10.89 Found: C, 69.58; H, 6.58; N, 10.55 MS (CI) 515 (M+1)

96a

Methyl E 4'-[[2-butyl-5-[(3-butyl-2,5-dioxo-4-imidazolidinylidene)methyl]-1H-imidazol-1-yl]methyl][1,1'-biphenyl]-2-carboxylate Anal. Calcd. for C$_{30}$H$_{34}$N$_4$O$_4$: C, 70.02; H, 6.66; N, 10.89 Found: C, 69.63; H, 6.54; N, 10.65 MS (CI) 515 (M+1)

EXAMPLES 97a AND 97b

97a

Methyl Z-4'-[[4-bromo-2-butyl-5-[(3-butyl-2,5-dioxo-4-imidazolidinylidene)methyl]-1H-imidazol-1-yl]methyl][1,1'-biphenyl]-2-carboxylate To a solution of diethyl 3-butyl-2,5-dioxo-4-imidazolylphosphonate (0,105 g, 0.372 mmol) in methanol (10 mL) is added sodium hydride (80% in oil, 0,022 g, 0.733 mmol). The solution is stirred for 5 minutes and then 4-bromo-2-butyl-1-[(2'-carbomethoxy-1,1'-biphen-4-yl)methyl]-1H-imidazole-5-carboxaldehyde (0.130 g, 0.286 mmol) is added. The yellow solution is stirred for 16 hours at room temperature and then diluted with ethyl acetate and saturated ammonium chloride. The organic fraction is washed with brine and then dried over $Na_2SO_4$. Chromatography separates the Z and E-isomers, eluant (30–50)% ethyl acetate in hexane.

Anal. Calcd. for $C_{30}H_{33}N_4O_4Br$: C, 60.71; H, 5.60; N, 9.44 Found: C, 60.59; H, 5.71; N, 9.06 MS (CI) 593/595

97b

Methyl E-4'-[[4-bromo-2-butyl-5-[(3-butyl-2,5-dioxo-4-imidazolidinylidene)methyl]-1H-imidazol-1-yl]methyl][1,1'-biphenyl]-2-carboxylate Anal. Calcd. for: $C_{30}H_{33}N_4O_4Br$: C, 60.71; H, 5.60; N, 9.44 Found: C, 60.45; H, 5.48; N, 9.42 MS (CI) 593/595

EXAMPLE 98

Methyl Z-4-[[2-butyl-5-2-[butyl[[(methoxymethyl)amino]carbonyl]amino]-2-carboxyethenyl]-1H-imidazol-yl]methyl]benzoate To a solution of methyl Z-4-[[2-butyl-5-[[3-butyl-1-(methoxymethyl)-2,5-dioxo-4-imidazolidinylidene]methyl]-1H-imidazol-1-yl]methyl]benzoate monohydrochloride. (0. 100 g, 0.193 mmol) in THF was added 1N NaOH (0.22 mL, 0.22 mmol) and then methanol (2 mL). The yellow solution was stirred for 5 hours and then 1 N HCl (0.22 mL, 0.22 mmol) was added. The reaction mixture was evaporated in vacuo to a white solid. This solid was dissolved in ethyl acetate and water. The organic layer was dried briefly over $MgSO_4$ and then concentrated to 1/6 original volume. An equal volume of hexane was added and the solid collected.

Anal. Calcd. for: $C_{26}H_{36}N_4O_6$: C, 62.38; H, 7.25; N, 11.19 Found: C, 61.97; H, 7.17; N,11.15 mp 155° C.; MS (FAB) 501

EXAMPLE 99

Z-4-[[2-butyl-5-[[1-butyl-2,5-dioxo-3-]1-(phenylmethyl)-1H-imidazol-2-yl]methyl-4-imidazolidinylidene]methyl]-1H-imidazol-1-yl]methyl]benzoate To a solution of methyl Z-4-[[2-butyl-5-[(1-butyl-2,5-dioxo-4-imidazolidinylidene) methyl]-1H-imidazol-1-yl]methyl]benzoate hydrochloride (0,190 g, 0.400 mmol) in DMF (1 mL) is added $K_2CO_3$ (0.300 g, 2.17 mmol). After stirring for 5 minutes 1-(phenylmethyl)-2-chloromethyl-1H-imidazole monohydrochloride (0,130 g, 0.53 mmol) is added. The mixture is stirred for 16 hours to generate a brown colored mixture. After diluting with ethyl acetate and washing with water and brine the solution is dried over $MgSO_4$. A viscous oil is obtained upon chromatography on silica gel (eluant 0.5% methanol in chloroform) and evaporation of the solvents in vacuo. This oil is dissolved in ether and treated with ethereal HCl to afford a foamy solid upon evaporation in vacuo. This solid is crystallized from 2-propanol/methanol/ether.

Anal. Calcd. for $C_{35}H_{40}N_6O_4.2HCl. 0.67H2O$: C, 61.67; H, 6.21; N, 12.33 Found: C, 61.06; H, 6.14; N, 11.98 mp 247°–248° C.; MS (EI) 608

EXAMPLE 100

Methyl Z-4-[[2-butyl-5-[[2,5-dioxo-1-[[2-(trimethylsilyl)ethoxy]methyl]-4-imidazolidinylidene]methyl]-1H-imidazol-1-yl]methyl]benzoate To a solution of methyl Z-4-[[2-butyl-5-[(2,5-dioxo-4-imidazolidinylidene)methyl]-1H-imidazol-1-yl]methyl]benzoate (0.200 g, 0.524 mmol) in DMF (2 mL) is added sodium hydride (80% in oil, 0.02 g, 0.67 mmol) and the mixture stirred for 5 minutes. (Trimethylsilyl)ethoxymethyl chloride SEM-Cl (0.100 mL, 0.536 mmol) is added and the mixture allowed to stir for 16 hours. The solvents are removed in vacuo and the residue dissolved in ethyl acetate and water. After drying the organic fraction over $MgSO_4$, the required product is isolated by chromatography, eluting with 0.5% methanol in chloroform. Crystallized from ether.

Anal. Calcd. for $C_{26}H_{36}N_4O_5Si$: C, 60.90; H, 7.08; N, 10.93 Found: C, 60.81; H, 7.09; N, 10.73 mp 146°–148° C.; MS (CI) 513

EXAMPLE 101

Methyl Z-4-[[2-butyl-5-[[1-(hydroxymethyl)-3-[(2-methyl-4-thiazolyl)methyl ]-2,5-dioxo-4-imidazolidinylidene]methyl]-1H-imidazol-1-yl]methyl]benzoate dihydrochloride To a solution of methyl Z-4-[[2-butyl-5-[[2,5-dioxo-1-[[2-(trimethylsilyl)ethoxy]methyl]-4-imidazolidinylidene]methyl]-1H- imidazol-1-yl]methyl]benzoate (0.390 g, 0.760 mmol) in DMF (5 mL) is added $K_2CO_3$ (0.525 g, 3.80 mmol). After stirring for 5 minutes 4-chloromethyl-2-methylthiazole hydrochloride (0.275 g, 1.49 retool) is added. The mixture is stirred for 16 hours. Water is added and the gum that precipitates is separated. This gum is dissolved in ethyl acetate, washed with water and brine, and then dried over $MgSO_4$. Chromatography eluting with 0.5% methanol in chloroform and evaporation in vacuo affords a viscous oil. This oil is dissolved in methylene chloride (5 mL) and treated with trifluoroacetic acid (5 mL). After stirring for 90 minutes the mixture is concentrated in vacuo and then extracted into methylene chloride from pH 7 buffer. The organic phase is dried over $MgSO_4$ and then evaporated in vacuo to afford an oil. This oil is disssolved in 2-propanol and treated with ethereal HCl (1M, 2mL). The white gummy solid that results is crystallized from methanol/2-propanol/ether.

Anal. Calcd. for $C_{26}H_{29}N_5O_5S. 2HCl$: C, 52.35; H, 5.24; N, 11.74 Found: C, 52.25; H, 5.32; N, 11.55 mp 208°–211° C.; MS (CI) 522

EXAMPLE 102

Methyl Z-4-[[5-[[3-[(1,1'-biphenyl)-4-ylmethyl]-1-butyl-2,5-dioxo-4-imidazolidinylidene]methyl]-2-butyl-1H-imidazol-1-yl]methyl]benzoate To a solution of methyl Z-4-[[2-butyl-5-[[1-butyl-2,5-dioxo-4-imidazolidinylidene]methyl]-1H-imidazol-1-yl]methyl]benzoate (0.438 g, 1.00 mmol) in DMF (10 mL) is added $K_2CO_3$ (0.42 g, 3.00 mmol). After stirring for 5 minutes diphenylmethyl chloride (0.210 g, 1.00 mmol) is added. The mixture is stirred for 16 hours, filtered, and evaporated in vacuo. The gum is dissolved in ethyl acetate and washed with water, brine and dried over MgSO$_4$. Chromatography eluting with (50–100)% ethyl acetate in hexane, evaporation in vacuo affords a foam.

Anal. Calcd. for C$_{37}$H$_{40}$N$_4$O$_4$. 0.3H$_2$O: C, 72.84; H, 6.71; N, 9.18 Found: C, 72.73; H, 6.75; N, 9.12 MS (CI) 604

EXAMPLE 103

Methyl Z-4-[[2-butyl-5-[[1-butyl-2,5-dioxo-3-[2-oxo-2-(2-thienyl)ethyl]-4-imidazolidinylidene]methyl]-1H-imidazol-1-yl]methyl]benzoate monochloride To a solution of methyl Z-4-[[2-butyl-5-[(1-butyl-2,5-dioxo-4-imidazolidinylidene)methyl]-1H-imidazol-1-yl]methyl]benzoate (0.660 g, 1.50 mmol) in DMF (10 mL) is added sodium hydride (60% in oil, 0.08 g, 2.0 mmol). After stirring for 5 minutes 2-(bromoacetyl)thiophene (0.500 g, 2.44 mmol) is added. The mixture is stirred for 16 hours, filtered and evaporated in vacuo. The gum is dissolved in ethyl acetate and washed with water, brine and dried over MgSO$_4$. Chromatography eluting with (0–5)% methanol in dichloromethane and evaporation in vacuo affords a foam. The hydrochloride salt is prepared.

Anal. Calcd. for C$_{30}$H$_{34}$N$_4$O$_4$S. HCl. H$_2$O: C, 58.38; H, 6.04; N, 9.08 Found: C, 58.21; H, 5.99; N, 8.74 MS (CI) 563

EXAMPLE 104

Methyl Z-4-[[2-butyl-5-[[1-butyl-2,5-dioxo-3-(2-oxo-2-phenylethyl)-4-imidazolidinylidene]methyl]-1H-imidazol-1-yl]methyl]benzoate monohydrochloride To a solution of methyl Z-4-[[2-butyl-5-[[1-butyl-2,5-dioxo-4-imidazolidinylidene]methyl]-1H-imidazol-1-yl]methyl]benzoate (0.660 g, 1.50 mmol) in DMF (10 mL) is added K$_2$CO$_3$ (0.62 g, 4.5 mmol). After stirring for 5 minutes (bromoacetyl)benzene (0.320 g, 1.6 mmol) is added. The mixture is stirred for 16 hours, filtered, and evaporated in vacuo. The gum is dissolved in ethyl acetate and washed with water, brine and dried over MgSO$_4$. Chromatography eluting with (50–100)% ethyl acetate in hexane and evaporation in vacuo affords a foam. The hydrochloride salt is prepared.

Anal. Calcd. for C$_{32}$H$_{36}$N$_4$O$_5$S. HCl. H$_2$O: C, 62.89; H, 6.43; N, 9.17 Found: C, 62.74; H, 6.43; N, 9.03 MS (CI) 557

EXAMPLE 105

Z-4-[[2-Butyl-5-[[2,5-dioxo-1,3-bis(2-thienylmethyl)-4-imidazolidinylidene]methyl]-1H-imidazol-1-yl]methyl]benzoic acid To a solution of 1,1-dimethylethyl Z-4-[[2-butyl-5-[(2,5-dioxo-4-imidazolidinylidene)methyl]benzoate (0.660 g, 1.55 mmol) in DMF (5 mL) and THF (5 mL) is added NaH (0.13 g, 3.25 mmol). After stirring for 5 minutes 2-thienylmethyl bromide (0.58 g, 3.28 mmol) is added. The mixture is stirred for 16 hours, filtered and evaporated in vacuo. The gum is dissolved in ethyl acetate and washed with water, brine and dried over MgSO$_4$. Chromatography eluting with (50–100)% ethyl acetate in hexane and evaporation in vacuo affords a foam. This foam is dissolved in methylene chloride (15 mL) and trifluoroacetic acid (4 mL) is added. The mixture is evaporated in vacuo and then dissolved in ethyl acetate. After washing with pH 4 buffer and drying over MgSO$_4$ the product is isolated by chromatography, eluant (2–5)% methanol in chloroform. Crystallized from THF/Ether Anal. Calcd. for C$_{29}$H$_{28}$N$_4$O$_4$S$_2$.H$_2$O: C, 62.12; H, 5.03; N, 9.99 Found: C, 62.24; H, 5.05; N, 9.90 mp 204°–205° C.; MS (CI) 561

EXAMPLE 106

Methyl Z-4-[[2-butyl-5-[[1-butyl-3-(5-isoxazolyl-methyl)-2,5-dioxo-4-imidazolidinylidene]methyl]-1H-imidazol-1-yl]methyl]benzoate monohydrochloride To a solution of methyl Z-4-[[2-Butyl-5-[[1-butyl-2,5-dioxo-4-imidazolidinylidene]methyl ]-1H- imidazol-1-yl]methyl]benzoate (0.420 g, 0.96 mmol) in DMF (20 mL) is added K$_2$CO$_3$ (0.40 g, 4.5 mmol). After stirring for 5 minutes 5-bromomethylisoxazole (0. 160 g, 1.00 mmol) is added. The mixture is stirred for 16 hours, filtered and evaporated in vacuo. The gum is dissolved in ethyl acetate and washed with water and, brine, and dried over MgSO$_4$. Chromatography eluting with (0–5) methanol in methylene chloride and evaporation in vacuo affords a foam. The hydrochloride salt was prepared. Anal. Calcd. for C$_{28}$H$_{33}$N$_5$O$_5$. HCl. 1.6H$_2$O: C, 57.50; H, 6.41; N,11.97

Found: C, 57.19; H, 6.41; N,11.70 MS (CI) 520

EXAMPLE 107

Methyl Z-4-[[2-butyl-5-[[2,5-dioxo-4,4,4,-(trifluorobutyl)-4-imidazolidinylidene]methyl]-1H-imidazol-1-yl]methyl]-benzoate To a solution of diethyl 2,5-dioxo-1-[4,4,4-(trifluorobutyl)]-4-imidazolylphosphonate (2.43 g, 7.01 mmol) in methylene chloride (15 mL) was added 1,8diazabicyclo [5.4.0] undec-7-ene (1.07 g, 7.02 mmol). The yellow solution is stirred for 10 minutes and then a solution of methyl 4-[(2-butyl-5-formyl-1H-imidazol1-yl)methyl]benzoate (2.11 g, 7.01 mmol) was added. This mixture is allowed to stir for 16 hours. The mixture is diluted with ethyl acetate and washed with water and then brine. After drying over MgSO$_4$ the product is isolated as a yellow solid by concentration in vacuo and treatment with ether. Crystallized from ethyl acetate.

Anal. Calcd. for C$_{24}$H$_{27}$N$_4$O$_4$F$_3$: C, 58.53; H, 5.53; N, 11.38 Found: C, 58.93; H, 5.51; N, 11.28 mp 188°–189° C.; MS (CI) 493

EXAMPLE 108

Methyl Z-4-[[2-butyl-5-[[1-butyl-3-[(5-methyl-3-isoxazolyl)methyl]-2,5-dioxo-4-imidazolidinylidene]methyl]-1H-imidazol-1-yl]methyl]benzoate To a solution of methyl Z-4-[[2-butyl-5-[[1-butyl-2,5-dioxo-4-imidazolidinylidene]methyl]-1H-imidazol-1-yl]methyl]benzoate (0.700 g, 1.60 mmol) in DMF (14 mL) is added K$_2$CO$_3$ (1.10 g, 7.98 mmol). After stirring for 5 minutes 3-chloromethyl-5-methylisoxazole [approx. 90% pure] (0.42 g, 1.00 mmol) is added. The mixture is stirred for 16 hours, filtered, and evaporated in vacuo. The gum is dissolved in ethyl acetate and washed with water, brine and dried over MgSO$_4$. Chromatography eluting with (2–5)% methanol in methylene chloride and evaporation in vacuo affords a solid gum.

Anal. Calcd. for $C_{29}H_{35}N_5O_5$: C, 65.27; H, 6.61; N, 13.12 Found: C, 65.31; H, 6.66; N, 12.81 MS (CI) 534

EXAMPLE 109

Methyl Z-4-[[2-butyl-5-[[1-ethyl-3-[(2-methyl-4-thiazolyl)methyl]-2,5-dioxo-4-imidazolidinylidene]methyl]-1H-imidazol-1-yl]methyl]benzoate dihydrochloride To a solution of Methyl Z-4-[[2-Butyl-5-[[1-ethyl-2,5-dioxo-4-imidazolidinylidene]methyl]-1H-imidazol-1-yl]methyl]benzoate (1.28 g, 3.23 mmol) in DMF (15 mL) is added $K_2CO_3$ (2.68 g, 19.42 retool). After stirring for 5 minutes 4-chloromethyl-2-methylthiazole hydrochloride (0.624 g, 3.39 mmol) is added. The mixture is stirred for 3 days. A further amount of 4-chloromethyl-2-methylthiazole hydrochloride (1.248 g, 6.78 mmol) was added as well as an additional amount of $K_2CO_3$ (1.34 g, 9.7 retool). The thick-mixture was stirred for 2 days. The mixture was filtered and evaporated in vacuo. The gum was dissolved in ethyl acetate and washed with water, brine and dried over $MgSO_4$. Chromatography eluting with (40–100)% ethyl acetate in hexane. The hydrochloride salt was prepared by the addition of ethereal HCl to the product in ethyl acetate. The salt was recrystallized from i-propanol/ether.

Anal. Calcd. for $C_{27}H_{31}N_5O_4S.2HCl$: C, 54.54; H, 5.59; N, 11.78 Found: C, 54.18; H, 5.54; N, 11.45 MS (CI) 522

EXAMPLE 110

Methyl Z-4-[[2-butyl-5-[[1-butyl-3-[(2-methyl-4-thiazolyl)methyl]-2,5-dioxo-4-imidazolidinylidene[methyl]-1H-imidazol-1-yl]methyl]-3chloro benzoate monohydrochloride To a solution of methyl Z-4-[[2-butyl-5-[[1-butyl-2,5-dioxo-4-imidazolidinylidene]methyl]-1H-imidazol-1-yl]methyl]-3-chloro benzoate (0.700 g, 1.48 mmol) in DMF (10 mL) is added $K_2CO_3$ (1.02 g, 7.40 mmol). After stirring for 5 minutes 4-chloromethyl-2-methylthiazole hydrochloride (0.54 g, 2.96 mmol) is added. The mixture is stirred for 16 hours. The mixture was filtered and evaporated in vacuo. The gum was dissolved in ethyl acetate and washed with water, brine and dried over $MgSO_4$. Chromatography eluting with 50% ethyl acetate in methylene chloride. The hydrochloride salt was prepared by the addition of ethereal HCl to the product in ether. The salt was recrystallized from i-propanol/ether.

Anal. Calcd. for $C_{29}H_{34}N_5O_4SCl\ .13HCl\ 1.26\ H_2O$: C, 53.95; H, 5.86; N, 10.84 Found: C, 53.75; H, 5.67; N, 10.45 MS (CI) 584

EXAMPLE 111

Methyl Z-4-[[2-Butyl-5-[[3-[(2-methyl-4-thiazoyl)methyl]-2,5-dioxo-1-(4,4,4-trifluorobutyl)-4-imidazolidinylidene]-methyl]-1H-imidazol-1-yl]methyl]benzoate dihydrochloride To a solution of methyl Z-4-[[2-butyl-5-[[2,5-dioxo-1-(4,4,4-trifluorobutyl)-4-imidazolidinylidene]methyl]-1H-imidazol-1-yl]methyl]benzoate. (1.00 g, 2.03 mmol) in DMF (15 mL) is added $K_2CO_3$ (1.92 g, 14.20 mmol). After stirring for 5 minutes 4-chloromethyl-2-methyl-thiazole hydrochloride (0.56 g, 3.05 mmol) is added. The mixture is stirred for 18 hours. The mixture was filtered and evaporated in vacuo. The gum was dissolved in ethyl acetate and washed with water and then brine. Dried over $MgSO_4$. The hydrochloride salt was prepared by the addition of ethereal HCl to the product in ether. The salt was recrystallized from i-propanol/ether.

Anal. Calcd. for $C_{29}H_{33}N_5O_5SF_3\ 2HCl\ 1.5\ H_2O$: C, 49.50; H, 5.30; N, 9.95 Found: C, 49.90; H, 5.31; N, 9.89 MS (CI) 604; mp 132°–134° C.

EXAMPLE 112

Methyl Z-4-[[2-butyl-5-[[1-butyl-2,5-dioxo-3-(4,4,4-trifluorobutyl)-4-imidazolidinylidene]methyl]-1H-imidazol-1-yl]methyl]benzoate dihydrochloride To a solution of methyl Z-4-[[2-butyl-5-[1-butyl-2,5-dioxo-4-imidazolidinylidene)methyl]-1H-imidazol-1-yl]methyl]benzoate. (0.70g, 1.59 mmol) in DMF (15 mL) is added $K_2CO_3$ (1.10g, 7.98 mmol). After stirring for 5 minutes 4,4,4-trifluoromethyl-1-iodobutane (0.38 g, 1.59 mmol) is added and the mixture stirred for 18 hours. The mixture was filtered and evaporated in vacuo. The gum was dissolved in ethyl acetate and washed with water, brine and dried over $MgSO_4$. The hydrochloride salt was prepared by the addition of ethereal HCl to the product in ether. The salt was recrystallized from i-propanol/ether.

Anal. Calcd. for $C_{28}H_{35}N_4O_4F_3.\ 1HCl$: C, 57.40; H, 6.20; N, 9.58 Found: C, 57.38; H, 6.11; N, 9.44 MS (CI) 549; mp 161°–162° C.

EXAMPLE 112

Methyl Z-4-[[2-butyl-5-[[1-butyl-2,5-dioxo-3-(4,4,4-trifluorobutyl)-4-imidazolidinylidene]methyl]-1H-imidazol-1-yl]methyl]benzoate dihydrochloride To a solution of methyl Z-4-[[2-Butyl-5-[1-(4,4,4-trifluorobutyl)-2,5-dioxo-4-imidazolimidazolidinylidene)-methyl]-1H- imidazol-1-yl]methyl]benzoate. (0.98 g, 2.80 mmol) in DMF (10 mL) is added $K_2CO_3$ (1.95 g, 14.15 mmol). After stirring for 5 minutes 4,4,4-trifluoromethyl-1-iodobutane (0.74 g, 3.10 mmol) is added and the mixture stirred for 18 hours. The mixture was filtered and evaporated in vacuo. The gum was dissolved in ethyl acetate and washed with water, brine and dried over $MgSO_4$. The hydrochloride salt was prepared by the addition of ethereal HCl to the product in ether. The salt was recrystallized from i-propanol/ether.

Anal. Calcd. for $C_{28}H_{32}N_4O_4F_6.1HCl$: C, 52.63; H, 5.21; N, 8.77 Found: C, 52.78; H, 5.18; N, 8.62 MS (CI) 603; mp 141°–142° C.

EXAMPLE 114

Z-1-Butyl-5-[[2-butyl-3-(triphenylmethyl)-3H-imidazol-5-yl]methylene]-2,4-imidazolidinedione To a solution of diethyl 1-butyl-2,5-dioxo-4-imidazolidinylphosphonate (2.94 g, 10 mmol) in methylene chloride (10 mL) was added DBU (1.5 mL, 10 mmol) and the mixture stirred for 5 minutes. 2-butyl-1-(triphenylmethyl)-1H-imidazol-4-carboxaldehyde (2.20 g, 5.58 mmol) was added and the yellow solution stirred for 16 hours. The mixture was evaporated in vacuo, redissolved in ethyl acetate, and washed with water and then brine. After drying over $MgSO_4$ the product was isolated by chromatography on silica eluting with chloroform.

MS (CI) 533

EXAMPLE 115

Z-1,3-Dibutyl-5-[[2-butyl-3-(triphenylmethyl)-3H-imidazol-5-yl]methylene]-2,4-imidazolidinedione To a solution of Z-1-butyl-5-[[2-butyl-3-(triphenylmethyl)-3H-imidazol-5-yl]methylene]-2,4 imidazolidinedione (1.20 g, 2.26 mmol) in DMF (5 mL) was added $K_2CO_3$ (1.56 g, 11.3 retool) and then 1-iodobutane (0.344 mL, 3.02 mmol). The mixture was stirred for 16 hours and then diluted with ether and washed with water and brine. After drying over $MgSO_4$ the product was isolated by chromatography on silica eluting with 80 % petroleum ether 20 % ethyl acetate. MS (CI) 588

EXAMPLE 116

Methyl Z-4-[[2-butyl-5-[(1,3-dibutyl-2,5-dioxo-4-imidazolidinylidene)methyl]-1H-imidazol-1-yl]methyl]-benzoate monohydrochloride To a solution of trifluoromethanesulfonic anhydride (0.094 mL, 0.56 mmol) in methylene chloride (10 mL) at −78° C. was added a solution of methyl 4-(hydroxymethyl)benzoate (0.093g, 0.56 mmol) and N,N-diisopropylethylamine (0.098 mL, 0.56 mmol) in methylene chloride (10 mL) dropwise over 5 minutes. This solution was stirred for 15 minutes and then a solution of Z-1,3-dibutyl-5-[[2-butyl-3-(triphenylmethyl)-3H-imidazol-5-yl]methylene]-2,4imidazolidinedione (0.330g, 0.56 mmol) in methylene chloride (5 mL) was added dropwise. The mixture was allowed to slowly warm to room temperature within the cooling bath overnight. Glacial acetic acid (10 mL) and water (2 mL) were added and the mixture boiled for 1 hour on a steam bath. After evaporation in vacuo the residue was dissolved in ethyl acetate, washed with saturated NaHCO$_3$ and brine, and then dried over MgSO$_4$. Chromatography eluting with CHCl$_3$ afforded the required product with spectral characteristics identical with the product formed in Example 33

We claim:

1. A method of treating hyperaldosteronism comprising administering to a host suffering therefrom a therapeutically effective amount of a compound of formula

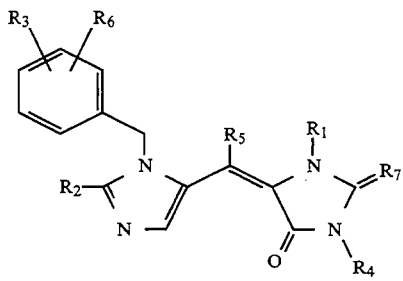

or

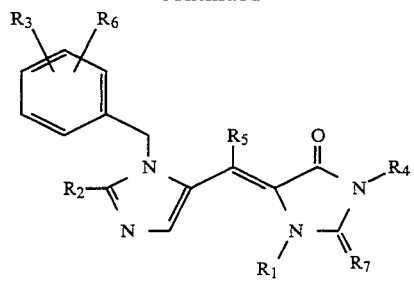

or a pharmaceutically salt thereof wherein:

$R_1$ is hydrogen, straight or branched alkyl or alkenyl from 1 to 8 carbon atoms;

alkyl as above substituted with HO, NO$_2$, CN, NH$_2$, CO$_2$CH$_3$, CO$_2$C$_2$H$_5$, or CONH$_2$;

(CH$_2$)$_n$aryl wherein n is an integer from 0 to 4 and aryl is Ph or Ph substituted with Cl, Br, I, CF, CH$_3$, OCH$_3$, OH, NO$_2$, CF$_3$, CN, CONH$_2$, CO$_2$H, NH$_2$, NHCH$_3$, or N(CH$_3$)$_2$ groups, methylenedioxy;

(CH$_2$)$_n$heteroaryl wherein n is an integer from 0 to 3 and heteroaryl is 2-thienyl, 3-thienyl, 2-furanyl, 3-furanyl, 2-pyrrolyl, 3-pyrrolyl, 2-pyridyl, 3-Pyridyl, 4-pyridyl, 2-thiazolyl, 2-oxazolyl, 2-imidazolyl, 4-thiazolyl, 4-oxazolyl, 4-imidazolyl, 5-thiazolyl, 5-oxazolyl, 5-tetrazole, 3-isoxazole, 4-isoxazole, or 5-isoxazole;

(CH$_2$)$_n$heteroaryl as above substituted with methyl, ethyl, propyl, Butyl, Cl, Br, I, F, OMe, OH, NO$_2$, NH$_2$, NHM$_e$, NMe$_2$, CO$_2$R, CO$_2$R, SO$_2$NHR, SO$_3$H, CONR$_2$, CN, CF$_3$, (CH$_2$)$_m$X(CH$_2$)$_n$H wherein X is O, S, or N and m and n are each independently integral from 1 to 6 carbon atoms;

(CH$_2$)$_n$cycloalkyl wherein n is an integer from 0 to 3 and cycloalkyl is a saturated or unsaturated ring of 3 to 7 carbon atoms;

$R_2$ is cycloalkyl of from 3 to 6 carbon atoms; alkyl of from 1 to 6 carbon atoms, alkenyl of from 2 to 6 carbon atoms, OC$_1$–C$_5$alkyl, and SC$_1$–C$_5$alkyl;

$R_3$ is (CH$_2$)$_n$CO$_2$Y or $$(CH_2)_m$$
$$-C-CO_2Y$$

wherein Y is hydrogen or lower alkyl, n is an integer of from 0 to 3, and m is an integer of from 2 to 7;

CH$_2$SO$_2$NHCOR,

NHSO$_2$NHCOR,

NHCONHSO$_2$R,

CONHSO$_2$R,

SO$_3$H,

B(OH)$_2$,

SO$_2$NHCOR,

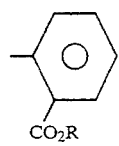

SO$_2$NHCONHR,

NHSO$_2$CF$_3$,

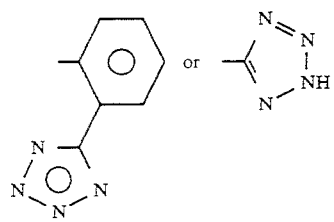

wherein R is C$_1$–C$_8$ alkyl
R$_4$ is R$_1$;
R$_5$ is hydrogen or alkyl of from 1 to 4 carbon atoms;
E$_6$ is hydrogen, chlorine, bromine, fluorine, methyl, trifluoromethyl, or methoxy; and
R$_6$ is hydrogen, chlorine, bromine, fluorine, methyl, trifluoromethyl, or methoxy; and
R$_7$ is oxygen or sulfur, in unit dosage form.

2. A method of treating congestive heart failure comprising administering to a host suffering therefrom a therapeutically effective amount of a compound of formula

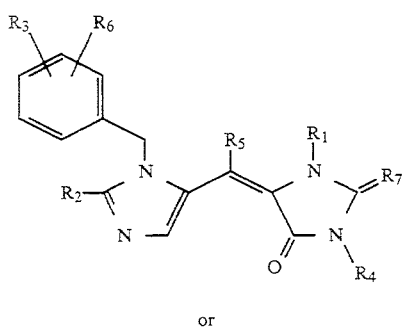

or

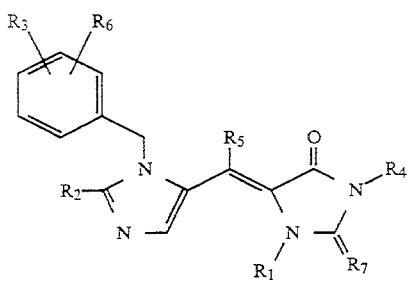

or a pharmaceutically salt thereof wherein:
R$_1$ is
  hydrogen,
  straight or branched alkyl or alkenyl from 1 to 8 carbon atoms;
  alkyl as above substituted with HO, NO$_2$, CN, NH$_2$, CO$_2$CH$_3$, CO$_2$C$_2$H$_5$, or CONH$_2$;
  (CH$_2$)$_n$aryl wherein n is an integer from 0 to 4 and aryl is Ph or Ph substituted with Cl, Br, I, F, CH$_3$, OCH$_3$, OH, NO$_2$, CF$_3$, CN, CONH$_2$, CO$_2$H, NH$_2$, NHCH$_3$, or NCH$_3$)$_2$ groups, methylenedioxy;
  (CH$_2$)$_n$heteroaryl wherein n is an integer from 0 to 3 and heteroaryl is 2-thienyl, 3-thienyl, 2-furanyl, 3-furanyl, 2-pyrrolyl, 3-pyrrolyl, 2-pyridyl, 3-pyridyl, 4-pyridyl, 2-thiazolyl, 2-oxazolyl, 2-imidazolyl, 4-thiazolyl, 4-oxazolyl, 4-imidazolyl, 5-thiazolyl, 5-oxazolyl, 5-tetrazole, 3-isoxazole, 4-isoxazole, or 5-isoxazole;
  (CH$_2$)$_n$heteroaryl as above substituted with methyl, ethyl, propyl, Butyl, Cl, Br, I, F, OMe, OH, NO$_2$, NH$_2$, NHM$_e$, NMe$_2$, CO$_2$R, CO$_2$R, SO$_2$NHR, SO$_3$H, CONR$_2$, CN, CF$_3$;
  (CH$_2$)$_m$X)CH$_2$)$_n$H wherein X is O, S, or N and m and n are each independently integral from 1 to 6 carbon atoms;
  (CH$_2$)$_n$cycloalkyl wherein n is an integer from 0 to 3 and cycloalkyl is a saturated or unsaturated ring of 3 to 7 carbon atoms;
R$_2$ is
  cycloalkyl of from 3 to 6 carbon atoms;
  alkyl of from 1 to 6 carbon atoms, alkenyl of from 2 to 6 carbon atoms, OC$_1$–C$_5$alkyl, and SC$_1$–C$_5$alkyl;
R$_3$ is
  (CH$_2$)$_n$CO$_2$Y or (CH$_2$)$_m$
  |
  —C—CO$_2$Y wherein Y is hydrogen or lower alkyl, n is an integer of from 0 to 3, and m is an integer of from 2 to 7;
  CH$_2$SO$_2$NHCOR,
  NHSO$_2$SO$_2$NHCOR,
  NHSO$_2$NHCOR,
  NHCONHSO$_2$R,
  PO(OR)$_2$,
  CONHSO$_2$R,
  SO$_3$H,
  B(OH)$_2$,
  SO$_2$NHCOR,

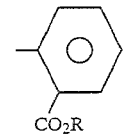

SO$_2$NHCONHR,

NHSO$_2$CF$_3$,

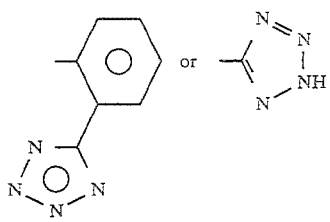

wherein R is C$_1$–C$_8$ alkyl;
R$_4$ is R$_1$;
R$_5$ is hydrogen or alkyl from 1 to 4 carbon atoms;

R₆ is hydrogen, chlorine, bromine, fluorine, methyl, trifluoromethyl, or methoxy; and R₇ is oxygen or sulfur, in unit dosage form.

3. A method of treating or preventing vascular occlusion due to smooth muscle proliferation following vascular surgeries comprising administering to a host in need thereof a therapeutically effective amount of a compound of formula

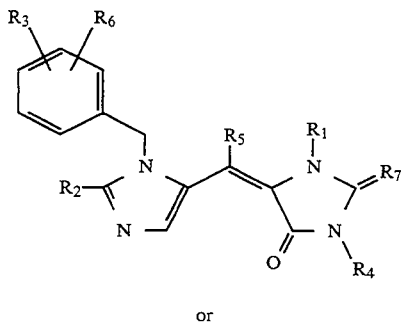

or

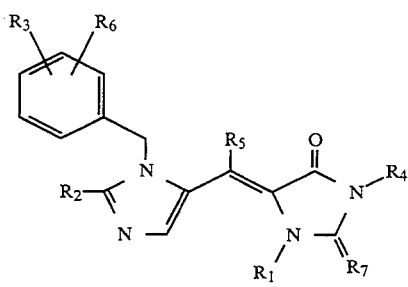

or a pharmaceutically salt thereof wherein:
R₁ is
hydrogen,
straight or branched alkyl or alkenyl from 1 to 8 carbon atoms;
alkyl as above substituted with HO, NO₂, CN, NH₂, CO₂CH₃; CO₂C₂H₅; or CONH₂;
(CH₂)ₙ aryl wherein n is an integer from 0 to 4 and aryl is Ph or Ph substituted with Cl, Br, I, F, CH₃, OCH₃, OH, NO₂, CF₃, CN, CONH₂, CO₂H, NH₂, NHCH₃, or NCH₃)₂ groups, methylenedioxy;.
(CH₂)ₙheteroaryl wherein n is an integer from 0 to 3 and heteroaryl is 2-thienyl, 3-thienyl, 2-furanyl, 3-furanyl, 2-pyrrolyl, 3-pyrrolyl, 2-pyridyl, 3-pyridyl, 4-pyridyl, 2-thiazolyl, 2-oxazolyl, 2-imidazolyl, 4-thiazolyl, 4-oxazolyl, 4-imidazolyl, 5-thiazolyl, 5-oxazolyl, 5-tetrazole, 3-isoxazole, 4-isoxazole, or 5-isoxazole;
(CH₂)ₙheteroaryl as above substituted with methyl, ethyl, propyl, Butyl, Cl, Br, I, F, OMe, OH, NO₂, NH₂, NHMₑ, NMe₂, CO₂R, CO₂R, SO₂NHR, SO₃H, CONR₂, CN, CF₃;
(CH₂)ₘX)CH₂)ₙH wherein X is O, S, or N and m and n are each independently integral from 1 to 6 carbon atoms;
(CH₂)ₙcycloalkyl wherein n is an integer from 0 to 3 and cycloalkyl is a saturated or unsaturated ring of 3 to 7 carbon atoms;
R₂ is
cycloalkyl of from 3 to 6 carbon atoms;
alkyl of from 1 to 6 carbon atoms,
alkenyl of from 2 to 6 carbon atoms, OC₁-C₅alkyl, and SC₁-C₅alkyl R₃ is
(CH₂)ₙCO₂Y or

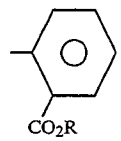

—C—CO₂Y wherein Y is hydrogen or lower alkyl, n is an integer of from 0 to 3, and m is an integer of from 2 to 7;
CH₂SO_NHCOR,
NHSO₂NHCOR,
NHCONHSO₂R,
PO(OR)₂,
CONHSO₂R,
SO₃H,
B(OH)₂,
SO₂NHCOR,

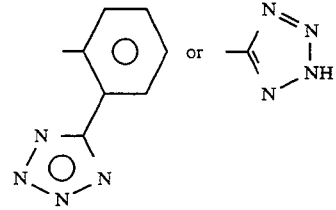

SO₂NHCONHR,

NHSO₂CF₃,

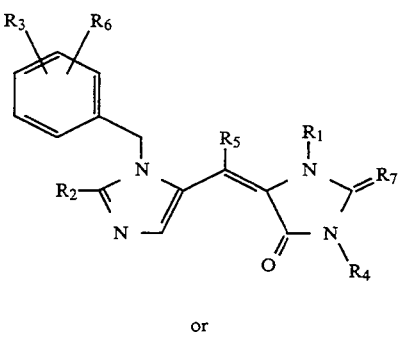

wherein R is C₁-C₈ alkyl;
R₄ is R₁;
R₅ is hydrogen or alkyl of from 1 to 4 carbon atoms;
R₅ is hydrogen, chlorine, bromine, fluorine, methyl, trifluoromethyl, or methoxy; and
R₇ is oxygen or sulfur, in unit dosage form.

4. A method of treating glaucoma comprising administering to a host suffering therefrom a therapeutically effective amount of a compound of formula

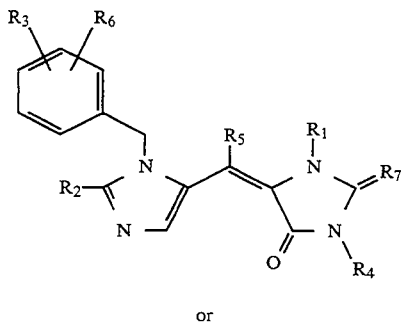

or

-continued

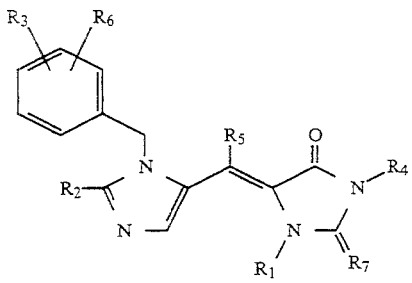

or a pharmaceutically salt thereof wherein:
$R_1$ is
  hydrogen,
  straight or branched alkyl or alkenyl from 1 to 8 carbon atoms;
  alkyl as above substituted with HO, $NO_2$, CN, $NH_2$, $CO_2CH_3$, $CO_2C_2H_5$, or $CONH_2$;
  $(CH_2)_n$aryl wherein n is an integer from 0 to 4 and aryl is Ph or Ph substituted with Cl, Br, I, F, $CH_3$, $OCH_3$, OH, $NO_2$, $CF_3$, CN, $CONH_2$, $CO_2H$, $NH_2$, $NHCH_3$, or $N(CH_3)_2$ groups, methylenedioxy;
  $(CH_2)_n$heteroaryl wherein n is an integer from 0 to 3 and heteroaryl is 2-thienyl, 3-thienyl, 2-furanyl, 3-furanyl, 2-pyrrolyl, 3-pyrrolyl, 2-pyridyl, 3-pyridyl, 4-pyridyl, 2-thiazolyl, 2-oxazolyl, 2-imidazolyl, 4-thiazolyl, 4-oxazolyl, 4-imidazolyl, 5-thiazolyl, 5-oxazolyl, 5-tetrazole, 3-isoxazole, 4-isoxazole, or 5-isoxazole;
  $(CH_2)_n$heteroaryl as above substituted with methyl, ethyl, propyl, Butyl, Cl, Br, I, F, OMe, OH, $NO_2$, $NH_2$, $NHM_e$, $NMe_2$, $CO_2R$, $CO_2H$, $SO_2NHR$, $SO_3H$, $CONR_2$, CN, $CF_3$,
  $(CH_2)_mX)CH_2)_n{}^H$ wherein X is O, S, or N and m and n are each independently integral from 1 to 6 carbon atoms;
  $(CH_2)_n$cycloalkyl wherein n is an integer from 0 to 3 and cycloalkyl is a saturated or unsaturated ring of 3 to 7 carbon atoms;
$R_2$ is
  cycloalkyl of from 3 to 6 carbon atoms;
  alkyl of from 1 to 6 carbon atoms,
  alkenyl of from 2 to 6 carbon atoms, $OC_1–C_5$alkyl, and $SC_1–C_5$alkyl;
$R_3$ is
  $(CH_2)_nCO_2Y$ or

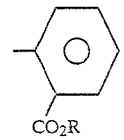

wherein Y is hydrogen or lower alkyl, n is an integer of from 0 to 3, and m is an integer of from 2 to 7;
  $CH_2SO_2NHCOR$,
  $NHSO_2NHCOR$,
  $NHCONHSO_2R$,
  $PO(OR)_2$,
  $CONHSO_2R$,
  $SO_3H$,
  $B(OH)_2$,
  $SO_2NHCOR$,

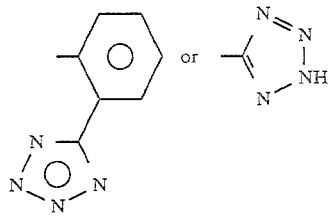

$SO_2NHCONHR$, $NHSO_2CF_3$,

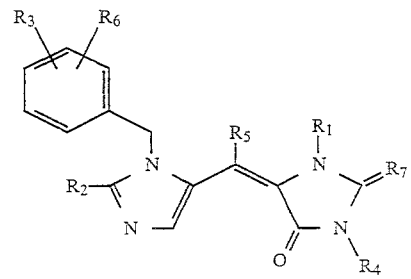

wherein R is $C_1$–$C_8$ alkyl;
$R_4$ is $R_1$;
$R_5$ is hydrogen or alkyl of from 1 to 4 carbon atoms;
$R_6$ is hydrogen, chlorine, bromine, fluorine, methyl, trifluoromethyl, or methoxy; and
$R_7$ is oxygen or sulfur, in unit dosage form.

5. A method of treating hemorrhagic stroke comprising administering to a host suffering therefrom a therapeutically effective amount of a compound of formula

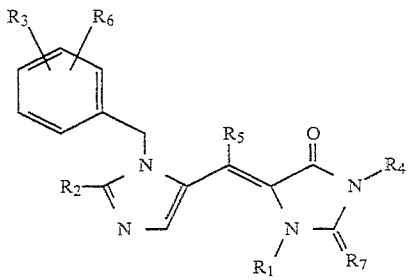

of a pharmaceutically salt thereof wherein:
$R_1$ is
hydrogen,
straight or branched alkyl or alkenyl from 1 to 8 carbon atoms; alkyl as above substituted with HO, $NO_2$, CN, $NH_2$, $CO_2CH_3$, $CO_2C_2H_5$, or $CONH_2$;
  $(CH_2)_n$aryl wherein n is an integer from 0 to 4 and aryl is Ph or Ph substituted with Cl, Br, I, F, $CH_3$, $OCH_3$, OH, $NO_2$, $CF_3$, CN, $CONH_2$, $CO_2H$, $NH_2$, $NHCH_3$, or $N(CH_3)_2$ groups, methylenedioxy;
  $(CH_2)_n$heteroaryl wherein n is an integer from 0 to 3 and heteroaryl is 2-thienyl, 3-thienyl, 2-furanyl, 3-furanyl, 2-pyrrolyl, 3-pyrrolyl, 2-pyridyl, 3-pyridyl, 4-pyridyl, 2-thiazolyl, 2-oxazolyl, 2-imidazolyl, 4-thiazolyl, 4-oxazolyl, 4-imidazolyl, 5-thiazolyl, 5-oxazolyl, 5-tetrazole, 3-isoxazole, 4-isoxazole, or 5-isoxazole;

$(CH_2)_n$heteroaryl as above substituted with methyl, ethyl, propyl, Butyl, Cl, Br, I, F, OMe, OH, $NO_2$, $NH_2$, $NHM_e$, $NMe_2$, $CO_2R$, $CO_2H$, $SO_2NHR$, $SO_3H$, $CONR_2$, CN, $CF_3$;

$(CH_2)_mX(CH_2)_nH$ wherein X is O, S, or N and m and n are each independently integral from 1 to 6 carbon atoms;

$(CH_2)_n$cycloalkyl wherein n is an integer from 0 to 3 and cycloalkyl is a saturated or unsaturated ring of 3 to 7 carbon atoms;

$R_2$ is
cycloalkyl of from 3 to 6 carbon atoms; alkyl of from 1 to 6 carbon atoms, alkenyl of from 2 to 6 carbon atoms, $OC_1-C_5$alkyl, and $SC_1-C_5$alkyl;

$R_3$ is
$(CH_2)_nCO_2Y$ or

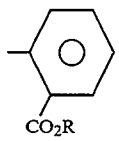

wherein Y is hydrogen or lower alkyl, n is an integer of from 0 to 3, and m is an integer of from 2 to 7;

$CH_2SO_2NHCOR$,
$NHSO_2NHCOR$,
$NHCONHSO_2R$,
$PO(OR)_2$,
$CONHSO_2R$,
$SO_3H$,
$B(OH)_2$,
$SO_2NHCOR$,

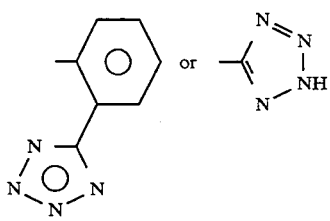

$SO_2NHCONHR$, $NHSO_2CF_3$, wherein R is $C_1-C_8$ alkyl;
$R_4$ is $R_1$;
$R_5$ is hydrogen or alkyl of from 1 to 4 carbon atoms;
$R_6$ is hydrogen, chlorine, bromine, fluorine, methyl, trifluoromethyl, or methoxy; and
$R_7$ is oxygen or sulfur, in unit dosage form.

6. A method of treating angina pectoris comprising administering to a host suffering therefrom a therapeutically effective amount of a compound of formula

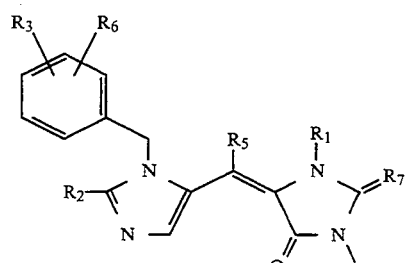

or

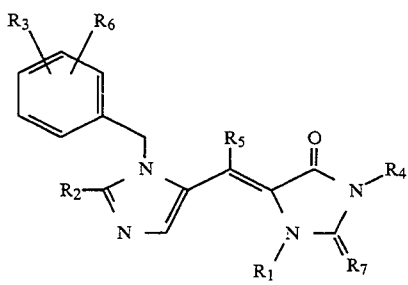

or a pharmaceutically salt thereof wherein:
$R_1$ is
hydrogen,
straight or branched alkyl or alkenyl from 1 to 8 carbon atoms;
alkyl as above substituted with HO, $NO_2$, CN, $NH_2$, $CO_2CH_3$, $CO_2C_2H_5$, or $CONH_2$;

$(CH_2)_n$aryl wherein n is an integer from 0 to 4 and aryl is Ph or Ph substituted with Cl, Br, I, F, $CH_3$, $OCH_3$, OH, $NO_2$, $CF_3$, CN, $CONH_2$, $CO_2H$, $NH_2$, $NHCH_3$, or $N(CH_3)_2$ groups, methylenedioxy;

$(CH_2)_n$heteroaryl wherein n is an integer from 0 to 3 and heteroaryl is 2-thienyl, 3-thienyl, 2-furanyl, 3-furanyl, 2-pyrrolyl, 3-pyrrolyl, 2-pyridyl, 3-pyridyl, 4-pyridyl, 2-thiazolyl, 2-oxazolyl, 2-imidazolyl, 4-thiazolyl, 4-oxazolyl, 4-imidazolyl, 5-thiazolyl, 5-oxazolyl, 5-tetrazole, 3-isoxazole, 4-isoxazole, or 5-isoxazole;

$(CH_2)_n$heteroaryl as above substituted with methyl, ethyl, propyl, Butyl, Cl, Br, I, F, OMe, OH, $NO_2$, $NH_2$, $NHM_e$, $NMe_2$, $CO_2R$, $CO_2R$, $SO_2NHR$, $SO_3H$, $CONR_2$, CN, $CF_3$;

$(CH_2)_mX)CH_2)_nH$ wherein X is O, S, or N and m and n are each independently integral from 1 to 6 carbon atoms;

$(CH_2)_n$cycloalkyl wherein n is an integer from 0 to 3 and cycloalkyl is a saturated or unsaturated ring of 3 to 7 carbon atoms;

$R_2$ is cycloalkyl of from 3 to 6 carbon atoms; alkyl of from 1 to 6 carbon atoms, alkenyl of from 2 to 6 carbon atoms, $OC_1-C_5$alkyl,and $SC_1-C_5$alkyl;

$R_3$ is
$(CH_2)_nCO_2Y$ or $(CH_2)_m$ $-C-CO_2Y$ wherein Y is hydrogen or lower alkyl, n is an integer of from 0 to 3, and m is an integer of from 2 to 7;

CH₂SO₂NHCOR,
NHSO₂NHCOR,
NHCONHSO₂R,
PO(OR)₂,
CONHSO₂R,
SO₃H,
B(OH)₂m
SO₂NHCOR,

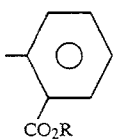

SO₂NHCONHR,

NHSO₂CF₃,

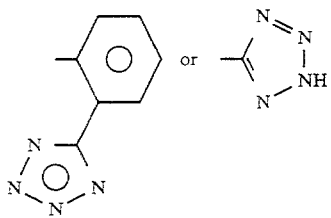 or wherein R is C₁–C₈ alkyl;

R₄ is R₁;

R₅ is hydrogen or alkyl of from 1 to 4 carbon atoms;

R₆ is hydrogen, chlorine, bromine, fluorine, methyl, trifluoromethyl, or methoxy; and R₇ is oxygen or sulfur, in unit dosage form.

7. A method of preventing restenosis after angioplasty or bypass surgery comprising administering to a host suffering therefrom a therapeutically effective amount of a compound of formula

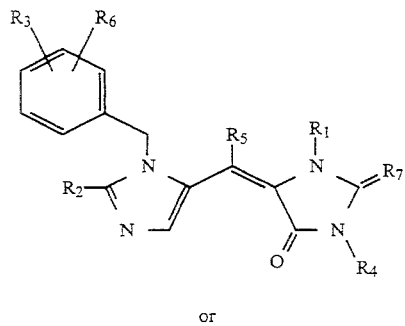

or

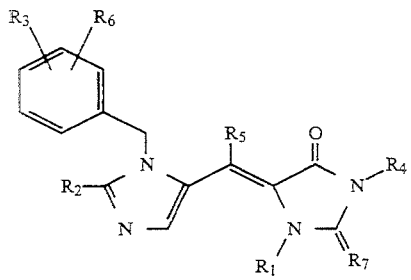

or a pharmaceutically salt thereof wherein:
R₁ is
hydrogen,
straight or branched alkyl or alkenyl from 1 to 8 carbon atoms;
alkyl as above substituted with HO, NO₂, CN, NH₂, CO₂CH₃, CO₂C₂H₅, or CONH₂;
(CH₂)ₙaryl wherein n is an integer from 0 to 4 and aryl is Ph or Ph substituted with Cl, Br, I, F, CH₃, OCH₃, OH, NO₂, CF₃, CN, CONH₂, CO₂H, NH₂, NHCH₃, or NCH₃)₂ groups, methylenedioxy;
(CH₂)ₙheteroaryl wherein n is an integer from 0 to 3 and heteroaryl is 2-thienyl, 3-thienyl, 2-furanyl, 3-furanyl, 2-pyrrolyl, 3-pyrrolyl, 2-pyridyl, 3-pyridyl, 4-pyridyl, 2-thiazolyl, 2-oxazolyl, 2-imidazolyl, 4-thiazolyl, 4-oxazolyl, 4-imidazolyl, 5-thiazolyl, 5-oxazolyl, 5-tetrazole, 3-isoxazole, 4-isoxazole, or 5-isoxazole;
(CH₂)ₙheteroaryl as above substituted with methyl, ethyl, propyl, Butyl, Ci, Br, I, F, OMe, OH, NO₂, NH₂, NHMₑ, NMe₂,CO₂R, CO₂R, SO₂NHR, SO₃H, CONR₂, CN, CF₃;
(CH₂)ₘX)CH₂)ₙH wherein X is O, S, or N and m and n are each independently integral from 1 to 6 carbon atoms;
(CH₂)ₙcycloalkyl wherein n is an integer from 0 to 3 and cycloalkyl is a saturated or unsaturated ring of 3 to 7 carbon atoms;

R₂ is
cycloalkyl of from 3 to 6 carbon atoms; alkyl of from 1 to 6 carbon atoms, alkenyl of from 2 to 6 carbon atoms, OC₁–C₅alkyl, and SC₁–C₅alkyl;

R₃ is
(CH₂)ₙCO₂Y or $$(CH_2)_m$$
$$-C-CO_2Y$$

wherein Y is hydrogen or lower alkyl, n is an integer of from 0 to 3, and m is an integer of from 2 to 7;
CH₂SO₂NHCOR,
NHSO₂NHCOR,
NHCONHSO₂R,
PO(OR)₂,
CONHSO₂R,
SO₃H,
B(OH)₂,
SO₂NHCOR,

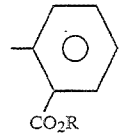

SO₂NHCONHR,

NHSO₂CF₃,

 or 

wherein R is $C_1$-$C_8$ alkyl;
$R_4$ is $R_1$;
$R_5$ is hydrogen or alkyl of from 1 to 4 carbon atoms;
$R_6$ is hydrogen, chlorine, bromine, fluorine, methyl, trifluoromethyl, or methoxy; and
$R_7$ is oxygen or sulfur, in unit dosage form.

8. A method of inhibiting progression or inducing regression of atheroma comprising administering to a host suffering therefrom a therapeutically effective amount of a compound of formula

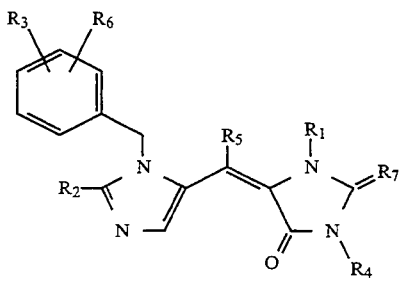

or

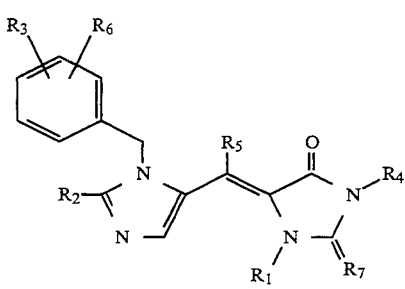

or a pharmaceutically salt thereof wherein:
$R_1$ is
  hydrogen,
  straight or branched alkyl or alkenyl from 1 to 8 carbon atoms;
  alkyl as above substituted with HO, $NO_2$, CN, $NH_2$, $CO_2CH_3$, $CO_2C_2H_5$, or $CONH_2$;
  $(CH_2)_n$aryl wherein n is an integer from 0 to 4 and aryl is Ph or Ph substituted with Cl, Br, I, F, $CH_3$, $OCH_3$, OH, $NO_2$, $CF_3$, CN, $CONH_2$, $CO_2H$, $NH_2$, $NHCH_3$, or $N(CH_3)_2$ groups, methylenedioxy;
  $(CH_2)_n$heteroaryl wherein n is an integer from 0 to 3 and heteroaryl is 2-thienyl, 3-thienyl, 2-furanyl, 3-furanyl, 2-pyrrolyl, 3-pyrrolyl, 2-pyridyl, 3-pyridyl, 4-pyridyl, 2-thiazolyl, 2-oxazolyl, 2-imidazolyl, 4-thiazolyl, 4-oxazolyl, 4-imidazolyl, 5-thiazolyl, 5-oxazolyl, 5-tetrazole, 3-isoxazole, 4-isoxazole, or 5-isoxazole;
  $(CH_2)_n$heteroaryl as above substituted with methyl, ethyl, propyl, Butyl, Cl, Br, I, F, OMe, OH, $NO_2$, $NH_2$, $NHM_e$, $NMe_2$, $CO_2R$, $CO_2R$, $SO_2NHR$, $SO_3H$, $CONR_2$, CN, $CF_3$;
  $(CH_2)_mX)(CH_2)_n{}^H$ wherein X is O, S, or N and m and n are each independently integral from 1 to 6 carbon atoms;
  $(CH_2)_n$cycloalkyl wherein n is an integer from 0 to 3 and cycloalkyl is a saturated or unsaturated ring of 3 to 7 carbon atoms;
$R_2$ is
  cycloalkyl of from 3 to 6 carbon atoms;
  alkyl of from 1 to 6 carbon atom, alkenyl of from 2 to 6 carbon atoms, $OC_1$-$C_5$alkyl, and $SC_1$-$C_5$alkyl;
$R_3$ is
  $(CH_2)_nCO_2Y$ or

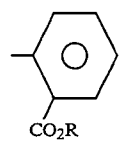

$-C-CO_2Y$ wherein Y is hydrogen or lower alkyl, n is an integer of from 0 to 3, and m is an integer of from 2 to 7;
  $CH_2SO_2NHCOR$,
  $NHSO_2NHCOR$,
  $NHCONHSO_2R$,
  $PO(OR)_2$,
  $CONHSO_2R$,
  $SO_3H$,
  $B(OH)_2$,
  $SO_2NHCOR$,

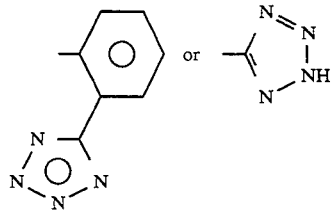

$SO_2NHCONHR$,
  $NHSO_2CF_3$,

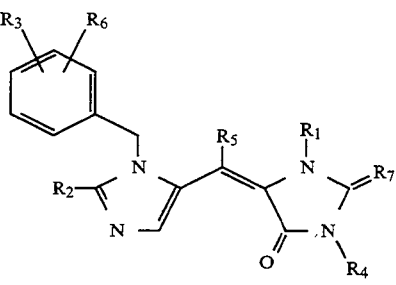

wherein R is $C_1$-$C_8$ alkyl;
$R_4$ is $R_1$;
$R_5$ is hydrogen or alkyl of from 1 to 4 carbon atoms;
$R_6$ is hydrogen, chlorine, bromine, fluorine, methyl, trifluoromethyl, or methoxy; and
$R_7$ is oxygen or sulfur, in unit dosage form.

9. A method of treating diabetic retinopathy in mammals comprising administering to a host suffering therefrom a therapeutically effective amount of a compound of formula

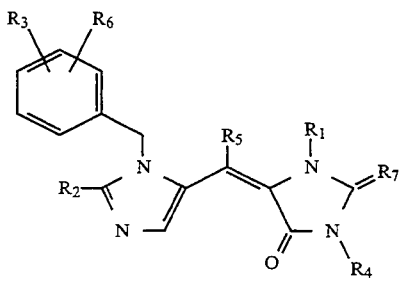

or

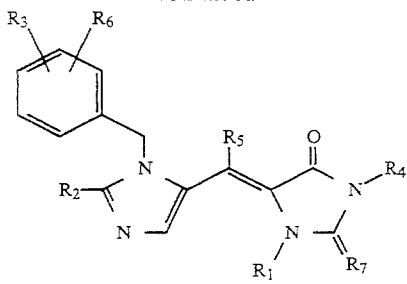

or a pharmaceutically salt thereof wherein:
$R_1$ is
  hydrogen,
    straight or branched alkyl or alkenyl from 1 to 8 carbon atoms;
    alkyl as above substituted with HO, $NO_2$, CN, $NH_2$, $CO_2CH_3$, $CO_2C_2H_5$, or $CONH_2$;
  $(CH_2)_n$aryl wherein n is an integer from 0 to 4 and aryl is Ph or Ph substituted with Cl, Br, I, F, $CH_3$, $OCH_3$, OH, $NO_2$, $CF_3$, CN, $CONH_2$, $CO_2H$, $NH_2$, $NHCH_3$, or $N(CH_3)_2$ groups, methylenedioxy;
  $(CH_2)_n$heteroaryl wherein n is an integer from 0 to 3 and heteroaryl is 2-thienyl, 3-thienyl, 2-furanyl, 3-furanyl, 2-pyrrolyl, 3-pyrrolyl, 2-pyridyl, 3-pyridyl, 4-pyridyl, 2-thiazolyl, 2-oxazolyl, 2-imidazolyl, 4-thiazolyl, 4-oxazolyl, 4-imidazolyl, 5-thiazolyl, 5-oxazolyl, 5-tetrazole, 3-isoxazole, 4-isoxazole, or 5-isoxazole;
  $(CH_2)_n$heteroaryl as above substituted with methyl, ethyl, propyl, Buty, Cl, Br, I, F, OMe, OH, $NO_2$, $NH_2$, $NHM_e$, $NMe_2$, $CO_2R$, $CO_2H$, $SO_2NHR$, $SO_3H$, $CONR_2$, CN, $CF_3$;
  $(CH_2)_mX)CH_2)n^H$ wherein X is O, S, or N and m and n are each independently integral from 1 to 6 carbon atoms;
  $(CH_2)_n$cycloalkyl wherein n is an integer from 0 to 3 and cycloalkyl is a saturated or unsaturated ring of 3 to 7 carbon atoms;
$R_2$ is
  cycloalkyl of from 3 to 6 carbon atoms;
  alkyl of from 1 to 6 carbon atoms, alkenyl of from 2 to 6 carbon atoms, $OC_1-C_5$alkyl, and $SC_1-C_5$alkyl;
$R_3$ is
  $(CH_2)_nCO_2Y$ or $$-\underset{(CH_2)_m}{\overset{}{C}}-CO_2Y$$

wherein Y is hydrogen or lower alkyl, n is an integer of from 0 to 3, and m is an integer of from 2 to 7;
  $CH_2SO_2NHCOR$,
  $NHSO_2NHCOR$,
  $NHCONHSO_2R$,
  $PO(OR)_2$,
  $CONHSO_2R$,
  $SO_3H$,
  $B(OH)_2$,
  $SO_2NHCOR$,

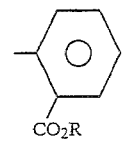

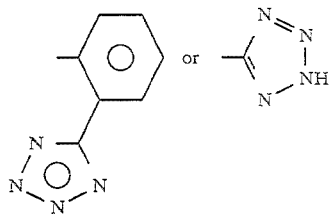

wherein R is $C_1-C_8$ alkyl;
$R_4$ is $R_1$;
$R_5$ is hydrogen or alkyl of from 1 to 4 carbon atoms;
$R_6$ is hydrogen, chlorine, bromine, fluorine, methyl, trifluoromethyl, or methoxy; and
$R_7$ is oxygen or sulfur, in unit dosage form.

10. A method of treating diabetic nephropathy comprising administering to a host suffering therefrom a therapeutically effective amount of a compound of formula

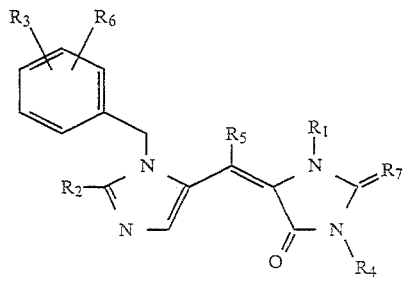

or

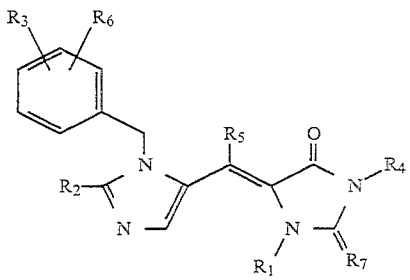

or a pharmaceutically salt thereof wherein:
$R_1$ is
  hydrogen,
    straight or branched alkyl or alkenyl from 1 to 8 carbon atoms;
    alkyl as above substituted with HO, $NO_2$, CN, $NH_2$, $CO_2CH_3$, $CO_2C_2H_5$, or $CONH_2$;
  $(CH_2)_n$aryl wherein n is an integer from 0 to 4 and aryl is Ph or Ph substituted with Cl, Br, I, F, $CH_3$, $OCH_3$, OH, $NO_2$, $CF_3$, CN, $CONH_2$, $CO_2H$, $NH_2$, $NHCH_3$, or $NCH_3)_2$ groups, methylenedioxy;

(CH₂)ₙheteroaryl wherein n is an integer from 0 to 3 and heteroaryl is 2-thienyl, 3-thienyl, 2-furanyl, 3-furanyl, 2-pyrrolyl, 3-pyrrolyl, 2-pyridyl, 3-pyridyl, 4-pyridyl, 2-thiazolyl, 2-oxazolyl, 2-imidazolyl, 4-thiazolyl, 4-oxazolyl, 4-imidazolyl, 5-thiazolyl, 5-oxazolyl, 5-tetrazole, 3-isoxazole, 4-isoxazole, or 5-isoxazole;

(CH₂)ₙheteroaryl as above substituted with methyl, ethyl, propyl, Butyl, Cl, Br, I, F, OMe, OH, NO₂, NH₂, NHMe, NMe₂, CO₂R, CO₂R, SO₂NHR, SO₃H, CONR₂, CN, CF₃;

(CH₂)ₘX)CH₂)ₙH wherein X is O, S, or N and m and n are each independently integral from 1 to 6 carbon atoms;

(CH₂)ₙcycloalkyl wherein n is an integer from 0 to 3 and cycloalkyl is a saturated or unsaturated ring of 3 to 7 carbon atoms;

R₂ is
cycloalkyl of from 3 to 6 carbon atoms;
alkyl of from 1 to 6 carbon atoms, alkenyl of from 2 to 6 carbon atoms, OC₁–C₅alkyl, and SC₁–C₅alkyl;

R₃ is
(CH₂)ₙCO₂Y or

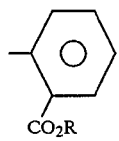

$$-\overset{(CH_2)_m}{\underset{}{C}}-CO_2Y$$

wherein Y is hydrogen or lower alkyl, n is an integer of from 0 to 3, and m is an integer of from 2 to 7;

CH₂SO₂NHCOR,
NHSO₂NHCOR,
NHCONHSO₂R,
PO(OR)₂,
CONHSO₂R,
SO₃H,
B(OH)₂,
SO₂NHCOR,

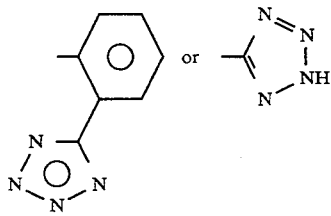

SO₂NHCONHR,

NHSO₂CF₃,

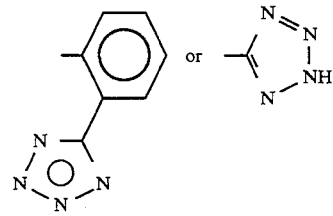

wherein R is C₁–C₈ alkyl;
R₄ is R₁;
R₅ is hydrogen or alkyl of from 1 to 4 carbon atoms;
R₆ is hydrogen, chlorine, bromine, fluorine, methyl, trifluoromethyl, or methoxy; and
R₇ is oxygen or sulfur, in unit dosage form.

11. A method of treating left ventricular hypertrophy regression comprising administering to a host suffering therefrom a therapeutically effective amount of a compound of formula

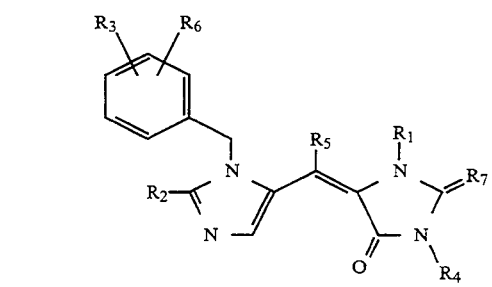

or

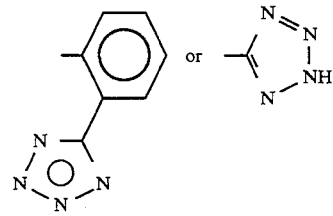

or a pharmaceutically salt thereof wherein:

R₁ is
hydrogen,
straight or branched alkyl or alkenyl from 1 to 8 carbon atoms;
alkyl as above substituted with HO, NO₂, CN, NH₂, CO₂CH₃, CO₂C₂H₅, or CONH₂;

(CH₂)ₙaryl wherein n is an integer from 0 to 4 and aryl is Ph or Ph substituted with Cl, Br, I, F, CH₃, OCH₃, OH, NO₂, CF₃, CN, CONH₂, CO₂H, NH₂, NHCH₃, or N (CH₃)₂ groups, methylenedioxy;

(CH₂)ₙheteroaryl wherein n is an integer from 0 to 3 and heteroaryl is 2-thienyl, 3-thienyl, 2-furanyl, 3-furanyl, 2-pyrrolyl, 3-pyrrolyl, 2-pyridyl, 3-pyridyl, 4-pyridyl, 2-thiazolyl, 2-oxazolyl, 2-imidazolyl, 4-thiazolyl, 4-oxazolyl, 4-imidazolyl, 5-thiazolyl, 5-oxazolyl, 5-tetrazole, 3-isoxazole, 4-isoxazole, or 5-isoxazole;

(CH₂)ₙheteroaryl as above substituted with methyl, ethyl, propyl, Butyl, Cl, Br, I, F, OMe, OH, NO₂, NH₂, NHMe, NMe₂, CO₂R, CO₂R, SO₂NHR, SO₃H, CONR₂, CN, CF₃;

(CH₂)ₘX(CH₂)ₙH wherein X is O, S, or N and m and n are each independently integral from 1 to 6 carbon atoms;

(CH₂)ₙcycloalkyl wherein n is an integer from 0 to 3 and cycloalkyl is a saturated or unsaturated ring of 3 to 7 carbon atoms;

R₂ is
cycloalkyl of from 3 to 6 carbon atoms;
alkyl of from 1 to 6 carbon atoms, alkenyl of from 2 to 6 carbon atoms, OC₁–C₅alkyl, and SC₁–C₅alkyl;

R₃ is
(CH₂)ₙCO₂Y or $$-\overset{(CH_2)_m}{\underset{}{C}}-CO_2Y$$

wherein Y is hydrogen or lower alkyl, n is an integer of from 0 to 3, and m is an integer of from 2 to 7;
CH$_2$SO$_2$NHCOR,
NHSO$_2$NHCOR,
NHCONHSO$_2$R,
PO(OR)$_2$,
CONHSO$_2$R,
SO$_3$H,
B(OH)$_2$,
SO$_2$NHCOR,

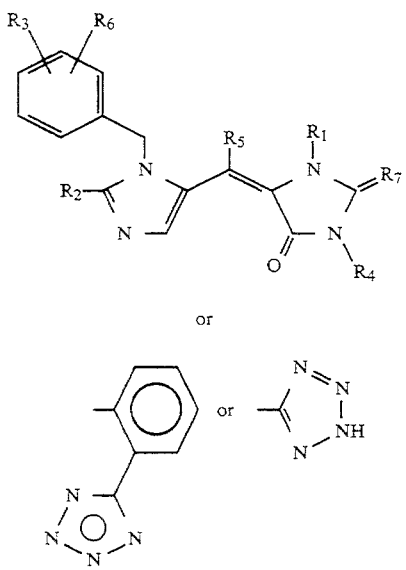

or wherein R is C$_1$–C$_8$ alkyl;
R$_4$ is R$_1$;
R$_5$ is hydrogen or alkyl of from 1 to 4 carbon atoms;
R$_6$ is hydrogen, chlorine, bromine, fluorine, methyl, trifluoromethyl, or methoxy; and
R$_7$ is oxygen or sulfur, in unit dosage form.

12. A method of prevention of infarction comprising administering to a host suffering therefrom a therapeutically effective amount of a compound of formula

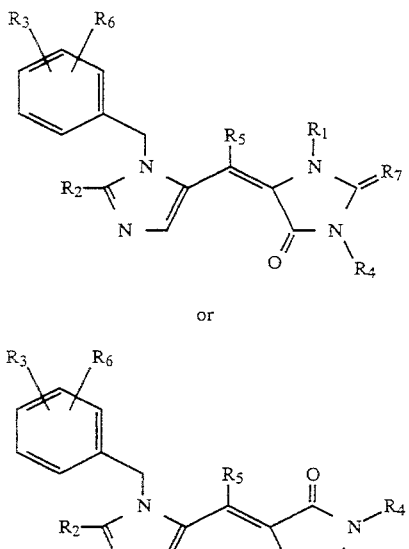

or a pharmaceutically salt thereof wherein:
R$_1$ is
hydrogen,
straight or branched alkyl or alkenyl from 1 to 8 carbon atoms;
alkyl as above substituted with HO, NO$_2$, CN, NH$_2$, CO$_2$CH$_3$, CO$_2$C$_2$H$_5$, or CONH$_2$;
(CH$_2$)$_n$aryl wherein n is an integer from 0 to 4 and aryl is Ph or Ph substituted with Cl, Br, I, F, CH$_3$, OCH$_3$, OH, NO$_2$, CF$_3$, CN, CONH$_2$, CO$_2$H, NH$_2$, NHCH$_3$, or NCH$_3$)$_2$ groups, methylenedioxy;
(CH$_2$)$_n$heteroaryl wherein n is an integer from 0 to 3 and heteroaryl is 2-thienyl, 3-thienyl, 2-furanyl, 3-furanyl, 2-pyrrolyl, 3-pyrrolyl, 2-pyridyl, 3-pyridyl, 4-pyridyl, 2-thiazolyl, 2-oxazolyl, 2-imidazolyl, 4-thiazolyl, 4-oxazolyl, 4-imidazolyl, 5-thiazolyl, 5-oxazolyl, 5-tetrazole, 3-isoxazole, 4-isoxazole, or 5-isoxazole;
(CH$_2$)$_n$heteroaryl as above substituted with methyl, ethyl, propyl, Butyl, Cl, Br, I, F, OMe, OH, NO$_2$, NH$_2$, NHM$_e$, NMe$_2$, CO$_2$R, CO$_2$H, SO$_2$NHR, SO$_3$H, CONR$_2$, CN, CF$_3$;
(CH$_2$)$_m$X)CH$_2$)$_n$H wherein X is O, S, or N and m and n are each independently integral from 1 to 6 carbon atoms;
(CH$_2$)$_n$cycloalkyl wherein n is an integer from 0 to 3 and cycloalkyl is a saturated or unsaturated ring of 3 to 7 carbon atoms;
R$_2$ is
cycloalkyl of from 3 to 6 carbon atoms;
alkyl of from 1 to 6 carbon atoms, alkenyl of from 2 to 6 carbon atoms, OC$_1$–C$_5$alkyl, and SC$_1$–C$_5$alkyl;
R$_3$ is
(CH$_2$)$_n$CO$_2$Y or (CH$_2$)$_m$

—C—CO$_2$Y wherein Y is hydrogen or lower alkyl, n is an integer of from 0 to 3, and m is an integer of from 2 to 7;
CH$_2$SO$_2$NHCOR,
NHSO$_2$NHCOR,
NHCONHSO$_2$R,
PO(OR)$_2$,
CONHSO$_2$R,
SO$_3$H,
B(OH)$_2$,
SO$_2$NHCOR,

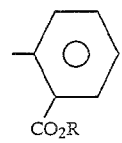

SO$_2$NHCONHR,

NHSO$_2$CF$_3$,

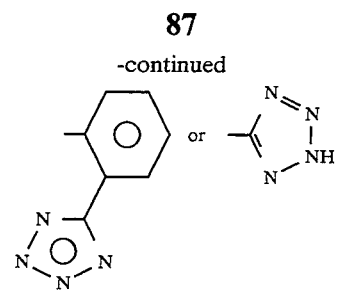
wherein R is $C_1$-$C_8$ alkyl;
$R_5$ is hydrogen or alkyl of from 1 to 4 carbon atoms;
$R_6$ is hydrogen, chlorine, bromine, fluorine, methyl, trifluoromethyl, or methoxy; and
$R_7$ is oxygen or sulfur, in unit dosage form.
* * * * *

UNITED STATES PATENT AND TRADEMARK OFFICE
CERTIFICATE OF CORRECTION

PATENT NO. : 5,436,260
DATED : July 25, 1995
INVENTOR(S) : Hodges, et al.

It is certified that error appears in the above-indentified patent and that said Letters Patent is hereby corrected as shown below:

Column 68, line 23, delete " $CF$, " and insert instead " $F$, ".

Column 68, line 25, insert " ( " to read " $N(CH_3)_2$ ".

Column 68, line 29, first letter of the word "pyridyl," should be lower case.

Column 68, line 37, the printed subscript "e" should not be a subscript and should not be italic.

Column 68, line 37, the last letter of the line, "R", should be "H".

Column 68, line 55, large parentheses are missing from the structure. Structure should be:

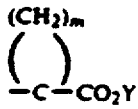

Column 68, line 64, a line is missing. Insert " $PO(OR)_2$, " before " $CONHSO_2R$, ".

Column 69, line 21, insert semicolon at end of line.

UNITED STATES PATENT AND TRADEMARK OFFICE
CERTIFICATE OF CORRECTION

PATENT NO. : 5,436,260
DATED : July 25, 1995
INVENTOR(S) : Hodges, et al.

It is certified that error appears in the above-indentified patent and that said Letters Patent is hereby corrected as shown below:

Column 69, lines 24 and 25, delete two lines beginning with "$E_6$" and ending with "and".

Column 70, line 1, "(" is missing, should be $N(CH_3)_2$.

Column 70, line 12, the printed subscript "e" should not be subscript and should not be italic.

Column 70, line 14, the third parenthesis should be an open parenthesis, not a close parenthesis.

Column 70, line 30, large parentheses are missing from the structure, should be:

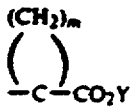

Column 70, line 37, delete entire line which reads $NHSO_2SO_2NHCOR$,

Column 70, line 68, insert the word "of" between the words "alkyl" and "from".

Column 71, line 45, insert "(" to read $N(CH_3)_2$.

UNITED STATES PATENT AND TRADEMARK OFFICE
CERTIFICATE OF CORRECTION

PATENT NO. : 5,436,260
DATED : July 25, 1995
INVENTOR(S) : Hodges, et al.

It is certified that error appears in the above-indentified patent and that said Letters Patent is hereby corrected as shown below:

Column 71, line 56, the printed subscript "e" should not be a subscript and should not be italic.

Column 71, line 58, the third parenthesis should be an open parenthesis, not a close parenthesis.

Column 72, line 6, structure is missing large parentheses should be:

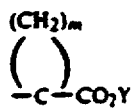

Column 72, line 13, "NHCOR," should not be a subscript and not italic.

Column 72, line 47, (third from last line in Claim 3) the subscript "5" should be subscript "6".

Column 73, line 25, insert "(" in space to read
$N(CH_3)_2$ .

Column 73, line 36, the printed subscript "e" should not be a subscript and should not be italic.

Column 73, line 37, at the end of the line delete the comma, and insert instead a semicolon.

Column 73, line 38, the subscript "m" should not be italic. The "X)" should be "X(". The "n" should be a subscript. The "H" should be on the baseline and not italic. To read $(CH_2)_m X (CH_2)_n H$ .

UNITED STATES PATENT AND TRADEMARK OFFICE
CERTIFICATE OF CORRECTION

PATENT NO. : 5,436,260
DATED : July 25, 1995
INVENTOR(S) : Hodges, et al.

It is certified that error appears in the above-indentified patent and that said Letters Patent is hereby corrected as shown below:

Column 73, line 55, large parentheses are missing from the structure, should be:

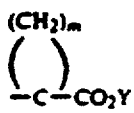

Column 75, line 7, the printed subscript "e" should not be subscript and should not be italic.

Column 75, line 25, structure is missing the large parentheses, should read:

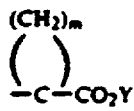

Column 76, line 37, insert "(" between the "n" and the "C" to read $N(CH_3)_2$ .

Column 76, line 47, the printed subscript "e" should not be a subscript and should not be italic.

Column 76, line 49, the third parenthesis should be an open parenthesis not a close parenthesis.

UNITED STATES PATENT AND TRADEMARK OFFICE
CERTIFICATE OF CORRECTION

PATENT NO. : 5,436,260

DATED : July 25, 1995

INVENTOR(S) : Hodges, et al.

It is certified that error appears in the above-indentified patent and that said Letters Patent is hereby corrected as shown below:

Column 76, line 63, the large parentheses are missing from the structure, should read:

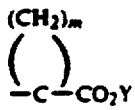

Column 77, line 7, at the end of the line, delete the subscript "m" and insert instead a comma on the baseline.

Column 78, line 8, insert "(" between the "N" and the "C" to read $N(CH_3)_2$ .

Column 78, line 17, delete "Ci," and insert instead " Cl, " .

Column 78, line 18, the printed subscript "e" should not be a subscript and should not be italic.

Column 78, line 18, insert a space in front of " $CO_2R$, " .

Column 78, line 20, the third parenthesis should be an open parenthesis not a close parenthesis.

Column 78, line 35, the structure is missing the large parentheses, should read:

Column 79, line 48, insert "(" between the "N" and the "C" to read " $N(CH_3)_2$ " .

UNITED STATES PATENT AND TRADEMARK OFFICE
CERTIFICATE OF CORRECTION

PATENT NO. : 5,436,260
DATED : July 25, 1995
INVENTOR(S) : Hodges, et al.

It is certified that error appears in the above-indentified patent and that said Letters Patent is hereby corrected as shown below:

Column 79, line 58, the "e" should not be italic and should not be a subscript.

Column 79, line 58, delete the second " $CO_2R$, " and insert instead " $CO_2H$, " .

Column 79, line 61, the third parenthesis should be an open parenthesis rather than a close parenthesis, and the subscript "m" should not be italic, and the "n" should be lowered to subscript position, and the superscript "H" should be on the baseline and not italic, to read " $(CH_2)_m X (CH_2)_n H$ " .

Column 80, line 10, the large parentheses are missing from the structure, should read:

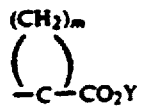

Column 81, line 36, the "e" should not be a subscript and should not be italic.

Column 81, line 38, the beginning of the line should read " $(CH_2)_m X (CH_2)_n H$ " .

UNITED STATES PATENT AND TRADEMARK OFFICE
CERTIFICATE OF CORRECTION

PATENT NO. : 5,436,260
DATED : July 25, 1995
INVENTOR(S) : Hodges, et al.

It is certified that error appears in the above-indentified patent and that said Letters Patent is hereby corrected as shown below:

Column 81, line 55, the large parenthesis are missing from the structure, should read:

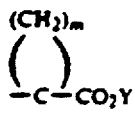

Column 82, line 68, last line, insert "(" between the "N" and the "C" to read  " N(CH$_3$)$_2$ " .

Column 83, line 3, the second word should be " 2-pyrrolyl, " not "2-pyridyl, " .

Column 83, line 10, the printed subscript "e" should not be a subscript and should not be italic.

Column 83, line 12, the subscript "m" should not be italic, the third parenthesis should be an open parenthesis not a close parenthesis, the subscript "n" should not be italic.

Column 83, line 27, the large parentheses are missing from the structure, should read:

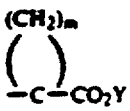

UNITED STATES PATENT AND TRADEMARK OFFICE
CERTIFICATE OF CORRECTION

PATENT NO. : 5,436,260
DATED : July 25, 1995
INVENTOR(S) : Hodges, et al.

It is certified that error appears in the above-indentified patent and that said Letters Patent is hereby corrected as shown below:

Column 84, line 47, the subscript "e" should be moved to the baseline and not italic.

Column 84, line 49, the subscripts "m" and "n" should not be italic.

Column 84, line 65, the large parentheses are missing from the structure, should read:

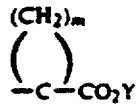

Column 85, lines 12-24, delete the structure and the word "or" and insert instead:

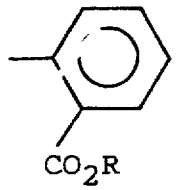

$SO_2NHCONHR$, $NHSO_2CF_3$,

Column 86, line 12, insert "(" between the "N" and "C" to read "  $N(CH_3)_2$  ".

UNITED STATES PATENT AND TRADEMARK OFFICE
CERTIFICATE OF CORRECTION

PATENT NO. : 5,436,260
DATED : July 25, 1995
INVENTOR(S) : Hodges, et al.

It is certified that error appears in the above-indentified patent and that said Letters Patent is hereby corrected as shown below:

Column 86, line 23, the subscript "e" should be moved to the baseline and not italic.

Column 86, line 25, the subscripts "m" and "n" should not be italic, and the third parenthesis should be an open parenthesis not a close parenthesis.

Column 86, line 42, the large parenthesis are missing from the structure, should be:

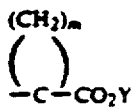

Column 88, line 1, after line 1 insert the line:
$R_4$ is $R_1$;

Signed and Sealed this

Second Day of April, 1996

Attest:

BRUCE LEHMAN

*Attesting Officer*  *Commissioner of Patents and Trademarks*